United States Patent
Ju et al.

(10) Patent No.: US 7,982,029 B2
(45) Date of Patent: Jul. 19, 2011

(54) SYNTHESIS OF FOUR COLOR 3'O-ALLYL, MODIFIED PHOTOCLEAVABLE FLUORESCENT NUCLEOTIDES AND RELATED METHODS

(75) Inventors: Jingyue Ju, Englewood Cliffs, NJ (US); Qinglin Meng, Sunnyvale, CA (US); Dae H. Kim, New York, NY (US); Lanrong Bi, New York, NY (US); Xiaopeng Bai, Watertown, MA (US); Nicholas J. Turro, Tenafly, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 49 days.

(21) Appl. No.: 12/084,338

(22) PCT Filed: Oct. 31, 2006

(86) PCT No.: PCT/US2006/042698
§ 371 (c)(1),
(2), (4) Date: Oct. 16, 2009

(87) PCT Pub. No.: WO2007/053702
PCT Pub. Date: May 10, 2007

(65) Prior Publication Data
US 2010/0041029 A1    Feb. 18, 2010

Related U.S. Application Data

(60) Provisional application No. 60/732,373, filed on Oct. 31, 2005.

(51) Int. Cl.
*C07H 21/00* (2006.01)
*C07H 21/02* (2006.01)
*C12Q 1/68* (2006.01)
*C12P 19/34* (2006.01)

(52) U.S. Cl. .............. 536/25.3; 536/23.1; 536/24.3; 536/26.6; 435/6; 435/91.1; 435/91.2

(58) Field of Classification Search ............ 435/6, 91.1, 435/91.2; 536/23.1, 24.3, 25.3, 26.6
See application file for complete search history.

(56) References Cited

U.S. PATENT DOCUMENTS 6,664,079 B2    12/2003    Ju et al. ................. 435/91.1

OTHER PUBLICATIONS

International Search Report issued by the International Searching Authority (ISA/US) on Nov. 23, 2007 in connection with International Application No. PCT/US2006/042698.*
Written Opinion issued by the International Searching Authority (ISA/US) on Nov. 23, 2007 in connection with International Application No. PCT/US2006/042698.*
Meng, Q., et al. "Design and Synthesis of a Photocleavable Fluorescent Nucleotide 3'-O-Allyl-dGTP-PC-Bodipy-FL-510 as a Reversible Terminator for DNA Sequencing by Synthesis" J. Org. Chem. (2006), 71, 3248-3252.*
Ruparel, H., et al. "Design and synthesis of a 3'-O-allyl photocleavable fluorescent nucleotide as a reversible terminator for DNA sequencing by synthesis" PNAS, 2005, vol. 102, No. 17, 5932-5937.*
Seo, T.S., et al. "Four-color DNA sequencing by synthesis on a chip using photocleavable fluorescent nucleotides" PNAS, 2005, vol. 102, No. 17, 5926-5931.*
Seo, T.S., et al. "Photocleavable fluorescent nucleotides for DNA sequencing on a chip constructed by site-specific coupling chemistry" PNAS, 2004, vol. 101, No. 15, 5488-5493.*
Li, Z., et al. "A photocleavable fluorescent nucleotide for DNA sequencing and analysis" PNAS, 2003, vol. 100, No. 2, 414-419.*

* cited by examiner

*Primary Examiner* — Jezia Riley
(74) *Attorney, Agent, or Firm* — John P. White; Cooper & Dunham LLP

(57) ABSTRACT

This invention provides a process for making 3'-O-allyl-dGTP-PC-Biodpy-FL-510, 3'-O-allyl-dATP-PC-ROX, 3'-O-allyl-dCTP-PC-Bodipy-650 and 3'-O-allyl-dUTP-PC-R6G, and related methods.

4 Claims, 22 Drawing Sheets

US 7,982,029 B2

SYNTHESIS OF FOUR COLOR 3'O-ALLYL, MODIFIED PHOTOCLEAVABLE FLUORESCENT NUCLEOTIDES AND RELATED METHODS

This application is a §371 national stage of PCT International Application No. PCT/US2006/042698, filed Oct. 31, 2006, and claims the benefit of U.S. Provisional Application No. 60/732,373, filed Oct. 31, 2005, the contents of all of which are hereby incorporated by reference into this application.

This invention was made with Government support under Center of Excellence in Genomic Science Grant No. IP50 HG002806-01 awarded by the National Institutes of Health, U.S. Department of Health and Human Services. Accordingly, the U.S. Government has certain rights in this invention.

Throughout this application, various publications are referenced in parentheses by number. Full citations for these references may be found at the end of each experimental section. The disclosures of these publications in their entireties are hereby incorporated by reference into this application to more fully describe the state of the art to which this invention pertains.

BACKGROUND OF THE INVENTION

DNA sequencing is a fundamental tool for biological research and medical diagnostics, driving disease gene discovery and gene function studies. DNA sequencing by synthesis (SBS) using reversible fluorescent nucleotide terminators1 is a potentially efficient approach to address the limitations of current DNA sequencing techniques, such as throughput and data accuracy. A 3'-O-allyl photocleavable (PC) fluorescent nucleotide analogue, 3'-O-allyl-dUTP-PC-Bodipy-FL-510, as a reversible terminator for SBS has previously been reported (2). The nucleotide can be efficiently incorporated by DNA polymerase into a growing DNA strand to terminate the polymerase reaction. After that the fluorophore can be photocleaved quantitatively by irradiation at 355 nm, and the allyl group is rapidly and efficiently removed by using a Pd-catalyzed reaction in water to regenerate a free 3'-OH group to reinitiate the polymerase reaction.

SUMMARY

This invention provides a method for making 3'O-allyl-dGTP-PC-Bodipy-FL-510 comprising performing the steps set forth in FIG. 7. This invention also provides a method for making 3'-O-allyl-dATP-PC-ROX comprising performing the steps set forth in FIG. 8. This invention also provides a method for making 3'-O-allyl-dCTP-PC-Bodipy-650 comprising performing the steps set forth in FIG. 9. This invention also provides a method for making 3'-O-allyl-dUTP-PC-R6G comprising performing the steps set forth in FIG. 10.

This invention also provides a method for making method for determining the sequence of a DNA comprising performing the following steps for each residue of the DNA to be sequenced:

(a) contacting the DNA with a DNA polymerase in the presence of (i) a primer and (ii) four fluorescent nucleotide analogues under conditions permitting the DNA polymerase to catalyze DNA synthesis, wherein (1) the nucleotide analogues consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, (ii) a deoxyribose, (iii) a fluorophore photocleavably attached to the base, and (iv) an allyl moiety bound to the 3'-oxygen of the deoxyribose, so that a nucleotide analogue complementary to the residue being sequenced is bound to the DNA by the DNA polymerase, and (3) each of the four analogues has a predetermined fluorescence wavelength which is different than the fluorescence wavelengths of the other three analogues;

(b) removing unbound nucleotide analogues;

(c) determining the identity of the bound nucleotide analogues; and (d) following step (c), except with respect to the final DNA residue to be sequenced, (i) chemically cleaving from the bound nucleotide analogue the allyl moiety bound to the 3'-oxygen atom of the deoxyribose and (ii) photocleaving the fluorophore from the bound nucleotide analogue, wherein steps (d) (i) and (d) (ii) can be performed concurrently or in any order, and step (d) (i) is performed using a Pd catalyst at a pH of about 8.8, thereby determining the sequence of the DNA.

This invention also provides a method for removing an allyl moiety from the 3'-oxygen of a nucleotide analogue's deoxyribose moiety comprising the step of contacting the nucleotide analogue with a Pd catalyst at a pH of about 8.8.

DETAILED DESCRIPTION OF THE INVENTION

Terms

Figure 1:
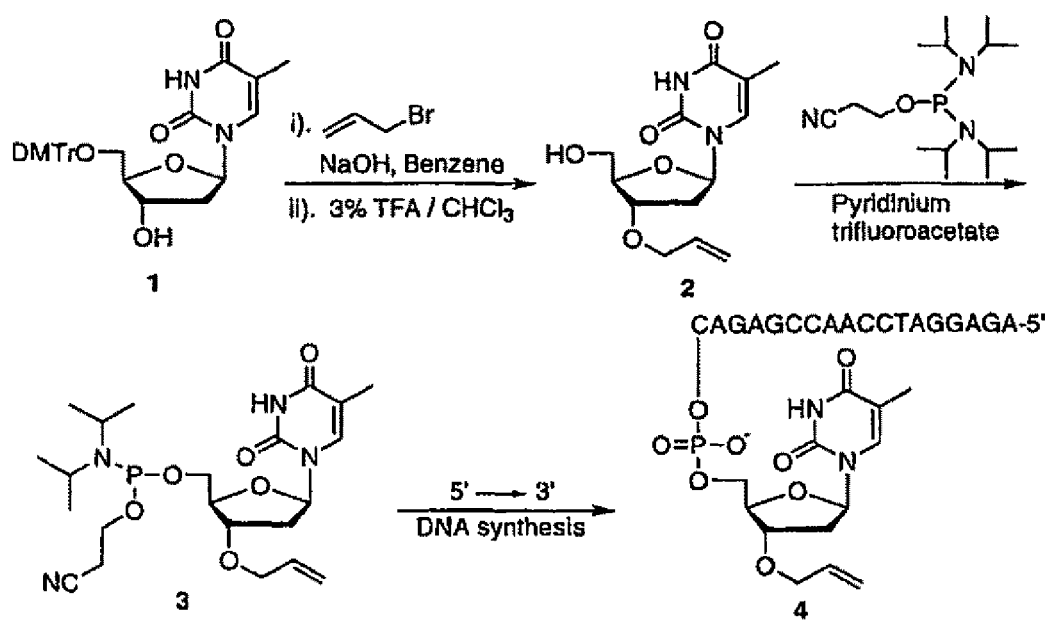
FIG. 1: Synthesis of a 3'-O-allyl modified 19-mer oligonucleotide.

The following definitions are presented as an aid in understanding this invention:
A—Adenine;
C—Cytosine;
DNA—Deoxyribonucleic acid;
G—Guanine;
PC—Photocleavable
RNA—Ribonucleic acid;
SBS—Sequencing by synthesis;
T—Thymine; and
U—Uracil.

"Nucleic acid" shall mean any nucleic acid, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996 1997, Roche Molecular Systems, Inc., Branchburg, N.J., USA).

As used herein, "self-priming moiety" shall mean a nucleic acid moiety covalently bound to a nucleic acid to be transcribed, wherein the bound nucleic acid moiety, through its proximity with the transcription initiation site of the nucleic acid to be transcribed, permits transcription of the nucleic acid under nucleic acid polymerization-permitting conditions (e.g. the presence of a suitable polymerase, nucleotides and other reagents). That is, the self-priming moiety permits the same result (i.e. transcription) as does a non-bound primer. In one embodiment, the self-priming moiety is a single stranded nucleic acid having a hairpin structure. Examples of such self-priming moieties are shown in the Figures.

"Hybridize" shall mean the annealing of one single-stranded nucleic acid to another nucleic acid based on sequence complementarity. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York.)

As used herein, "nucleotide analogue" shall mean an analogue of A, G, C, T or U (that is, an analogue of a nucleotide comprising the base A, G, C, T or U) which is recognized by DNA or RNA polymerase (whichever is applicable) and incorporated into a strand of DNA or RNA (whichever is appropriate). Examples of nucleotide analogues include, without limitation 7-deaza-adenine, 7-deaza-guanine, the analogues of deoxynucleotides shown in FIG. 6, analogues in which a label is attached through a cleavable linker to the 5-position of cytosine or thymine or to the 7-position of deaza-adenine or deaza-guanine, analogues in which a small chemical moiety such as —CH$_2$CH=CH$_2$ is used to cap the —OH group at the 3'-position of deoxyribose, and analogues of related dideoxynucleotides. Nucleotide analogues, including dideoxynucleotide analogues, and DNA polymerase-based DNA sequencing are also described in U.S. Pat. No. 6,664,079.

1,3 dipolar azide-alkyne cycloaddition chemistry is described in WO 2005/084367 and PCT/US03/39354, the contents of each of which are hereby incorporated by reference.

All embodiments of U.S. Pat. No. 6,664,079 (the contents of which are hereby incorporated by reference) with regard to sequencing a nucleic acid are specifically envisioned here.

With regard to the synthesis of the nucleotide analogues disclosed herein, other fluorophores or chromophores to be photocleavably attached to the base of the analogue are envisioned. In addition, combinatorial fluorescence energy tags as described in U.S. Pat. No. 6,627,748 (the contents of which are hereby incorporated by reference) may be used in place of the fluorophores described herein.

Embodiments of the Invention

Figure 7:
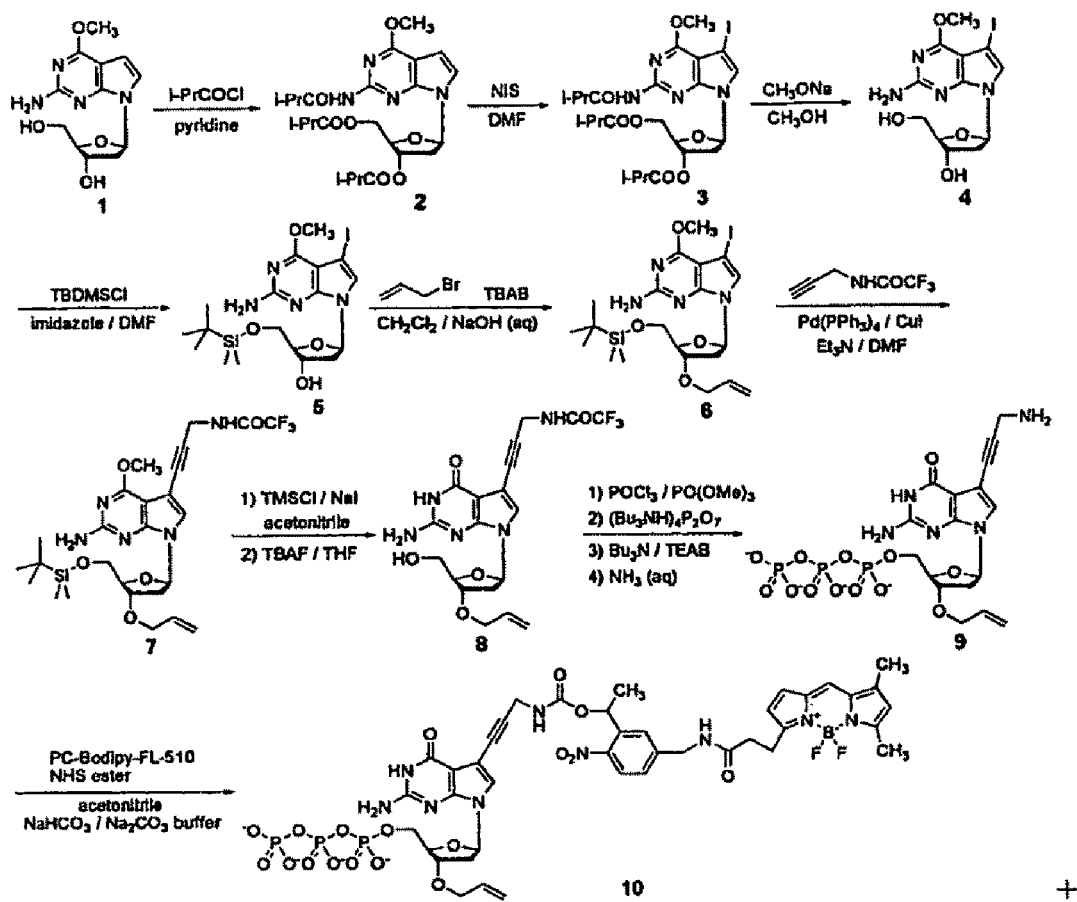
FIG. 7: Synthesis of 3'-O-allyl-dGTP-PC-Bodipy-FL-510 10.

This invention provides a method for making 3'O-allyl-dGTP-PC-Bodipy-FL-510 comprising performing the steps set forth in FIG. 7. This invention also provides a method for making 3'-O-allyl-dATP-PC-ROX comprising performing the steps set forth in FIG. 8. This invention also provides a method for making 3'-O-allyl-dCTP-PC-Bodipy-650 comprising performing the steps set forth in FIG. 9. This invention also provides a method for making 3'-O-allyl-dUTP-PC-R6G comprising performing the steps set forth in FIG. 10.

This invention also provides a method for making method for determining the sequence of a DNA comprising performing the following steps for each residue of the DNA to be sequenced:

(a) contacting the DNA with a DNA polymerase in the presence of (i) a primer and (ii) four fluorescent nucleotide analogues under conditions permitting the DNA polymerase to catalyze DNA synthesis, wherein (1) the nucleotide analogues consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, (ii) a deoxyribose, (iii) a fluorophore photocleavably attached to the base, and (iv) an allyl moiety bound to the 3'-oxygen of the deoxyribose, so that a nucleotide analogue complementary to the residue being sequenced is bound to the DNA by the DNA polymerase, and (3) each of the four analogues has a predetermined fluorescence wavelength which is different than the fluorescence wavelengths of the other three analogues;

(b) removing unbound nucleotide analogues;

(c) determining the identity of the bound nucleotide analogues; and (d) following step (c), except with respect to the final DNA residue to be sequenced, (i) chemically cleaving from the bound nucleotide analogue the allyl moiety bound to the 3'-oxygen atom of the deoxyribose and (ii) photocleaving the fluorophore from the bound nucleotide analogue, wherein steps (d) (i) and (d)(ii) can be performed concurrently or in any order, and step (d)(i) is performed using a Pd catalyst at a pH of about 8.8, thereby determining the sequence of the DNA.

In one embodiment of the instant method, chemically cleaving the allyl moiety bound to the 3'-oxygen atom is performed using Na$_2$PdCl$_4$.

In one embodiment of the instant method, the primer is a self-priming moiety.

In one embodiment of the instant method, the DNA is bound to a solid substrate. In one embodiment of the instant method, the DNA is bound to the solid substrate via 1,3-dipolar azide-alkyne cycloaddition chemistry. In one embodiment of the instant method, about 1000 or fewer copies of the DNA are bound to the solid substrate.

In one embodiment of the instant method, the four fluorescent nucleotide analogues are 3'-O-allyl-dGTP-PC-Bodipy-FL-510, 3'-O-allyl-dATP-PC-ROX, 3'-O-allyl-dCTP-PC-Bodipy-650 and 3'-O-allyl-dUTP-PC-R6G.

In one embodiment of the instant method, the DNA polymerase is a 9° N polymerase.

This invention also provides a method for removing an allyl moiety from the 3'-oxygen of a nucleotide analogue's deoxyribose moiety comprising the step of contacting the nucleotide analogue with a Pd catalyst at a pH of about 8.8. In one embodiment of the instant method, the Pd catalyst is Na$_2$PdCl$_4$.

In embodiments of this invention the sequencing methods described can be applied, mutatis mutandis, to sequencing an RNA molecule or an RNA/DNA hybrid molecule.

This invention will be better understood by reference to the Experimental Details which follow, but those skilled in the art will readily appreciate that the specific experiments detailed are only illustrative of the invention as described more fully in the claims which follow thereafter.

Experimental Details

The design and synthesis of a complete set of four-color 3'-O-allyl modified photocleavable fluorescent nucleotides as reversible terminators for SBS is disclosed herein.

EXAMPLE 1

Synopsis

DNA sequencing by synthesis (SBS) offers a new approach for potential high-throughput sequencing applications. In this method, the ability of an incoming nucleotide to act as a reversible terminator for a DNA polymerase reaction is an important requirement to unambiguously determine the identity of the incorporated nucleotide before the next nucleotide is added. A free 3'-OH group on the terminal nucleotide of the primer is necessary for the DNA polymerase to incorporate an incoming nucleotide. Therefore, if the 3'-OH group of an incoming nucleotide is capped by a chemical moiety, it will cause the polymerase reaction to terminate after the nucleotide is incorporated into the DNA strand. If the capping group is subsequently removed to generate a free 3'-OH, the polymerase reaction will reinitialize. Here, the design and synthesis of a 3'-modified photocleavable fluorescent nucleotide, 3'-O-allyl-dUTP-PC-Bodipy-FL-510, as a reversible terminator for SBS is disclosed. This nucleotide analogue contains an allyl moiety capping the 3'-OH group and a fluorophore Bodipy-FL-510 linked to the 5 position of the uracil through a photocleavable 2-nitrobenzyl linker. In addition, it is shown that this nucleotide is a good substrate for a DNA polymerase. After the nucleotide was successfully incorporated into a growing DNA strand and the fluorophore photocleaved, the allyl group was removed using a Pd catalyzed reaction to reinitiate the polymerase reaction, thereby establishing the feasibility of using such nucleotide analogues as reversible terminators for SBS.

Introduction

The completion of the Human Genome Project (1, 2) has led to an increased demand for high-throughput and rapid DNA sequencing methods to identify genetic variants for applications in pharmacogenomics (3), disease gene discovery (4, 5) and gene function studies (6). Current state-of-the-art DNA sequencing technologies (7-11) to some extent address the accuracy and throughput requirements but suffer limitations with respect to cost and data quality. Thus, new DNA sequencing approach is required to broaden the applications of genomic information in medical research and health care. In this regard, DNA sequencing by synthesis (SBS) offers an alternative approach to possibly address the limitations of current DNA sequencing techniques. The design of a parallel chip based SBS system, which uses a self-priming DNA template covalently linked to the glass surface of a chip and four modified nucleotides has previously been described (12-14). The nucleotides are modified such that they have a photocleavable fluorescent moiety attached to the base (5 position of pyrimidines, 7 position of purines) and a chemically cleavable group to cap the 3'-OH. When the correct nucleotide is incorporated in a DNA polymerase reaction, specific to the template sequence, the reaction is temporarily terminated because of the lack of a free 3'-OH group. After the fluorescent signal is detected and the nucleotide identified, the 3'-OH needs to be regenerated in order to continue incorporating the next nucleotide. In Example 3 hereinbelow, it is demonstrated that 4 photocleavable fluorescent nucleotides can be efficiently incorporated by DNA polymerase into a growing DNA strand base specifically in a polymerase extension reaction, and the fluorophores can be completely removed by photocleavage under near UV irradiation ($\lambda$~355 nm) with high efficiency (15). Using this system in a four-color sequencing assay, accurate identification of multiple bases in a self-priming DNA template covalently attached to a glass surface can be achieved.

Another important requirement for this approach to sequence DNA unambiguously is a suitable chemical moiety to cap the 3'-OH of the nucleotide such that it terminates the polymerase reaction to allow the identification of the incorporated nucleotide. The capping group then needs to be efficiently removed to regenerate the 3'-OH thereby allowing the polymerase reaction to continue. Thus, the photocleavable fluorescent nucleotides used in SBS must be reversible terminators of the DNA polymerase reaction to allow the detection of the fluorescent signal such that the complementary DNA synthesis and sequence identification can be efficiently performed in tandem. The principal challenge posed by this requirement is the incorporation ability of the 3'-modified nucleotide by DNA polymerase into the growing DNA strand. The 3'-position on the sugar ring of a nucleotide is very close to the amino acid residues in the active site of the DNA polymerase. This is supported by the 3-D structure of the previously determined ternary complexes of rat DNA polymerase, a DNA template-primer, and dideoxycytidine triphosphate (16). Thus, any bulky modification at this position provides steric hindrance to the DNA polymerase and prevents the nucleotide from being incorporated. A second challenge is the efficient removal of the capping group once the fluorescence signal is detected. Thus, it is important to use a functional group small enough to present no hindrance to DNA polymerase, stable enough to withstand DNA extension reaction conditions, and able to be removed easily and rapidly to regenerate a free 3'-OH under specific conditions.

Results

Numerous studies have previously been undertaken to identify a 3'-modified nucleotide as a substrate for DNA polymerase. 3'-O-methyl-nucleotides have been shown to be good substrates for several polymerases (17). However, the procedure to chemically cleave the methyl group is stringent and requires anhydrous conditions. Thus, it is not practical to use a methyl group to cap the 3'-OH group for SBS. It has been reported that nucleotides with ether linkages at the 3' position can be incorporated by some DNA polymerases, while those with ester linkages are not generally accepted by most of the polymerases tested (18). Significant efforts have been dedicated to evaluate a wide variety of 3'-modified nucleotides to be used as terminators for various DNA polymerases and reverse transcriptases but none of the functional groups tested have had established methods to regenerate a free 3'-OH (19-22).

It is known that stable chemical functionalities such as allyl ($-CH_2-CH=CH_2$) and methoxymethyl ($-CH_2-O-CH_3$) groups can be used to cap an OH group, and can be cleaved chemically with high yield (23, 24). Use of such groups as reversible caps for the 3'-OH of the nucleotide for SBS (12) is investigated here, and the establishment of the allyl group as a 3'-OH capping moiety for the nucleotide analogues that can be used in SBS is revealed. The choice of this group was based on the fact that the allyl moiety, being relatively small, would not provide significant hindrance for the polymerase reaction, and therefore allow the incoming 3'-O-allyl modified nucleotide analogue to be accepted by DNA polymerase. Furthermore, it was proposed to remove this group using catalytic deallylation. Here, the synthesis of a photocleavable fluorescent nucleotide analogue, 3'-O-allyl-dUTP-PC-Bodipy-FL-510, that can be efficiently incorporated by DNA polymerase into a growing DNA strand is shown. The allyl group can be rapidly and completely removed by a Pd catalyzed reaction to regenerate a 3'-OH group and the deallylated DNA can then allow reinitiation of the polymerase reaction to incorporate the subsequent nucleotide analogue.

Materials and Methods

All chemicals were purchased from Sigma-Aldrich unless otherwise indicated. Oligonucleotides used as primers or templates were synthesized on an EXPEDITE Nucleic Acid Synthesizer (Applied Biosystems). $^1$H NMR spectra were recorded on a Bruker 400 spectrometer, while $^{13}$C and $^{31}$P NMR spectra were recorded on a Bruker 300 spectrometer. High-resolution MS (HRMS) data were obtained by using a JEOL JMS HX 110A mass spectrometer. Mass measurement of DNA was made on a Voyager DE matrix-assisted laser desorption ionization time-of-flight (MALDI-TOF) mass spectrometer (Applied Biosystems). Photolysis was performed using a Spectra Physics GCR-150-30 Nd-YAG laser that generates light pulses at 355 nm (ca. 50 mJ/pulse, pulse length ca. 7 ns) at a frequency of 30 Hz with a light intensity at ca. 1.5 W/cm$^2$. Thermo Sequenase DNA Polymerase, HIV-1 and RAV2 Reverse Transcriptases were obtained from Amersham Biosciences. Therminator, Vent (exo-), Deep Vent (exo-), Bst and Klenow (exo-) fragment DNA Polymerases were obtained from New England Biolabs. 9° N Polymerase (exo-) A485L/Y409V was generously provided by New England Biolabs. Sequenase V2 DNA Polymerase, M-MulV and AMV Reverse Transcriptases were obtained from USB Corporation (Cleveland, Ohio). Tfl and Tth DNA Polymerases were obtained from Promega Corporation (Madison, Wis.). Pfu (exo-) DNA Polymerase was obtained from Stratagene, Inc. (La Jolla, Calif.). Phosphoramidites and columns for nucleic acid synthesis were obtained from Glen Research (Sterling, Va.).

Synthesis of a 3'-O-allyl Modified 19-mer oligonucleotide

3'-O-allyl-thymidine phosphoramidite 3, prepared according to FIG. 1 was used to synthesize a 19-mer oligonucleotide 5'-AGA-GGA-TCC-AAC-CGA-GAC-T(allyl)-3' 4 (SEQ ID NO:1) (MW=5871). The synthesis was carried out in the 5' to 3' direction using 3 along with dA-5'-CE, dC-5'-CE, dG-5'-CE and dT-5'-CE phosphoramidites and a dA-5'-CPG column. The oligonucleotide was purified by HPLC using an Xterra MS C18 (4.6×50 mm) column (Waters). The elution was performed over 90 min at a flow rate of 0.5 ml/min and a fixed temperature of 50° C. using a linear gradient (12-34.5%) of methanol in a buffer containing 8.6 mM triethylamine and 100 mM hexafluoroisopropyl alcohol (pH=8.1). The product was characterized using MALDI-TOF MS.

Deallylation Reaction Performed Using the 3'-O-allyl Modified 19-mer oligonucleotide For the deallylation reaction, 55 equivalents of $Na_2PdCl_4$ and 440 equivalents of a trisodium triphenylphosphinetrisulfonate (TPPTS) ligand were used in water at 70° C. $Na_2PdCl_4$ in degassed water (0.7 µl, 2.2 nmol) was added to a solution of TPPTS in degassed water (1 µl, 17.6 nmol) and mixed well. After 5 min, a solution of 3'-O-allyl modified oligonucleotide 4 (1 µl, 40 pmol) was added. The reaction mixture was then placed in a heating block at 70° C. and incubated for 30 seconds. The resulting deallylated product was desalted by Zip Tip (Millipore Corporation) and analyzed using MALDI-TOF MS.

Primer Extension Reaction Performed with the Deallylated DNA Product

The 10 µl extension reaction mixture consisted of 45 pmol of the deallylated DNA product as a primer, 100 pmol of a single-stranded synthetic 100-mer DNA template (sequence shown in reference 15) corresponding to a portion of exon 7 of the p53 gene, 100 pmol of Biotin-11-2',3'-dideoxyguanosine-5'-triphosphate (Biotin-11-ddGTP) terminator (Perkin Elmer), 1× Thermo Sequenase reaction buffer and 4 U of Thermo Sequenase DNA Polymerase. The extension reaction consisted of 15 cycles at 94° C. for 20 sec, 4.8° C. for 30 sec and 60° C. for 60 sec. The product was purified using solid phase capture on streptavidin-coated magnetic beads (25), desalted using Zip Tip and analyzed using MALDI-TOF MS.

Synthesis of 3'-O-allyl-dUTP-PC-Bodipy-FL-510

Figure 2:
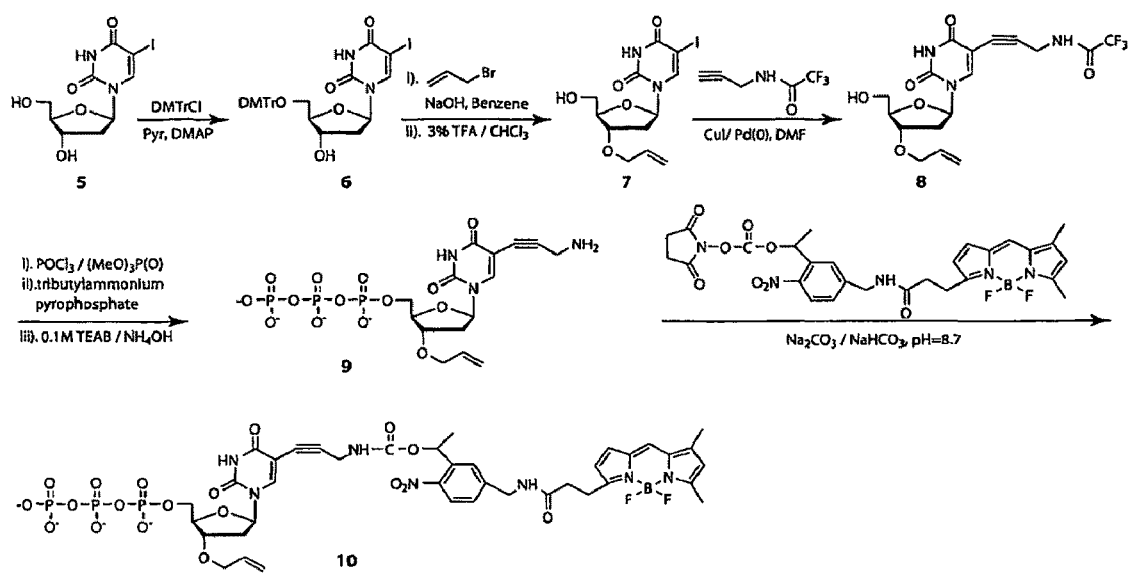
FIG. 2: Synthesis of 3'-O-allyl-dUTP-PC-Bodipy-FL-510.

3'-O-allyl-dUTP-PC-Bodipy-FL-510 10 was synthesized as shown in FIG. 2. Detailed synthesis procedures and characterization data for all intermediate compounds (6-9) are described in the supporting information.

PC-Bodipy-FL-510 NHS ester (13) (7.2 mg, 12 mmol) in 300 µl of acetonitrile was added to a solution of 3'-O-allyl-5-(3-aminoprop-1-ynyl)-2'-deoxyuridine-5'-triphosphate 9 (2 mg, 4 mmol) in 300 µl of $Na_2CO_3$—$NaHCO_3$ buffer (0.1 M, pH 8.7). The reaction mixture was stirred at room temperature for 3 h. A preparative silica-gel TLC plate was used to separate the unreacted PC-Bodipy-FL-510 NHS ester from the fractions containing 10 ($CHCl_3/CH_3OH$, 85/15). The product was concentrated further under vacuum and purified with reverse-phase HPLC on a 150 4.6-mm C18 column to obtain the pure product 10 (retention time=35 min). Mobile phase: A, 8.6 mM triethylamine/100 mM hexafluoroisopropyl alcohol in water (pH 8.1); B, methanol. Elution was performed with 100% A isocratic over 10 min followed by a linear gradient of 0-50% B for 20 min and then 50% B isocratic over another 20 min. 3'-O-allyl-dUTP-PC-Bodipy-FL-510 10 was characterized by the following single base extension reaction and MALDI-TOF MS.

Primer Extension Using 3'-O-allyl-dUTP-PC-Bodipy-FL-510 and Photocleavage of the Extension Product An 18-mer oligonucleotide 5'-AGA-GGA-TCC-AAC-CGA-GAC-3' (SEQ ID NO: 2) (MW=5907) was synthesized using dA-CE, dC-CE, dG-CE and Biotin-dT phosphoramidites. A primer extension reaction was performed using a 15 (1 reaction mixture consisting of 50 pmol of primer, 100 pmol of single-stranded synthetic 100-mer DNA template corresponding to a portion of exon 7 of the p53 gene (15), 200 pmol of 3'-O-allyl-dUTP-PC-Bodipy-FL-510, 1× Thermopol reaction buffer (New England Biolabs) and 15 U of 9(N Polymerase (exo-) A485L/Y409V. The extension reaction consisted of 15 cycles of 94 (C for 20 sec, 48 (C for 30 sec and 60 (C for 60 sec. A small portion of the DNA extension product 11 was desalted using Zip Tip and analyzed using MALDI-TOF MS. The rest of the product was freeze-dried, resuspended in 200 (1 of deionized water and irradiated for 10 sec in a quartz cell with path lengths of 1.0 cm employing an Nd-YAG laser ((~355 nm) to cleave the fluorophore from the DNA, yielding product 12.

Deallylation of the DNA Extension Product Generated by the Incorporation of 3'-O-allyl-dUTP-PC-Bodipy-FL-510

The above photocleaved 3'-O-allyl modified DNA product 12 (180 pmol produced in multiple reactions) was dried and resuspended in 1 (1 of deionized H2O. Na2PdCl4 in degassed H2O (4.1 (1, 72 nmol) was added to a solution of TPPTS in degassed H2O (2.7 (1, 9 nmol) and mixed well. After 5 min, the above DNA product (1 (1, 180 pmol) was added. The reaction mixture was then placed in a heating block, incubated at 70° C. for 90 sec to yield deallylated product 13, and then cooled to room temperature for analysis by MALDI-TOF MS.

Polymerase Extension and Photocleavage Using the Deallylated DNA Product as a Primer The above deallylated DNA product 13 was used as a primer in a single base extension reaction. The 10 (1 reaction mixture consisted of 50 pmol of the above deallylated product 13, 125 pmol of dGTP-PC-Bodipy-FL-510 (14), 4 U of Thermo Sequenase DNA Polymerase and 1× reaction buffer. The extension reaction consisted of 15 cycles of 94 (C for 20 sec, 48 (C for 30 sec and 60 (C for 60 sec. The DNA extension product 14 was desalted using the Zip Tip protocol and a small portion was analyzed using MALDI-TOF MS. The remaining product was then irradiated with near UV light for 10 sec to cleave the fluorophore from the extended DNA product. The resulting photocleavage product 15 was desalted and analyzed using MALDI-TOF MS.

Discussion

It is shown here that an allyl moiety can be successfully used as a blocking group for the 3'-OH of a photocleavable fluorescent nucleotide analogue in SBS to prevent the DNA polymerase reaction from continuing after the incorporation of the 3'-O-allyl modified nucleotide analogue. Furthermore, it is demonstrated that the allyl group can be efficiently removed to generate a free 3'-OH group and allow the DNA polymerase reaction to continue to the subsequent cycle.

Conventional methods for cleavage of the allyl group combine a transition metal-catalyzed isomerization of the double bond to the enol ether and subsequent hydrolysis of the latter to produce the corresponding alcohol (26, 27). For application in SBS, it is important to ensure that complete chemical cleavage of the 3'-O-allyl group can be rapidly and specifically carried out while leaving the DNA intact. Trisodium triphenylphosphinetrisulfonate (TPPTS) has been widely used as a ligand for Pd mediated deallylation under aqueous conditions (28-30), while an active Pd catalyst can be generated from Na2PdCl4 and an appropriate ligand (31, 32). Thus, a water-soluble Pd catalyst system generated from $Na_2PdCl_4$ and TPPTS was investigated for deallylation of the 3'-O-allyl modified DNA product.

Figure 3:
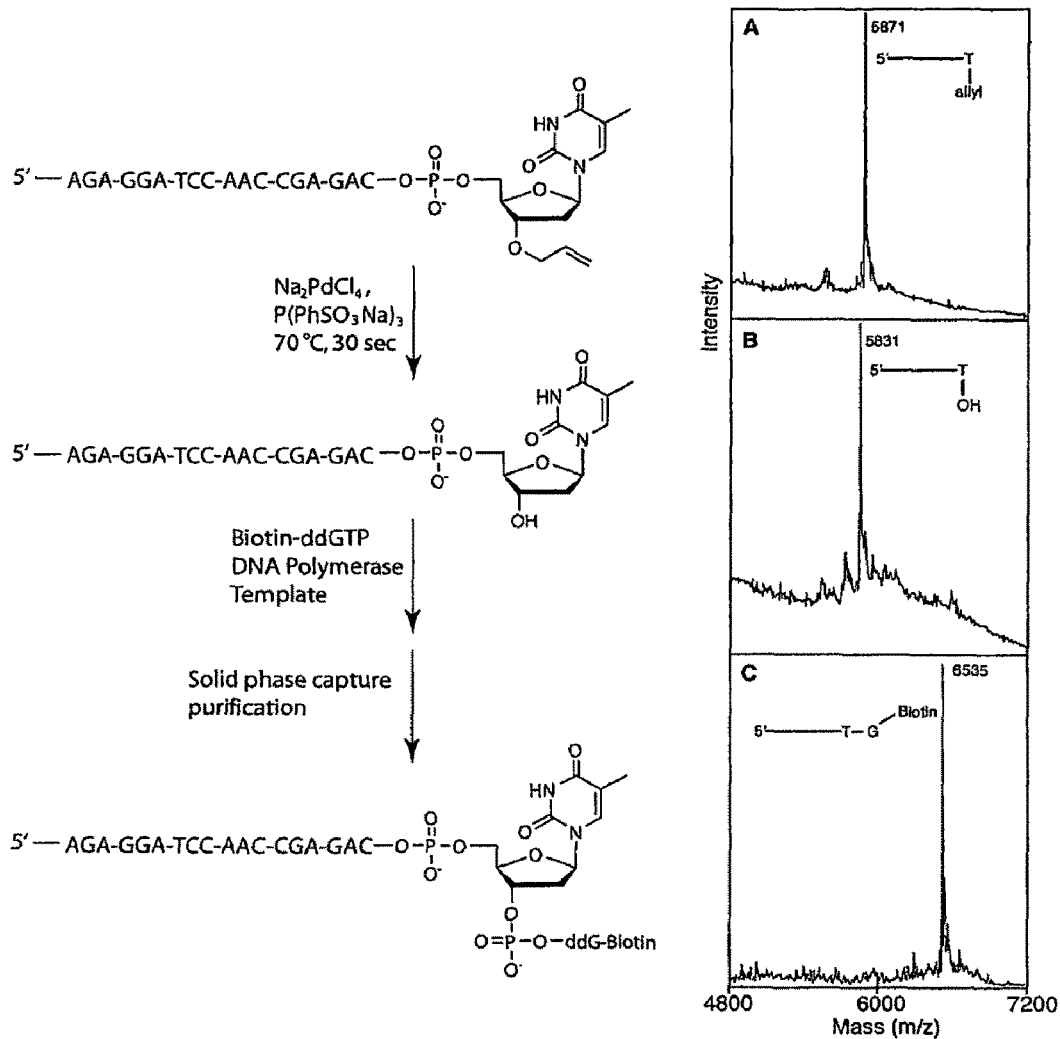
FIG. 3: Schematic representation (left) and step-by-step MALDI-TOF MS results (right) for the deallylation of a 3'-O-allyl-modified oligonucleotide and the use of the deallylated oligonucleotide as a primer in a polymerase extension reaction. (A) Peak at m/z 5871 corresponding to the HPLC-purified 3'-O-allyl modified 19-mer oligonucleotide. (B) Peak at m/z 5831 corresponding to the above oligonucleotide without the allyl group, obtained after 30 sec of incubation with $Na_2PdCl_4$ and TPPTS $[P(PhSO_3Na)_3]$ at 70° C. (C) Peak at m/z 6535 corresponding to the extension of the deallylated oligonucleotide by Biotin-11-ddGTP using Thermo Sequenase DNA polymerase.
Figure 4:
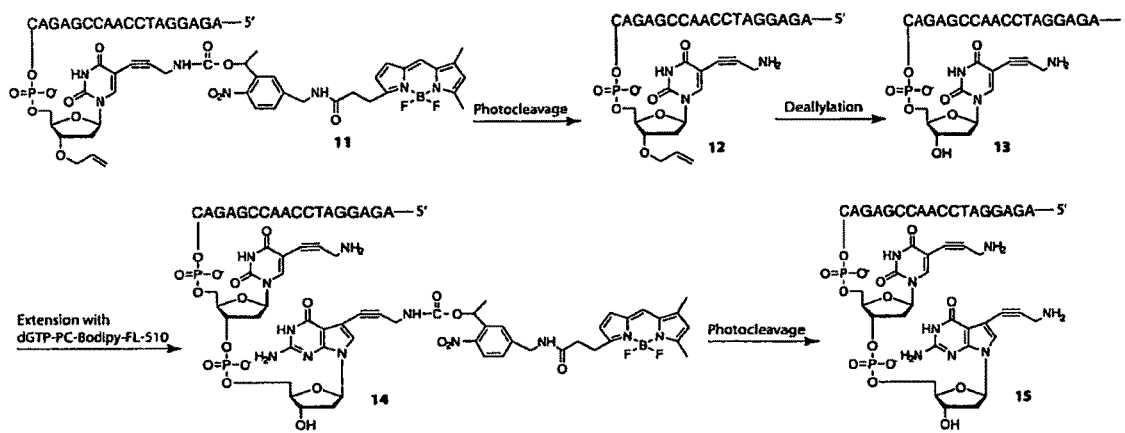
FIG. 4: One entire polymerase reaction cycle using 3'-O-allyl-dUTP-PC-Bodipy-FL-510 as a reversible terminator.

To evaluate the cleavage conditions of the allyl group capping the 3'-OH of DNA, first a 19-mer oligonucleotide [5'-AGAGGATCCAACCGAGAC-T(allyl)-3'] (SEQ ID NO:3) was synthesized using 3'-O-allyl-thymidine phosphoramidite (FIG. 3). The identity of the purified oligonucleotide was established using MALDI-TOF mass spectrometry. Then the above $Na_2PdCl_4$/TPPTS catalyst system was tested for the deallylation of the oligonucleotide. In FIG. 3A, the mass peak at m/z 5871 corresponds to the mass of the purified oligonucleotide bearing the allyl group. FIG. 3B shows a single mass peak at m/z 5831 indicating that near complete deallylation was achieved with a DNA/$Na_2PdCl_4$/TPPTS ratio of 1/55/440 in a reaction time of 30 seconds. The next step was to prove that the above deallylated DNA product could be used as a primer in a polymerase extension reaction. A single base extension reaction was performed using the deallylated DNA product as a primer, a synthetic template and a Biotin-11-ddGTP nucleotide terminator which was complementary to the base immediately adjacent to the priming site on the template. The DNA extension product was isolated using solid phase capture purification and analyzed using MALDI-TOF MS (25). The mass spectrum in FIG. 3C shows a clear peak at m/z 6535 corresponding to the extension product indicating that the deallylated product can be successfully used as a primer in a polymerase reaction.

The above experiments established that $Na_2PdCl_4$ and TPPTS could be used to efficiently carry out deallylation on DNA in an aqueous environment. Our next step was to investigate if a 3'-O-allyl-modified nucleotide could be incorporated in a DNA polymerase reaction. For this purpose, a nucleotide analogue 3'-O-allyl-thymidine triphosphate (3'-O-allyl-dTTP) was synthesized which was tested with 15 different polymerases for incorporation. The tested enzymes included Therminator, Thermo Sequenase, Vent (exo-), Deep Vent (exo-), Tth, Tfl, Bst, Pfu (exo-), Klenow (exo-) fragment and Sequenase DNA Polymerases, AMV, RAV2, M-MulV, HIV reverse transcriptases and a 9° N Polymerase (exo-) bearing the mutations A485L and Y409V. Our preliminary results showed that 9° N DNA polymerase (exo-) A485L/Y409V could efficiently incorporate 3'-O-allyl-dTTP in an extension reaction, consistent with results reported recently (31).

After confirming the incorporation ability of 3'-O-allyl-dTTP into a growing DNA strand by DNA polymerase, a new 3'-modified photocleavable fluorescent nucleotide analogue was synthesized, 3'-O-allyl-dUTP-PC-Bodipy-FL-510, according to FIG. 2, and it was established that the analogue can also can be efficiently incorporated by the above polymerase. The aim was to evaluate that the presence of the bulky photocleavable fluorescent moiety on the base and the allyl group on the 3' end of the nucleotide analogue would not affect the polymerase extension reaction. Furthermore, demonstration of an entire cycle of primer extension was desirable, photocleavage of the fluorophore, deallylation followed by extension with another photocleavable fluorescent nucleotide complementary to the next base on the template and photocleavage once again. This experiment will thus test the feasibility of using 3'-O-allyl-dUTP-PC-Bodipy-FL-510 as a reversible terminator for SBS.

Figure 5:
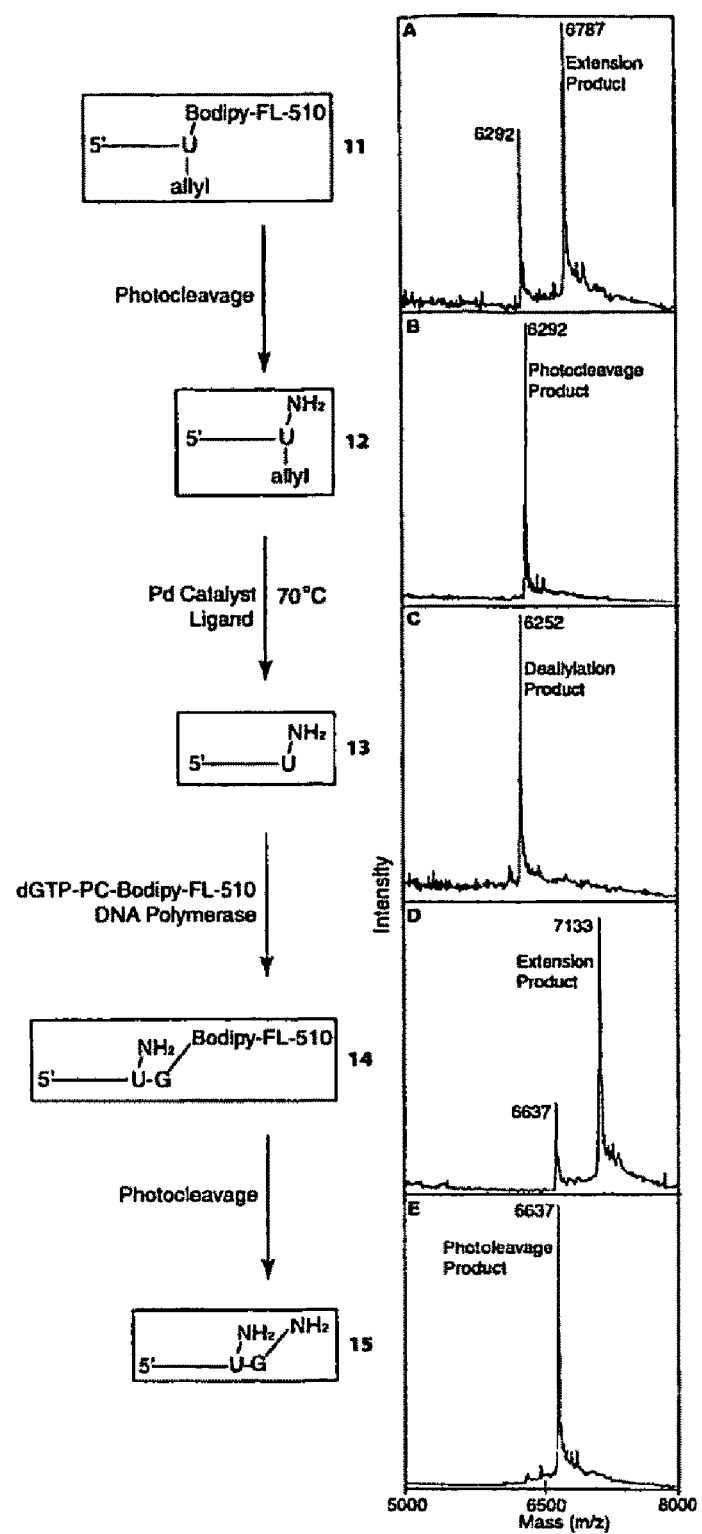
FIG. 5: MALDI-TOF MS results for each step of a polymerase reaction cycle using 3'-O-allyl-dUTP-PC-Bodipy-FL-510 as a reversible terminator. (A) Peak at m/z 6787 corresponding to the primer extension product 11 obtained using 3'-O-allyl-dUTP-PC-Bodipy-FL-510 and the 9° N Polymerase (exo-) A485L/Y409V. (B) Peak at m/z 6292 corresponding to the photocleavage product 12. (C) Peak at m/z 6252 corresponding to the photocleavage product without the allyl group 13 obtained after 90 secs of incubation with the catalyst and ligand at 70° C. (D) Peak at m/z 7133 corresponding to the extension product 14 from the purified deallylated product using dGTP-PC-Bodipy-FL-510 and Thermo Sequenase DNA Polymerase. (E) Peak at m/z 6637 corresponding to the photocleavage product 15.

The entire cycle of a polymerase reaction using 3'-O-allyl-dUTP-PC-Bodipy-FL-510 as a reversible terminator is depicted in FIG. 5. The extension product 11 obtained using 3'-O-allyl-dUTP-PC-Bodipy-FL-510 and 9° N DNA Polymerase (exo-) A485L/Y409V was purified using HPLC and analyzed using MALDI-TOF MS. The base in the template immediately adjacent to the priming site was 'A'. Thus, if 3'-O-allyl-dUTP-PC-Bodipy-FL-510 was accepted by the polymerase as a terminator, the primer would extend by one base and then the reaction would terminate. Our results indicate that this was indeed the case. After confirming that the extension reaction was successful, it was irradiated with near UV light at 355 nm for 10 seconds to cleave the fluorophore from the DNA, generating product 12. In an SBS system, this step would ensure that there would be no carryover of the fluorescence signal into the next incorporation cycle so as to prevent the generation of ambiguous data at each step, as shown in the accompanying paper (15). The photocleavage product 12 was then incubated with a $Na_2PdCl_4$/TPPTS catalyst system at 70° C. for 90 seconds to perform deallylation. The deallylated DNA product 13 was purified by reverse phase HPLC and then used as a primer in a second DNA extension reaction to prove that the regenerated 3'-OH was capable of allowing the polymerase reaction to continue. For the extension reaction, a photocleavable fluorescent nucleotide dGTP-PC-Bodipy-FL-510 was used and Thermo Sequenase DNA polymerase. The extension product 14 was irradiated as above, for 10 seconds to generate photocleavage product 15 and hence complete an entire reversible termination cycle.

After each step in the above cycle, a portion of the product was purified and analyzed using MALDI-TOF MS to confirm its identity and the successful completion of that step. Each product was desalted using the Zip Tip desalting protocol to ensure the generation of sharp and well-resolved data free from salt peaks. The MALDI-TOF MS data for each step are shown in FIG. 5. FIG. 5A shows the primer extension product 11 at m/z 6787 generated using 3'-O-allyl-dUTP-PC-Bodipy-FL-510. The peak at m/z 6292 corresponds to the photocleavage product that was generated by the partial photocleavage of the extension product due to the nitrogen laser ($\lambda$~337 nm) used for ionization of the analyte in MALDI-TOF MS. FIG. 5B shows the photocleavage result after the 10-second irradiation of the extension product at 355 nm. It can be seen from the data that the peak at m/z 6787, corresponding to the extension product has completely vanished and only a single peak corresponding to 12 remains at m/z 6292, which proves that photocleavage was efficiently achieved. FIG. 5C shows a similar single peak at m/z 6252, which corresponds to the deallylated photocleavage product 13. The absence of a significant peak at m/z 6292 proves that deallylation was completed with high efficiency. FIG. 5D shows the MALDI-TOF MS data for the extension product obtained using the above deallylated DNA product 13 as a primer and nucleotide analogue dGTP-PC-Bodipy-FL-510. A dominant peak is seen at m/z 7133 corresponding to the extension product 14. Finally, FIG. 5E shows a clear peak at m/z 6637 corresponding to the photocleavage product 15 and no significant peak at m/z 7133 indicating that complete photocleavage had occurred.

The results of the above experiments provide sufficient proof of the feasibility of using the allyl group as a reversible capping moiety for the 3'-OH of the photocleavable nucleotide analogues for SBS. It is shown that a 3'-O-allyl modified nucleotide bearing a photocleavable fluorophore is an excellent substrate for 9° N DNA polymerase A485L/Y409V and can be incorporated with high efficiency in a polymerase extension reaction. It is also demonstrated that complete photocleavage is achieved in ~10 seconds on these DNA products. Furthermore, it is shown that deallylation can be swiftly achieved to near completion under mild reaction conditions in an aqueous environment using a palladium catalyst. Finally, it is have established that the deallylated DNA product can be used as a primer to continue the polymerase reaction and that extension and photocleavage can be performed with high efficiency. These findings confirm that an allyl moiety protecting the 3'-OH group indeed bestows the capability of reversible terminating abilities to photocleavable nucleotide analogues, which can be used for SBS. Further efforts are being focused on generating four nucleotide analogues (A, C, G and T), each with a distinct photocleavable fluorophore and with a 3'-O-allyl capping group. These nucleotides will facilitate the development of SBS for high-throughput DNA sequencing and genotyping applications.

EXAMPLE 2

Synopsis

Figure 6:
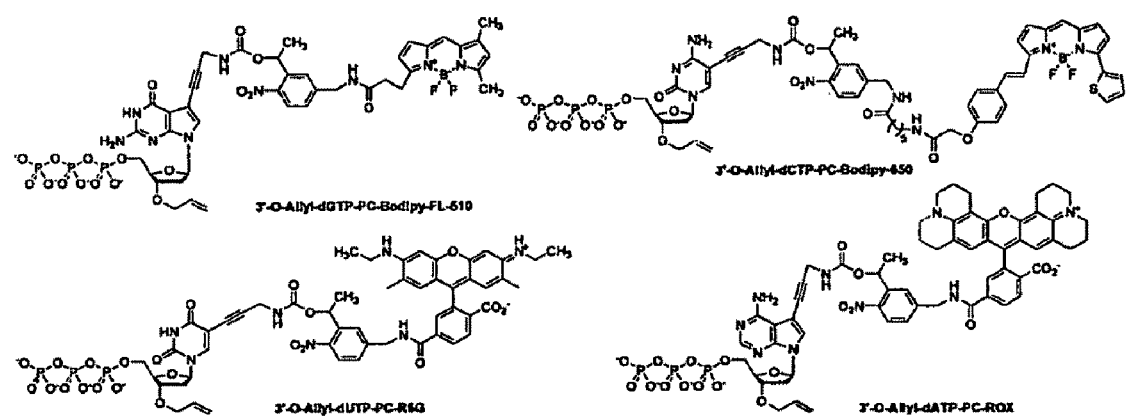
FIG. 6: Structures of four-color 3'-O-allyl modified photocleavable fluorescent nucleotides.

DNA sequencing by synthesis (SBS) using reversible fluorescent nucleotide terminators is a potentially efficient approach to address the limitations of current DNA sequencing techniques. Here, the design and synthesis of a complete set of four-color 3'-O-allyl modified photocleavable fluorescent nucleotides as reversible terminators for SBS is described. The nucleotides are efficiently incorporated by DNA polymerase into a growing DNA strand to terminate the polymerase reaction. After that the fluorophore is photocleaved quantitatively by irradiation at 355 nm, and the allyl group is rapidly and efficiently removed by using a Pd-catalyzed reaction under DNA compatible conditions to regenerate a free 3'-OH group to reinitiate the polymerase reaction. A homopolymeric region of a DNA template was successfully sequenced using these 3'-O-allyl modified nucleotide analogues, facilitating the development of SBS as a viable approach for high-throughput DNA sequencing Introduction The design and synthesis of a complete set of four-color 3'-O-allyl modified photocleavable fluorescent nucleotides, 3'-O-allyl-dGTP-PC-Bodipy-FL-510, 3'-O-allyl-dCTP-PC-Bodipy-650, 3'-O-allyl-dUTP-PC-R6G and 3'-O-allyl-dATP-PC-ROX, is disclosed here, as shown in FIG. 6. Their applications as reversible terminators for SBS are also described here, demonstrating the base-specific incorporation of these nucleotide analogues by DNA polymerase, the highly efficient photocleavage of the fluorescent dye, and the rapid and complete removal of 3'-O-allyl group in a Pd-catalyzed reaction under DNA compatible conditions. Previously, the Pd-catalyzed deallylation to regenerate a free 3'-OH of the DNA extension product was carried out in pure water (34) which can destabilize the primer-template duplex. A new condition for rapid quantitative deallylation in a buffer solution at pH 8.8 has been identified here, which is commonly used in a polymerase reaction. The successful synthesis of these 3'-O-allyl modified photocleavable fluorescent nucleotides as reversible terminators to sequence through a homopolymer sequence, and the identification of the new deallylation condition will facilitate the development of SBS as a viable approach for de novo DNA sequencing.

As an example, 3'-O-allyl-dGTP-PC-Bodipy-FL-510 (10) is used here to illustrate the detailed synthesis strategy and procedures. To the applicants' knowledge, using 3'-modified dGTP as a reversible terminator for SBS has not been reported, partly due to the difficulty of modifying 3'-OH of guanosine by a suitable capping group without protecting the guanine base. Structure 10 was prepared following a synthesis route as shown in FIG. 7.

2-amino-4-methoxy-7-(β-D-2-deoxyribofuranosyl)pyrrolo[2,3-d]-pyrimidine 1 was chosen as the starting material for the synthesis of 3'-O-allyl-dGTP 9 (FIG. 7) (see (35)). Structure 1 was first protected by isobutyryl chloride to form 2 quantitively (4). Structure 2 was iodinized with NIS to afford a single iodo product 3 in 84% yield, as the protected 2-amino group in the heterocyclic ring promotes the formation of 7-substituted product (5). Structure 3 was deprotected to afford 4 in 91% yield by sodium methoxide. The 5'-OH of 4 was protected by tert-butyldimethylsilyl chloride to yield 5 in 88% yield (6). The 3'-OH of 5 was subsequently allylated in $CH_2Cl_2$ and 40% aqueous NaOH solution using tetrabutylammonium bromide as phase-transfer catalyst to give a 92% yield of 6 without 2-N-allylated product. Cross-coupling reaction of 6 with the terminal alkyne catalyzed by Pd(0)/Cu (I) formed 7 in 94% yield (7). Next, a one-pot procedure of demethylation (8) and desilylation of 7 gave a moderate 34% yield of 8. Finally structure 8 was transformed into the corresponding triphosphate 9 following established procedures (9). Coupling 9 with PC-Bodipy-FL-510 NHS ester (2) yielded the target compound, 3'-O-allyl-dGTP-PC-Bodipy-FL-510, structure 10.

Figure 8:
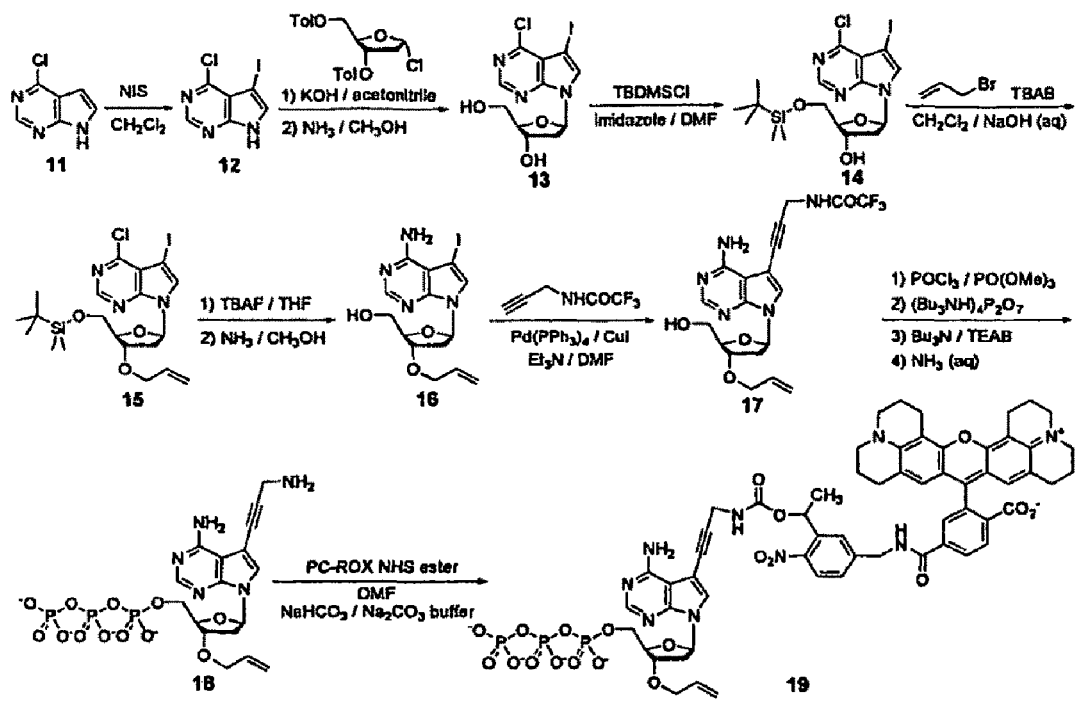
FIG. 8. Synthesis of 3'-O-allyl-dATP-PC-ROX 19.
Figure 9:
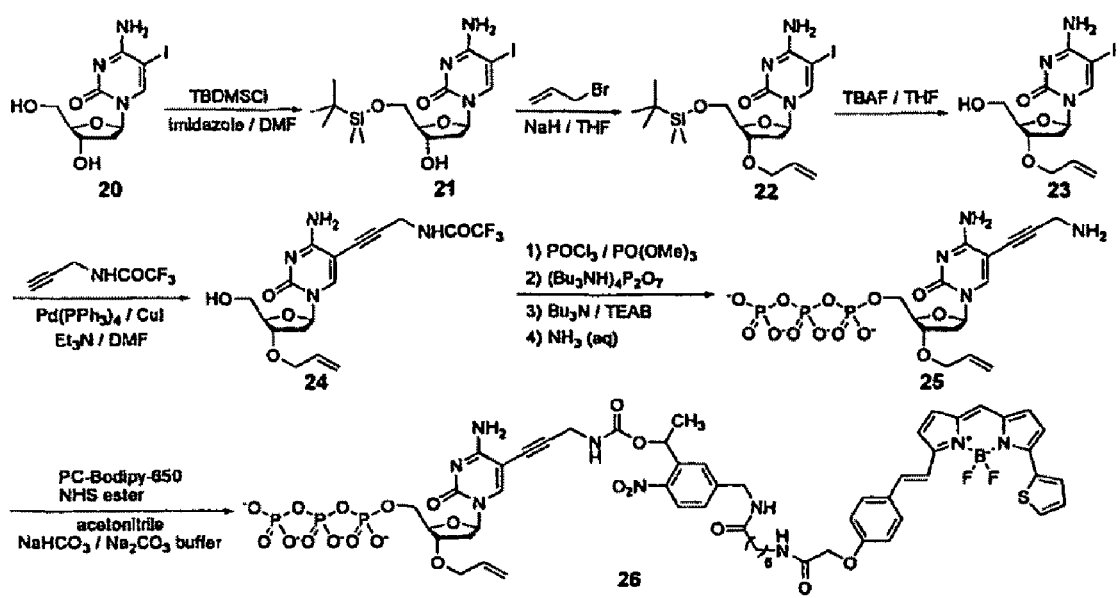
FIG. 9: Synthesis of 3'-O-allyl-dCTP-PC-Bodipy-650 26.
Figure 10:
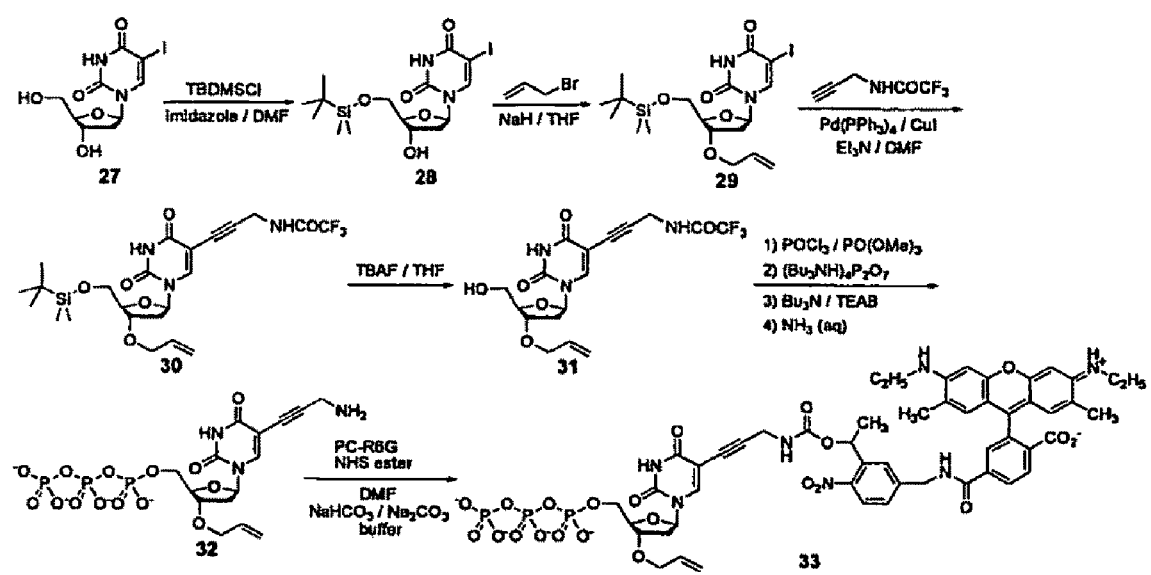
FIG. 10. Synthesis of 3'-O-allyl-dUTP-PC-R6G 33.

3'-O-allyl-dATP-PC-ROX 19 was also prepared, as were 3'-O-allyl-dCTP-PC-Bodipy-650 26 and 3'-O-allyl-dUTP-PC-R6G 33, as shown in FIGS. 8, 9, and 10, respectively.

For 3'-O-allyl modified PC fluorescent nucleotides to act as reversible terminators for SBS, it is important to establish that they can be used to determine a repeated DNA sequence in a polymerase reaction. To this end, polymerase DNA extension reactions were performed using these nucleotides as substrates in solution. This allows the isolation of the DNA product at each step of SBS for detailed molecular structure characterization by using MALDI-TOF mass spectrometry (MS).

Figure 11:
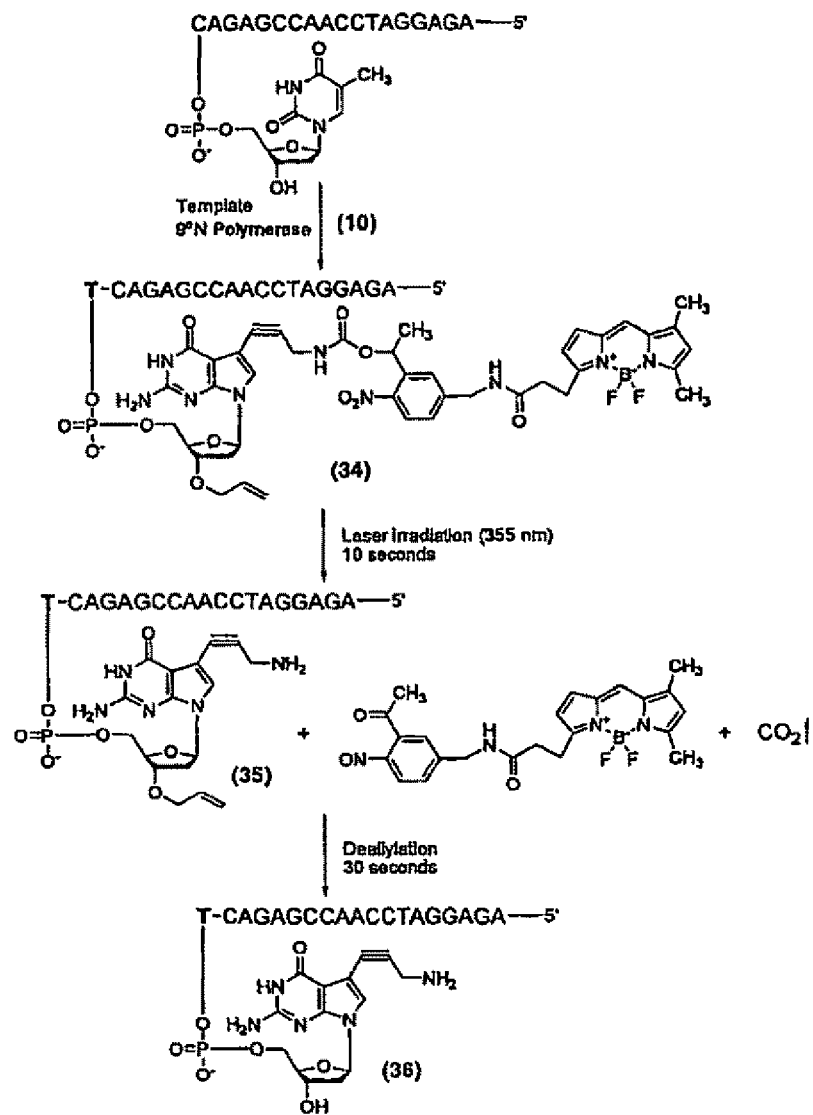
FIG. 11. Polymerase DNA extension reaction using 3'-O-allyl-dGTP-PC-Bodipy-FL-510 10 as a reversible terminator.

3'-O-allyl-dGTP-PC-Bodipy-FL-510 (structure 10) was used as a substrate in a DNA extension reaction as shown in FIG. 11. A synthetic 100-mer DNA corresponding to a portion of exon 7 of the human p53 gene was used as a template to perform the extension. The sequence in the template immediately adjacent to the annealing site of the primer had a repeating sequence of 3'-CC-5'. First, a polymerase extension reaction using 10 as a terminator along with a primer and the above template was performed. After the reaction, a small portion of the DNA extension product was characterized by MALDI-TOF MS. The rest of the product was irradiated at 355 nm for 10 sec to cleave the fluorophore from the DNA and then analyzed by MALDI-TOF MS. After photocleavage, the DNA product was added to a deallylation cocktail [1× Thermopol reaction buffer/$Na_2PdCl_4$/—$P(PhSO_3Na)_3$] to remove the 3'-Allyl group in 30 sec to yield quantitatively deallylated DNA product. The deallylated DNA product with a free 3'-OH group regenerated was then used as a primer to incorporate 10 in a subsequent second polymerase extension reaction.

Figure 12:
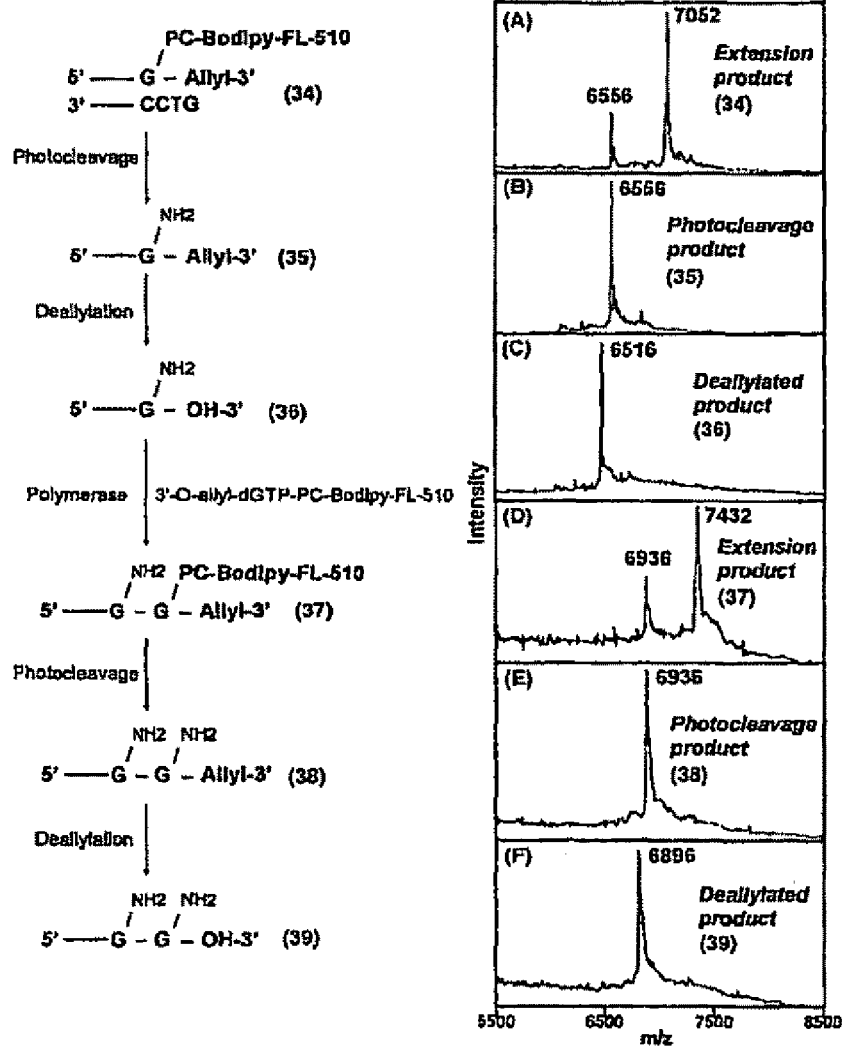
FIG. 12. A continuous polymerase extension using 10 as a reversible terminator (left) and MALDI-TOF MS spectra of consecutive extension photocleavage and deallylation products (right).

FIG. 12 (right panel) shows sequential mass spectrum at each step of DNA sequencing by synthesis using 10 as a reversible terminator. As can be seen from FIG. 12, panel (A), the MALDI-TOF MS spectrum consists of a distinct peak at m/z 7,052 corresponding to the single base DNA extension product 34 with 100% incorporation efficiency, confirming that the reversible terminator 10 can be incorporated base-specifically by DNA polymerase into a growing DNA strand. The small peak at m/z 6,556 corresponding to the photocleavage product is due to the partial cleavage caused by the nitrogen laser pulse (337 nm) used in MALDI ionization. FIG. 12, panel (B) shows the photocleavage result after 10 sec irradiation of the DNA extension product at 355 nm. The peak at m/z 7,052 has completely disappeared, whereas the peak corresponding to the photocleavage product 35 appears as the sole dominant peak at m/z 6,556. FIG. 12, panel (C) shows a single peak at m/z 6,516, which corresponds to a deallylated photocleavage product 36. The absence of a peak at m/z 6,556 proves that the deallylation reaction was completed with high efficiency. The next extension reaction was carried out by using this deallylated photocleavage product 36 as a primer along with 3'-O-allyl-dGTP-PC-Bodipy-FL-510 (10) to yield an extension product 37 (FIG. 12, panel D). DNA products (38 and 39) from photocleavage (FIG. 12, panel E) and deallylation (FIG. 12, panel F) respectively were obtained in similar manner as described previously, thereby completing two entire polymerase extension cycles to sequence a homopolymeric region of a template using 10 as a reversible terminator.

Figure 13:
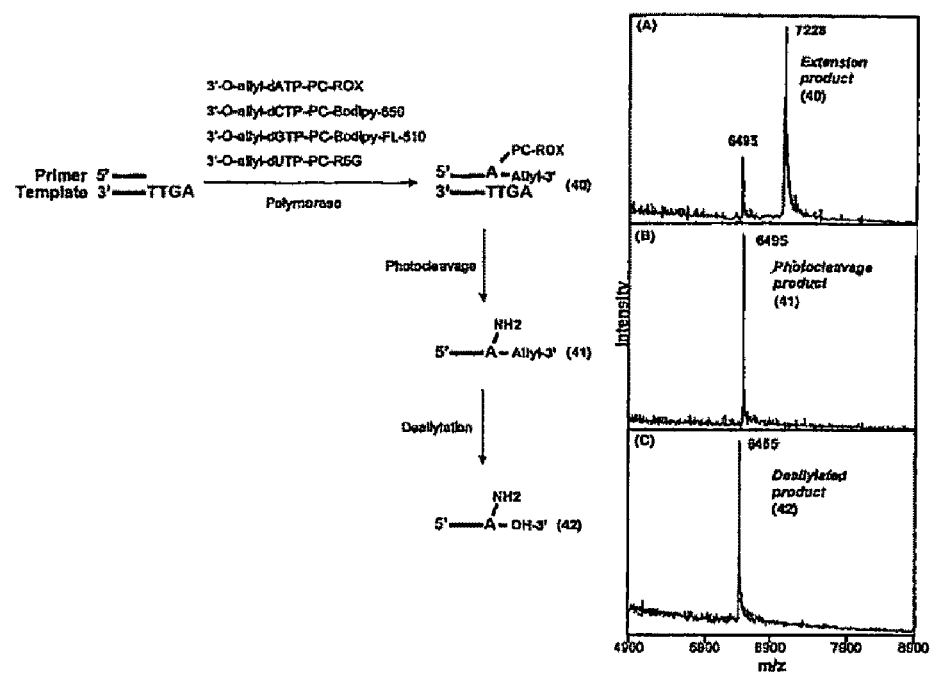
FIG. 13. (Left) Scheme showing 3'-O-allyl-dATP-PC-ROX 19 as a base specific reversible terminator for DNA primer extension, photocleavage and deallylation; (right) MALDI-TOF MS spectra for incorporation, photocleavage and deallylation products.

3'-O-allyl-dATP-PC-ROX 19, mixed together with 3'-O-allyl-dGTP-PC-Bodipy-FL-510 10/3'-O-allyl-dCTP-PC-Bodipy-650 26/3'-O-allyl-dUTP-PC-R6G 33, was used as a reversible terminator in a primer extension reaction as shown in FIG. 13 (left panel). After the incorporation, photocleavage and deallylation reactions were performed on the DNA extension product, following a similar procedure as for 10. FIG. 13 (right panel, A) shows the MOLDI-TOF MS results for the characterization of the product from each step. In the extension reaction, all four 3'-O-allyl modified photocleavable fluorescent nucleotides were added simultaneously instead of using only the correct one. The MS showed that only 3'-O-allyl-dATP-PC-ROX 19, the one complementary with the template sequence, was successfully incorporated in this extension reaction, as demonstrated by the single major peak at m/z 7,228 and a partial photocleavage peak at m/z 6,495. There is no other DNA extension product observed, indicating a faithful incorporation of the 3'-O-allyl modified nucleotide. The MS results also demonstrated that the photocleavage and deallylation steps were successfully conducted as shown in FIG. 13 (right panel, B and C) with peaks at m/z 6,495 and 6,455.

Figure 14:
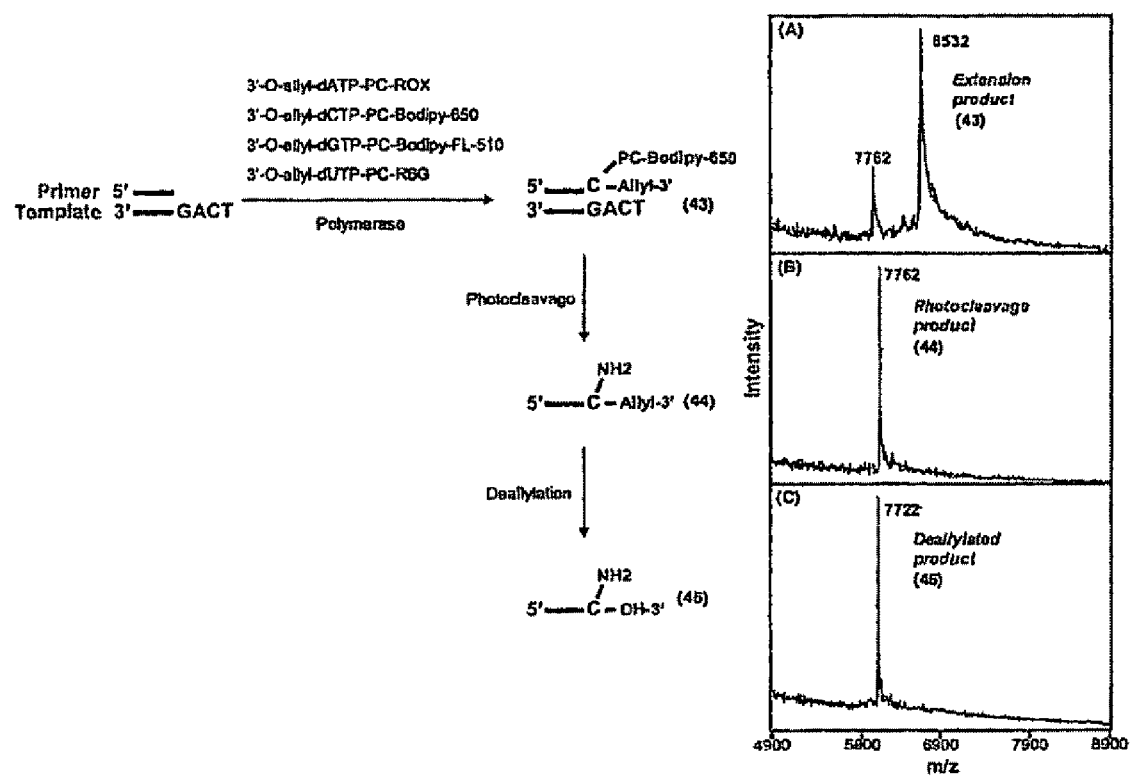
FIG. 14. (Left) Scheme showing 3'-O-allyl-dCTP-PC-Bodipy-650 26 as a base specific reversible terminator for DNA primer extension, photocleavage and deallylation; (right) MALDI-TOF MS spectra for incorporation, photocleavage and deallylation products.

3'-O-allyl-dCTP-PC-Bodipy-650 26, mixed together with 3'-O-allyl-dGTP-PC-Bodipy-FL-510 10/3'-O-allyl-dATP-PC-ROX 19/3'-O-allyl-dUTP-PC-R6G 33, was used in a primer extension reaction and then photocleavage and deallyation reactions were performed on the DNA extension product, as shown in FIG. 14 (left panel). FIG. 14 (right panel, A) shows the successful incorporation of 26, among the four nucleotide analogues, by the DNA polymerase to generate a single DNA extension product 43 at m/z 8,532. Subsequently, photocleavage was conducted to generate a photocleavage product 44 at m/z 7,762, and deallyation product 45 was observed at m/z 7,722, as shown in FIG. 14 (right panel, B and C), respectively.

Figure 15:
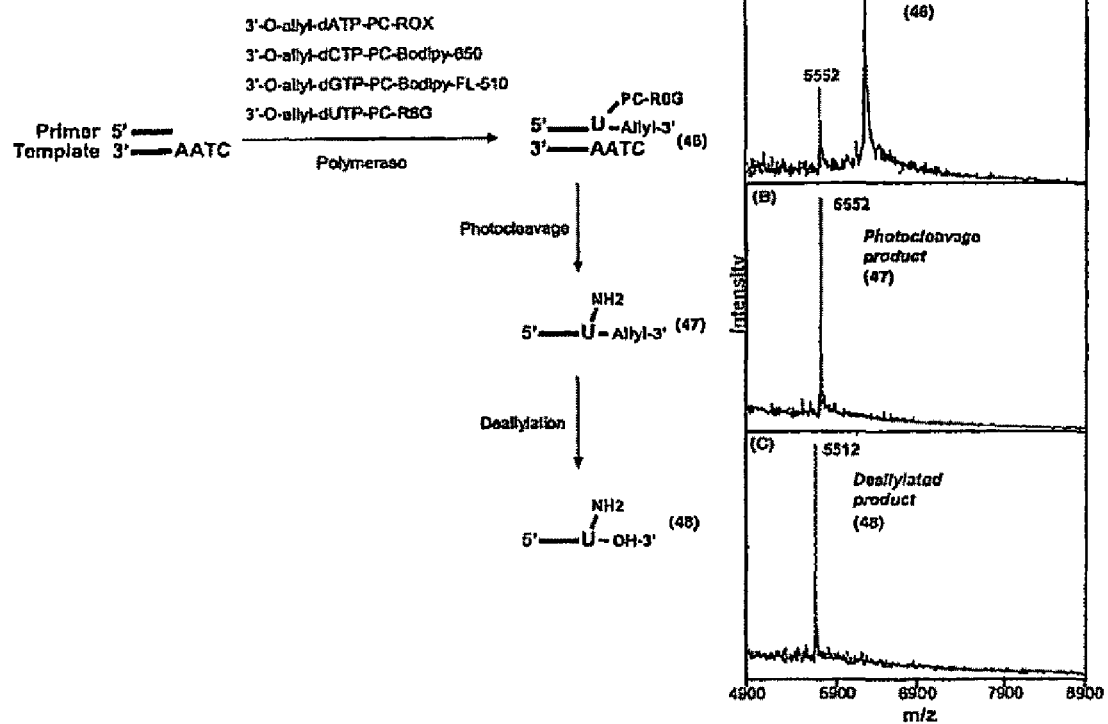
FIG. 15. (Left) Scheme showing 3'-O-allyl-dUTP-PC-R6G 33 as a base specific reversible terminator for DNA primer extension, photocleavage and deallylation; (right) MALDI-TOF MS spectra for incorporation, photocleavage and deallylation products.

Similarly, 3'-O-allyl-dUTP-PC-R6G 33, mixed together with 3'-O-allyl-dGTP-PC-Bodipy-FL-510 10/3'-O-allyl-dATP-PC-ROX 19/3'-O-allyl-dCTP-PC-Bodipy-650 26, also showed successful incorporation by a DNA polymerase in a primer extension reaction, as indicated by the single extension product (46) peak at m/z 6,210 in MALDI-TOF MS spectrum in FIG. 15 (right panel, A). The fluorescent dye was then photocleaved to generate a photocleavage product 47 at m/z 5,552, and 3'-O-allyl was removed in a Pd-catalyzed reaction to generate a deallylated product 48 at m/z 5,512, as shown in FIG. 15 (right panel, B and C), respectively.

Material and Methods

General Information $^1$H NMR spectra were recorded on Brucker DPX-400 (400 MHz) and Brucker DPX-300 spectrometers and are reported in ppm from CD$_3$OD or DMSO-d6 internal standard (3.31 or 2.50 ppm respectively). Data are reported as follows: (s=singlet, d=doublet, t=triplet, q=quartet, m=multiplet, dd=doublet of doublets, ddd=doublet of doublets of doublets; coupling constant(s) in Hz; integration; assignment). Proton decoupled $^{13}$C NMR spectra were recorded on a Brucker DPX-400 (100 MHz) spectrometer and are reported in ppm from CD$_3$OD, DMSO-d6, or CDCl$_3$ internal standard (49.0, 39.5, or 77.0 ppm respectively). Proton decoupled $^{31}$P NMR spectra were recorded on a Brucker DPX-300 (121.4 MHz) spectrometer without calibration. High Resolution Mass Spectra (HRMS) were obtained on a JEOL JMS HX 110A mass spectrometer. Mass measurement of DNA was made on a Voyager DE MALDI-TOF mass spectrometer (Applied Biosystems). Photolysis was performed by using a Spectra Physics GCR-150-30 Nd-yttrium/aluminum garnet laser that generates light pulses at 355 nm. Compounds 1 and 11 were purchased from Berry & Associates (Dexter, Mich.). Bodipy-FL-510 NHS ester, ROX NHS ester, Bodipy-650 NHS ester and R6G NHS ester were purchased from Invitrogen (Carlsbad, Calif.). All other chemicals were purchased from Sigma-Aldrich. 9° N polymerase (exo-). A485L/Y409V was generously provided by New England Biolabs.

I. Synthesis of 3'-O-allyl Modified Photocleavable Fluorescent Nucleotides

1) Synthesis of 3'-O-allyl-dGTP-PC-Bodipy-FL-510 as Shown in FIG. 7

2-(2-Methylpropanoyl)amino-7-[3',5'-bis-O-(2-methylpropanoyl)-β-D-2'-deoxyribofuranosyl]-4-methoxypyrrolo[2,3-d]pyrimidine (2): To a stirred suspension of 1 (1.00 g; 3.57 mmol) in anhydrous pyridine (35 mL) was added slowly isobutyryl chloride (3.40 mL; 32.2 mmol) at 0° C. The reaction mixture was stirred at 0° C. for 1 h. Methanol (2 mL) was then added and the reaction mixture was stirred for another 10 min. Then most solvent was removed under vacuum. Ethyl acetate (200 mL) and saturated aqueous NaHCO$_3$ (50 mL) were added to the residue. The organic layer was separated and washed by saturated aqueous NaHCO$_3$ and NaCl respectively, and dried over anhydrous Na$_2$SO$_4$. After evaporation of the solvent, the residue was purified by flash column chromatography over silica gel using ethyl acetate-hexane (1:3~2) as the eluent to afford 2 as white foam (1.75 g; 99% yield): $^1$H NMR (400 MHz, CD$_3$OD) δ 7.28 (d, J=3.7 Hz, 1H, 6-H), 6.66 (dd, J=5.9, 8.6 Hz, 1H, 1'-H), 6.51 (d, J=3.7 Hz, 1H, 5-H), 5.41 (m, 1H, 3'-H), 4.33-4.36 (m, 2H, 5'-H), 4.22 (m, 1H, 4'-H), 4.08 (s, 3H, 4-OCH$_3$), 2.83-2.96 (m, 2H, one of CH(CH$_3$)$_2$ and one of 2'-H), 2.54-2.70 (m, 2H, two of CH(CH$_3$)$_2$), 2.48-2.54 (ddd, J=2.0, 5.9, 14.2 Hz, one of 2'-H), 1.15-1.23 (m, 18H, CH(CH$_3$)$_2$); $^{13}$C NMR (100 MHz, CD$_3$OD) δ 178.2, 177.7, 177.4, 164.2, 153.4, 152.5, 123.4, 103.5, 100.7, 85.2, 83.0, 75.9, 65.0, 54.4, 37.9, 36.6, 35.0, 34.9, 19.9 (two CH$_3$), 19.3-19.4 (four peaks for four CH$_3$); HRMS (FAB+) calcd for C$_{24}$H$_{35}$O$_7$N$_4$ (M+H$^+$): 491.2506. Found: 491.2503.

2-(2-Methylpropanoyl)amino-7-[3',5'-bis-O-(2-methylpropanoyl)-β-D-2'-deoxyribo-furanosyl]-5-iodo-4-methoxypyrrolo[2,3-d]pyrimidine (3): To a vigorously stirred solution of 2 (1.75 g; 3.57 mmol) in anhydrous DMF (27 mL) was added 95% N-iodosuccimide (NIS) (866 mg; 3.66 mmol). The reaction mixture was stirred at room temperature for 22 h, and then most solvent was removed under vacuum. Diethyl ether (200 mL) and saturated aqueous NaHCO$_3$ (50 mL) were added. The organic layer was separated and washed by saturated aqueous NaCl, and dried over anhydrous Na$_2$SO$_4$. After evaporation of the solvent, the residue was purified by flash column chromatography over silica gel using ethyl acetate-hexane (1:3) as the eluent to afford 3 as white solid (1.98 g; 90% yield): $^1$H NMR (400 MHz, CD$_3$OD) δ 7.43 (s, 1H, 6-H), 6.63 (dd, J=6.0, 8.2 Hz, 1H, 1'-H), 5.41 (m, 1H, 3'-H), 4.33-4.36 (m, 2H, 5'-H), 4.23 (m, 1H, 4'-H), 4.09 (s, 3H, 4-OCH$_3$), 2.78-2.94 (m, 2H, one of CH(CH$_3$)$_2$ and one of 2'-H), 2.57-2.70 (m, 2H, two of CH(CH$_3$)$_2$), 2.50-2.57

(ddd, J=2.3, 6.0, 14.2 Hz, one of 2'-H), 1.17-1.24 (m, 18H, CH(CH$_3$)$_2$); $^{13}$C NMR (100 MHz, CD$_3$OD) δ 178.3, 177.8, 177.5, 164.3, 153.3, 152.8, 128.6, 105.2, 85.3, 83.3, 75.8, 65.0, 54.4, 51.8, 38.2, 36.8, 35.2, 35.1, 19.9 (two CH$_3$), 19.3-19.5 (four peaks for four CH$_3$); HRMS (FAB+) calcd for C$_{24}$H$_{34}$O$_7$N$_4$I (M+H$^+$): 617.1472. Found: 617.1464.

2-Amino-7-(β-D-2'-deoxyribofuranosyl)-5-iodo-4-methoxypyrrolo[2,3-d]pyrimidine (4): 3 (1.98 g; 3.21 mmol) was dissolved in 0.5 M methanolic CH$_3$ONa (50 mL) and stirred at 65° C. for 12 h. Saturated aqueous NaHCO$_3$ (20 mL) was added and the mixture was stirred for 10 min. Then most of methanol was evaporated and the residue was extracted by ethyl acetate (150 mL). The organic layer was washed by saturated aqueous NaHCO$_3$ and NaCl respectively, and dried over anhydrous Na$_2$SO$_4$. After evaporation of the solvent, the residue was purified by flash column chromatography over silica gel using CH$_3$OH—CH$_2$Cl$_2$ (1:30~15) as the eluent to afford 4 as white solid (1.23 g; 94% yield): $^1$H NMR (400 MHz, CD$_3$OD) δ 7.17 (s, 1H, 6-H), 6.36 (dd, J=6.0, 8.4 Hz, 1H, 1'-H), 4.47 (m, 1H, 3'-H), 3.99 (s, 3H, 4-OCH$_3$), 3.96 (m, 1H, 4'-H), 3.77 (dd, J=3.4, 12.0 Hz, 1H, one of 5'-H), 3.70 (dd, J=3.7, 12.0 Hz, 1H, one of 5'-H), 2.55-2.64 (ddd, J=6.0, 8.4, 13.4 Hz, one of 2'-H), 2.20-2.26 (ddd, J=2.4, 5.9, 13.4 Hz, one of 2'-H); $^{13}$C NMR (100 MHz, CD$_3$OD) δ 164.7, 160.6, 154.3, 126.5, 101.6, 88.7, 86.0, 73.0, 63.7, 53.7, 51.3, 41.1; HRMS (FAB+) calcd for C$_{12}$H$_{16}$O$_4$N$_4$I (M+H$^+$): 407.0216. Found: 407.0213.

2-Amino-7-[β-D-5'-O-(tert-butyldimethylsilyl)-2'-deoxyribofuranosyl]-5-iodo-4-methoxypyrrolo[2,3-d]pyrimidine (5): To a stirred solution of 4 (1.23 g; 3.02 mmol) and imidazole (494 mg; 7.24 mmol) in anhydrous DMF (15 mL) was added tert-butyldimethylsilyl chloride (TBDMSCl) (545 mg; 3.51 mmol). The reaction mixture was stirred at room temperature for 20 h. Then most solvent was removed under vacuum, and the residue was purified by flash column chromatography over silica gel using ethyl acetate-hexane (1:2~0.5) as the eluent to afford 5 as white foam (1.38 g; 88% yield): $^1$H NMR (400 MHz, CD$_3$OD) δ 7.23 (s, 1H, 6-H), 6.49 (dd, J=6.1, 7.7 Hz, 1H, 1'-H), 4.46 (m, 1H, 3'-H), 3.99 (s, 3H, 4-OCH$_3$), 3.94 (m, 1H, 4'-H), 3.79-3.87 (m, 2H, 5'-H), 2.36-2.44 (ddd, J=5.8, 7.7, 13.3 Hz, one of 2'-H), 2.24-2.31 (ddd, J=3.1, 6.0, 13.3 Hz, one of 2'-H), 0.96 (s, 9H, C(CH$_3$)$_3$), 0.14 (s, 3H, one of SiCH$_3$), 0.13 (s, 3H, one of SiCH$_3$); $^{13}$C NMR (100 MHz, CD$_3$OD) δ 164.6, 160.7, 154.7, 125.1, 101.0, 88.2, 84.2, 72.7, 64.7, 53.7, 51.7, 41.9, 26.7, 19.4, −5.0, −5.1; HRMS (FAB+) calcd for C$_{18}$H$_{30}$O$_4$N$_4$SiI (M+H$^+$): 521.1081. Found: 521.1068.

7-[β-D-3'-O-Allyl-5'-O-(tert-butyldimethylsilyl)-2'-deoxyribofuranosyl]-2-amino-5-iodo-4-methoxypyrrolo[2,3-d]pyrimidine (6): To a stirred solution of 5 (1.38 g; 2.66 mmol) in CH$_2$Cl$_2$ (80 mL) were added tetrabutylammonium bromide (TBAB) (437 mg; 1.33 mmol), allyl bromide (1.85 mL, 21.4 mmol) and 40% aqueous NaOH solution (40 mL). The reaction mixture was stirred at room temperature for 1 h. Ethyl acetate (200 mL) was added and the organic layer was separated. The aqueous layer was extracted with ethyl acetate (2×50 mL). The combined organic layer was washed by saturated aqueous NaHCO$_3$ and NaCl respectively, and dried over anhydrous Na$_2$SO$_4$. After evaporation of the solvent, the residue was purified by flash column chromatography over silica gel using ethyl acetate-hexane (1:3) as the eluent to afford 6 as white solid (1.37 g; 92% yield): $^1$H NMR (400 MHz, CD$_3$OD) δ 7.20 (s, 1H, 6-H), 6.43 (dd, J=6.2, 7.9 Hz, 1H, 1'-H), 5.89-5.99 (m, 1H, CH$_2$C=CH$_2$), 5.29-5.35 (dm, J=17.3 Hz, 1H, one of CH$_2$CH=CH$_2$), 5.16-5.21 (dm, J=10.5 Hz, 1H, one of CH$_2$CH=CH$_2$), 4.24 (m, 1H, 3'-H), 4.01-4.11 (m, 3H, 4'-H and CH$_2$CH=CH$_2$), 3.99 (s, 3H, 4-OCH$_3$), 3.76-3.84 (m, 2H, 5'-H), 2.32-2.44 (m, 2H, 2'-H), 0.95 (s, 9H, C(CH$_3$)$_3$), 0.14 (s, 3H, one of SiCH$_3$), 0.13 (s, 3H, one of SiCH$_3$); $^{13}$C NMR (100 MHz, CDCl$_3$) δ 163.3, 158.6, 153.6, 134.1, 123.7, 116.9, 100.6, 84.4, 83.0, 79.1, 70.0, 63.6, 53.3, 51.1, 38.1, 26.1, 18.5, −5.1, −5.3; HRMS (FAB+) calcd for C$_{21}$H$_{34}$O$_4$N$_4$SiI (M+H$^+$): 561.1394. Found: 561.1390.

7-[β-D-3'-O-Allyl-5'-O-(tert-butyldimethylsilyl)-2'-deoxyribofuranosyl]-2-amino-5-[3-[(trifluoroacetyl)amino]-prop-1-ynyl]-4-methoxypyrrolo[2,3-d]pyrimidine (7): To a stirred solution of 6 (1.37 g; 2.45 mmol) in anhydrous DMF (11 mL) were added tetrakis(triphenylphosphine)palladium (0) (286 mg; 0.245 mmol) and CuI (101 mg; 0.532 mmol). The solution was stirred at room temperature for 10 min. Then N-propargyltrifluoroacetamide (1.12 g; 7.43 mmol) and triethylamine (0.68 mL; 4.90 mmol) were added. The reaction was stirred at room temperature for 13 h with exclusion of air and light. Most DMF was removed under vacuum and the residue was dissolved in ethyl acetate (100 mL). The solution was washed by saturated aqueous NaHCO$_3$ and NaCl respectively, and dried over anhydrous Na$_2$SO$_4$. After evaporation of the solvent, the residue was purified by flash column chromatography over silica gel using ethyl acetate-hexane (1:3~1.5) and CH$_3$OH—CH$_2$Cl$_2$ (1:30) respectively as the eluent to afford 7 as yellow solid (1.34 g; 94% yield): $^1$H NMR (400 MHz, CD$_3$OD) δ 7.34 (s, 1H, 6-H), 6.42 (dd, J=6.2, 7.7 Hz, 1H, 1'-H), 5.88-5.99 (m, 1H, CH$_2$CH=CH$_2$), 5.28-5.35 (dm, J=17.3 Hz, 1H, one of CH$_2$CH=CH$_2$), 5.16-5.21 (dm, J=10.5 Hz, 1H, one of CH$_2$CH=CH$_2$), 4.29 (s, 2H, C≡CCH$_2$), 4.24 (m, 1H, 3'-H), 4.00-4.09 (m, 3H, 4'-H and CH$_2$CH=CH$_2$), 3.98 (s, 3H, 4-OCH$_3$), 3.76-3.84 (m, 2H, 5'-H), 2.32-2.45 (m, 2H, 2'-H), 0.94 (s, 9H, C(CH$_3$)$_3$), 0.12 (s, 3H, one of SiCH$_3$), 0.11 (s, 3H, one of SiCH$_3$); $^{13}$C NMR (100 MHz, CD$_3$OD) δ 165.0, 161.2, 158.1 (q, J=36 Hz, COCF$_3$), 154.2, 135.6, 125.0, 117.2 (q, J=284 Hz, COCF$_3$), 117.0, 99.2, 97.3, 86.0, 84.6, 84.5, 80.3, 78.0, 71.0, 64.8, 53.8, 39.0, 30.9, 26.5, 19.3, −5.1, −5.2; HRMS (FAB+) calculated for C$_{26}$H$_{37}$O$_5$N$_5$F$_3$Si (M+H$^+$): 584.2516. Found: 584.2491.

3'-O-Allyl-7-deaza-7-[3-[(trifluoroacetyl)amino]-prop-1-ynyl]-2'-deoxyguanosine (8): To a stirred solution of 7 (1.34 g; 2.30 mmol) in anhydrous CH$_3$CN (86 mL) were added NaI (363 mg; 2.42 mmol) and chlorotrimethylsilane (TMSCl) (0.306 mL; 2.42 mmol). The reaction was stirred at room temperature for 1 h and then at 50° C. for 12 h. The solvent was evaporated and the residue was dissolved in anhydrous THF (76 mL). 1 M tetrabutylammonium fluoride (TBAF) in THF solution (4.80 mL; 4.80 mmol) was added and the reaction was stirred at room temperature for 1 h. The solvent was evaporated and the residue was dissolved in ethyl acetate (150 mL). The solution was washed by saturated aqueous NaCl and dried over anhydrous Na$_2$SO$_4$. After evaporation of the solvent, the residue was purified by flash column chromatography over silica gel using CH$_3$OH-ethyl acetate (1:30) as the eluent to afford 8 as yellow solid (356 mg; 34% yield): $^1$H NMR (400 MHz, CD$_3$OD) δ 7.21 (s, 1H, 6-H), 6.30 (dd, J=6.0, 8.4 Hz, 1H, 1'-H), 5.88-5.99 (m, 1H, CH$_2$CH=CH$_2$), 5.28-5.35 (dm, J=17.3 Hz, 1H, one of CH$_2$CH=CH$_2$), 5.15-5.20 (dm, J=10.5 Hz, 1H, one of CH$_2$CH=CH$_2$), 4.29 (s, 2H, C≡CCH$_2$), 4.23 (m, 1H, 3'-H), 4.00-4.10 (m, 3H, 4'-H and CH$_2$CH=CH$_2$), 3.65-3.75 (m, 2H, 5'-H), 2.41-2.49 (ddd, J=5.8, 8.4, 13.6 Hz, 1H, one of 2'-H), 2.34-2.40 (ddd, J=2.3, 6.0, 13.6 Hz, 1H, one of 2'-H); $^{13}$C NMR (100 MHz, CD$_3$OD) δ 160.9, 158.0 (q, J=36 Hz, COCF$_3$), 154.1, 151.8, 135.6, 124.4, 117.2 (q, J=284 Hz, COCF$_3$), 117.0, 101.4, 99.7, 86.4, 85.5, 84.8, 80.7, 78.0, 71.0, 63.7, 38.5, 31.2; HRMS (FAB+) calcd for C$_{19}$H$_{21}$O$_5$N$_5$F$_3$ (M+H$^+$): 456.1495. Found: 456.1493.

3'-O-Allyl-7-deaza-7-(3-aminoprop-1-ynyl)-2'-deoxyguanosine-5'-triphosphate (9): The procedure is the same as that of preparing 3'-O-allyl-5-(3-aminoprop-1-ynyl)-2'-deoxyuridine-5'-triphosphate in Ref. 34a to yield 9 as colorless syrup: $^1$H NMR (300 MHz, D$_2$O) δ 7.56 (s, 1H, 6-H), 6.37 (t, J=7.3 Hz, 1H, 1'-H), 5.89-6.02 (m, 1H, CH$_2$CH═CH$_2$), 5.31-5.39 (dm, J=17.3 Hz, 1H, one of CH$_2$CH═CH$_2$), 5.21-5.28 (dm, J=10.5 Hz, 1H, one of CH$_2$CH═CH$_2$), 4.49 (s, 2H, C≡CCH$_2$), 4.32 (m, 1H, 3'-H), 4.06-4.18 (m, 3H, 4'-H and CH$_2$CH═CH$_2$), 3.92-3.99 (m, 2H, 5'-H), 2.44-2.60 (m, 2H, 2'-H); $^{31}$P NMR (121.4 MHz, D$_2$O) δ −6.1 (d, J=20.8 Hz, 1P, γ-P), −10.8 (d, J=18.9 Hz, 1P, α-P), −21.9 (t, J=19.8 Hz, 1P, β-P).

3'-O-Allyl-dGTP-PC-Bodipy-FL-510 (10): PC-Bodipy-FL-510 NHS ester (prepared by the same procedure in Ref. 34a) (7.2 mg, 12 μmol) in 300 μL of acetonitrile was added to a solution of 9 (2 mg, 3.4 μmol) in 300 μL of Na$_2$CO$_3$—NaHCO$_3$ aqueous buffer (0.1 M, pH 8.5). The reaction mixture was stirred at room temperature for 3 h. A preparative silica-gel TLC plate was used to separate the unreacted PC-Bodipy-FL-510 NHS ester from the fraction containing 10 with CHCl$_3$—CH$_3$OH (85:15) as the eluent. The product was concentrated further under vacuum and purified with reverse-phase HPLC on a 150×4.6-mm C18 column to obtain the pure product 10 (retention time of 34 min). Mobile phase: A, 8.6 mM triethylamine/100 mM hexafluoroisopropyl alcohol in water (pH 8.1); B, methanol. Elution was performed with 100% A isocratic over 10 min, followed by a linear gradient of 0-50% B for 20 min and then 50% B isocratic over another 20 min. 3'-O-allyl-dGTP-PC-Bodipy-FL-510 10 was characterized by primer extension reaction and MALDI-TOF MS.

2) Synthesis of 3'-O-Allyl-dATP-PC-ROX as Shown in FIG. 8

4-Chloro-5-iodopyrrolo[2,3-d]pyrimidine (12): To a vigorously stirred solution of 11 (1.0 g; 6.51 mmol) in CH$_2$Cl$_2$ (55 mL) was added 95% N-iodosuccimide (1.70 g; 7.18 mmol). The reaction mixture was stirred at room temperature for 1 h, during which time more precipitate appeared. The solid was filtered and recrystallized in hot methanol to afford 12 as slightly grey crystals (1.49 g; 82% yield): $^1$H NMR (400 MHz, DMSO-d6) δ 12.96 (s br, 1H, NH), 8.59 (s, 1H, 2-H), 7.94 (s, 1H, 6-H); $^{13}$C NMR (100 MHz, DMSO-d6) δ 151.2, 150.4, 150.2, 133.6, 115.5, 51.7; HRMS (FAB+) calcd for C$_6$H$_4$N$_3$ClI (M+H$^+$): 279.9139. Found: 279.9141.

4-Chloro-7-(β-D-2'-deoxyribofuranosyl)-5-iodopyrrolo[2,3-d]pyrimidine (13): To a stirred solution of 12 (597 mg; 2.14 mmol) in CH$_3$CN (36 mL) were added KOH powder (0.30 g; 5.36 mmol) and tris[2-(2-methoxyethoxy)ethyl]amine (44 μL, 0.14 mmol). The mixture was stirred at room temperature for 10 min and then 90% 3,5-di-O-(p-toluyl)-2-deoxy-D-ribofuranosyl chloride (1.00 g; 2.31 mmol) was added. The reaction was stirred vigorously at room temperature for 1 h, and the insoluble material was filtered and washed by hot acetone. The combined solution was evaporated and dissolved in 7M methanolic ammonia (72 mL). The solution was stirred at room temperature for 24 h. After evaporation of the solvent, the residue was purified by flash column chromatography over silica gel using CH$_3$OH—CH$_2$Cl$_2$ (0-1:20) as the eluent to afford 13 as white solid (711 mg; 84% yield): $^1$H NMR (400 MHz, CD$_3$OD) δ 8.57 (s, 1H, 2-H), 8.08 (s, 1H, 6-H), 6.72 (dd, J=6.3, 7.5 Hz, 1H, 1'-H), 4.53 (m, 1H, 3'-H), 4.00 (m, 1H, 4'-H), 3.80 (dd, J=3.6, 12.0 Hz, 1H, one of 5'-H), 3.74 (dd, J=3.6, 12.0 Hz, 1H, one of 5'-H), 2.56-2.64 (ddd, J=6.1, 7.5, 13.5 Hz, 1H, one of 2'-H), 2.36-2.43 (ddd, J=3.3, 6.2, 13.5 Hz, 1H, one of 2'-H); $^{13}$C NMR (100 MHz, CD$_3$OD) δ 152.9, 151.7, 151.3, 134.7, 118.5, 89.0, 85.7, 72.6, 63.2, 52.6, 41.7; HRMS (FAB+) calcd for C$_{11}$H$_{12}$O$_3$N$_3$ClI (M+H$^+$): 395.9612. Found: 395.9607.

7-[β-D-5'-O-(tert-Butyldimethylsilyl)-2'-deoxyribofuranosyl]-4-chloro-5-iodopyrro-lo[2,3-d]pyrimidine (14): The procedure is the same as that of 5 and the crude was purified by flash column chromatography over silica gel using ethyl acetate-hexane (1:3~2) as the eluent to afford 14 as white solid (65% yield) and 30% of the starting material 13: $^1$H NMR (400 MHz, CD$_3$OD) δ 8.56 (s, 1H, 2-H), 7.99 (s, 1H, 6-H), 6.73 (t, J=6.7 Hz, 1H, 1'-H), 4.52 (m, 1H, 3'-H), 4.02 (m, 1H, 4'-H), 3.92 (dd, J=3.0, 11.4 Hz, 1H, one of 5'-H), 3.86 (dd, J=3.1, 11.4 Hz, 1H, one of 5'-H), 2.47-2.55 (ddd, J=5.8, 7.1, 13.4 Hz, 1H, one of 2'-H), 2.40-2.47 (ddd, J=3.6, 6.3, 13.4 Hz, 1H, one of 2'-H), 0.94 (s, 9H, C(CH$_3$)$_3$), 0.14 (s, 3H, one of SiCH$_3$), 0.13 (s, 3H, one of SiCH$_3$); $^{13}$C NMR (100 MHz, CD$_3$OD) δ 152.8, 151.5, 151.3, 133.8, 118.2, 88.9, 85.4, 72.5, 64.6, 52.6, 42.4, 26.7, 19.5, −4.9, −5.0; HRMS (FAB+) calcd for C$_{17}$H$_{26}$O$_3$N$_3$ClSiI (M+H$^+$): 510.0477. Found: 510.0487.

7-[β-D-3'-O-Allyl-5'-O-(tert-butyldimethylsilyl)-2'-deoxyribofuranosyl]-4-chloro-5-iodopyrrolo[2,3-d]pyrimidine (15): The procedure is the same as that of 6 and the crude was purified by flash column chromatography over silica gel using ethyl acetate-hexane (1:6) as the eluent to afford 15 as yellow oil (752 mg; 95% yield): $^1$H NMR (400 MHz, CD$_3$OD) δ 8.52 (s, 1H, 2-H), 7.94 (s, 1H, 6-H), 6.64 (dd, J=6.1, 7.6 Hz, 1H, 1'-H), 5.88-5.99 (m, 1H, CH$_2$CH═CH$_2$), 5.28-5.34 (dm, J'17.3 Hz, 1H, one of CH$_2$CH═CH$_2$), 5.16-5.21 (dm, J=10.4 Hz, 1H, one of CH$_2$CH═CH$_2$), 4.28 (m, 1H, 3'-H), 4.13 (m, 1H, 4'-H), 4.01-4.11 (m, 2H, CH$_2$CH═CH$_2$), 3.88 (dd, J=3.6, 11.2 Hz, 1H, one of 5'-H), 3.80 (dd, J=3.1, 11.3 Hz, 1H, one of 5'-H), 2.51-2.57 (ddd, J=2.7, 6.0, 13.5 Hz, 1H, one of 2'-H), 2.42-2.50 (ddd, J=5.7, 7.7, 13.5 Hz, 1H, one of 2'-H), 0.93 (s, 9H, C(CH$_3$)$_3$), 0.13 (s, 3H, one of SiCH$_3$), 0.12 (s, 3H, one of SiCH$_3$); $^{13}$C NMR (100 MHz, CD$_3$OD) δ 152.8, 151.4, 151.3, 135.5, 133.6, 118.2, 117.2, 86.5, 85.6, 80.2, 71.0, 64.8, 52.8, 39.7, 26.7, 19.4, −4.8, −5.0; HRMS (FAB+) calcd for C$_{20}$H$_{30}$O$_3$N$_3$ClSiI (M+H$^+$): 550.0790. Found: 550.0773.

3'-O-Allyl-7-deaza-7-iodo-2'-deoxyadenosine (16): To a stirred solution of 15 (752 mg; 1.37 mmol) in anhydrous THF (32 mL) was added 1 M TBAF in THF solution (1.50 mL; 1.50 mmol) and the reaction was stirred at room temperature for 1 h. The solvent was evaporated and the residue was dissolved in 7 M methanolic ammonia (22 mL). The solution was stirred in an autoclave at 115-120° C. for 17 h. After evaporation of the solvent, the residue was purified by flash column chromatography over silica gel using CH$_3$OH—CH$_2$Cl$_2$ (1:20) as the eluent to afford 16 as white solid (479 mg; 84% yield): $^1$H NMR (400 MHz, CD$_3$OD) δ 8.08 (s, 1H, 2-H), 7.56 (s, 1H, 6-H), 6.45 (dd, J=5.8, 8.6 Hz, 1H, 1'-H), 5.90-6.00 (m, 1H, CH$_2$CH═CH$_2$), 5.29-5.35 (dm, J=17.2 Hz, 1H, one of CH$_2$CH═CH$_2$), 5.16-5.21 (dm, J=10.5 Hz, 1H, one of CH$_2$CH═CH$_2$), 4.28 (m, 1H, 3'-H), 4.12 (m, 1H, 4'-H), 4.02-4.12 (m, 2H, CH$_2$CH═CH$_2$), 3.78 (dd, J=3.7, 12.1 Hz, 1H, one of 5'-H), 3.70 (dd, J=3.6, 12.1 Hz, 1H, one of 5'-H), 2.53-2.61 (ddd, J=5.8, 8.6, 13.6 Hz, 1H, one of 2'-H), 2.41-2.47 (ddd, J=2.0, 5.8, 13.5 Hz, 1H, one of 2'-H); $^{13}$C NMR (100 MHz, CD$_3$OD) δ 158.5, 152.3, 150.3, 135.7, 128.8, 117.0, 105.3, 86.8, 86.4, 80.7, 71.0, 63.7, 51.3, 38.8; HRMS (FAB+) calcd for C$_{14}$H$_{18}$O$_3$N$_4$I (M+H$^+$): 417.0424. Found: 417.0438.

3'-O-Allyl-7-deaza-7-[3-[(trifluoroacetyl)amino]-prop-1-ynyl]-2'-deoxyadenosine (17): The procedure is the same as that of 7 and the crude product was purified by flash column chromatography over silica gel using ethyl acetate-hexane (1:1~0) as the eluent to afford 17 as yellow solid (455 mg; 90% yield): $^1$H NMR (400 MHz, CD$_3$OD) δ 8.08 (s, 1H, 2-H), 7.60 (s, 1H, 6-H), 6.41 (dd, J=5.8, 8.6 Hz, 1H, 1'-H), 5.89-

6.00 (m, 1H, CH$_2$CH=CH$_2$), 5.29-5.35 (dm, J=17.3 Hz, 1H, one of CH$_2$CH=CH$_2$), 5.16-5.21 (dm, J=10.4 Hz, 1H, one of CH$_2$CH=CH$_2$), 4.31 (s, 2H, C≡CCH$_2$), 4.29 (m, 1H, 3'-H), 4.13 (m, 1H, 4'-H), 4.01-4.11 (m, 2H, CH$_2$CH=CH$_2$), 3.79 (dd, J=3.6, 12.1 Hz, 1H, one of 5'-H), 3.71 (dd, J=3.5, 12.1 Hz, 1H, one of 5'-H), 2.54-2.62 (ddd, J=5.8, 8.6, 13.6 Hz, 1H, one of 2'-H), 2.42-2.48 (ddd, J=1.9, 5.8, 13.6 Hz, 1H, one of 2'-H); $^{13}$C NMR (100 MHz, CD$_3$OD) δ 158.8, 158.6 (q, J=38 Hz, COCF$_3$), 152.9, 149.6, 135.6, 128.1, 117.1 (q, J=284 Hz, COCF$_3$), 117.0, 104.5, 96.3, 87.3, 86.9, 86.8, 80.7, 77.0, 71.0, 63.8, 38.7, 31.1; HRMS (FAB+) calcd for C$_{19}$H$_{21}$O$_4$N$_5$F$_3$ (M+H$^+$): 440.1546. Found: 440.1544.

3'-O-Allyl-7-deaza-7-(3-aminoprop-1-ynyl)-2'-deoxyadenosine-5'-triphosphate (18): The procedure is the same as that of preparing 9 to yield 17 as colorless syrup: $^1$H NMR (300 MHz, D$_2$O) δ 8.02 (s, 1H, 2-H), 7.89 (s, 1H, 6-H), 6.54 (t, J=6.6 Hz, 1H, 1'-H), 5.89-6.02 (m, 1H, CH$_2$CH=CH$_2$), 5.30-5.39 (dm, J=17.3 Hz, 1H, one of CH$_2$CH=CH$_2$), 5.20-5.27 (dm, J=10.4 Hz, 1H, one of CH$_2$CH=CH$_2$), 4.48 (s, 2H, C≡CCH$_2$), 4.35 (m, 1H, 3'-H), 4.05-4.17 (m, 4H, CH$_2$CH=CH$_2$ and 5'-H), 3.99 (m, 1H, 4'-H), 2.50-2.59 (m, 2H, 2'-H); $^{31}$P NMR (121.4 MHz, D$_2$O) δ −6.1 (d, J=21.1 Hz, 1P, γ-P), −10.8 (d, J=18.8 Hz, 1P, α-P), −21.9 (t, J=19.9 Hz, 1P, β-P).

3'-O-allyl-dATP-ROX (19): The coupling reaction of 18 with PC-ROX-NHS ester (Ref. 2b) afforded 19, following a similar procedure as the preparation of 10. 3'-O-allyl-dATP-PC-ROX 19 was characterized by the primer extension reaction and MALDI-TOF MS.

3) Synthesis of 3'-O-Allyl-dCTP-PC-Bodipy-650 as Shown in FIG. 9

5'-O-(tert-Butyldimethylsilyl)-5-iodo-2'-deoxycytidine (21): The procedure is the same as that of 5 and the crude product was purified by flash column chromatography over silica gel using CH$_3$OH—CH$_2$Cl$_2$ (1:20) as the eluent to afford 21 as white solid (1.18 g; 89% yield): $^1$H NMR (400 MHz, CD$_3$OD) δ 8.18 (s, 1H, 6-H), 6.17 (dd, J=5.8, 7.5 Hz, 1H, 1'-H), 4.34 (m, 1H, 3'-H), 4.04 (m, 1H, 4'-H), 3.93 (dd, J=2.5, 11.6 Hz, 1H, one of 5'-H), 3.84 (dd, J=2.9, 11.6 Hz, 1H, one of 5'-H), 2.41-2.48 (ddd, J=2.5, 5.8, 13.5 Hz, 1H, one of 2'-H), 2.01-2.08 (ddd, J=5.9, 7.6, 13.5 Hz, 1H, one of 2'-H), 0.95 (s, 9H, C(CH$_3$)$_3$), 0.17 (s, 3H, one of SiCH$_3$), 0.16 (s, 3H, one of SiCH$_3$); $^{13}$C NMR (100 MHz, CD$_3$OD) δ 165.5, 156.8, 147.8, 89.4, 88.3, 72.8, 64.6, 57.1, 43.1, 26.7, 19.4, −4.8, −4.9; HRMS (FAB+) calcd for C$_{15}$H$_{27}$O$_4$N$_3$SiI (M+H$^+$): 468.0816. Found: 468.0835.

3'-O-Allyl-5'-O-(tert-butyldimethylsilyl)-5-iodo-2'-deoxycytidine (22): To a stirred solution of 21 (1.18 g; 2.52 mmol) in anhydrous THF (43 mL) was added 95% NaH powder (128 mg; 5.07 mmol). The suspension was stirred at room temperature for 45 min. Allyl bromide (240 μL, 2.79 mmol) was then added at 0° C. and the reaction was stirred at room temperature for 14 h with exclusion of moisture. Saturated aqueous NaHCO$_3$ (10 mL) was added at 0° C. and stirred for 10 min. Most THF was evaporated and the residue was dissolved in ethyl acetate (150 mL). The solution was washed by saturated aqueous NaHCO$_3$ and NaCl respectively, and dried over anhydrous Na$_2$SO$_4$. After evaporation of the solvent, the residue was purified by flash column chromatography over silica gel using ethyl acetate as the eluent to afford 22 as white solid (537 mg; 42% yield): $^1$H NMR (400 MHz, CD$_3$OD) δ 8.15 (s, 1H, 6-H), 6.12 (dd, J=5.6, 8.0 Hz, 1H, 1'-H), 4.17 (m, 1H, 4'-H), 4.14 (m, 1H, 3'-H), 3.98-4.10 (m, 2H, CH$_2$CH=CH$_2$), 3.93 (dd, J=2.8, 11.5 Hz, 1H, one of 5'-H), 3.83 (dd, J=2.8, 11.5 Hz, 1H, one of 5'-H), 2.53-2.60 (ddd, J=1.7, 5.6, 13.6 Hz, 1H, one of 2'-H), 1.94-2.02 (ddd, J=5.9, 8.0, 13.6 Hz, 1H, one of 2'-H), 0.94 (s, 9H, C(CH$_3$)$_3$), 0.17 (s, 3H, one of SiCH$_3$), 0.16 (s, 3H, one of SiCH$_3$); $^{13}$C NMR (100 MHz, CD$_3$OD) δ 165.4, 156.7, 147.7, 135.5, 117.2, 88.2, 87.0, 80.4, 70.9, 64.8, 57.3, 40.1, 26.7, 19.4, −4.7, −4.9; HRMS (FAB+) calcd for C$_{18}$H$_{31}$O$_4$N$_3$SiI (M+H$^+$): 508.1129. Found: 508.1123.

3'-O-allyl-5-iodo-2'-deoxycytidine (23): To a stirred solution of 22 (537 mg; 1.06 mmol) in anhydrous THF (25 mL) was added 1 M TBAF in THF solution (1.17 mL; 1.17 mmol) and the reaction was stirred at room temperature for 1 h. The solvent was evaporated and the residue was dissolved in ethyl acetate (100 mL). The solution was washed by saturated aqueous NaCl and dried over anhydrous Na$_2$SO$_4$. After evaporation of the solvent, the residue was purified by flash column chromatography over silica gel using CH$_3$OH—CH$_2$Cl$_2$ (1:10) as the eluent to afford 23 as white crystals (287 mg; 69% yield): $^1$H NMR (400 MHz, CD$_3$OD) δ 8.47 (s, 1H, 6-H), 6.15 (dd, J=6.2, 6.7 Hz, 1H, 1'-H), 5.87-5.98 (m, 1H, CH$_2$CH=CH$_2$), 5.26-5.33 (dm, J=17.2 Hz, 1H, one of CH$_2$CH=CH$_2$), 5.14-5.19 (dm, J=10.5 Hz, 1H, one of CH$_2$CH=CH$_2$), 4.18 (m, 1H, 3'-H), 4.08 (m, 1H, 4'-H), 3.98-4.10 (m, 2H, CH$_2$CH=CH$_2$), 3.82 (dd, J=3.2, 13.0 Hz, 1H, one of 5'-H), 3.72 (dd, J=3.3, 13.0 Hz, 1H, one of 5'-H), 2.44-2.51 (ddd, J=3.2, 6.0, 13.6 Hz, 1H, one of 2'-H), 2.07-2.15 (m, 1H, one of 2'-H); $^{13}$C NMR (100 MHz, CD$_3$OD) δ 165.4, 156.9, 148.8, 135.6, 117.0, 87.9, 86.9, 79.6, 71.2, 62.7, 57.2, 39.7; HRMS (FAB+) calcd for C$_{12}$H$_{17}$O$_4$N$_3$I (M+H$^+$): 394.0264. Found: 394.0274.

3'-O-Allyl-5-[3-[(trifluoroacetyl)amino]-prop-1-ynyl]-2'-deoxycytidine (24): The procedure is the same as that of 7 and the crude product was purified by flash column chromatography over silica gel using CH$_3$OH—CH$_2$Cl$_2$ (0~1:10) as the eluent to afford 24 as yellow crystals (252 mg; 83% yield): $^1$H NMR (400 MHz, CD$_3$OD) δ 8.31 (s, 1H, 6-H), 6.17 (dd, J=6.0, 7.3 Hz, 1H, 1'-H), 5.87-5.97 (m, 1H, CH$_2$CH=CH$_2$), 5.26-5.33 (dm, J=17.3 Hz, 1H, one of CH$_2$CH=CH$_2$), 5.15-5.19 (dm, J=10.4 Hz, 1H, one of CH$_2$CH=CH$_2$), 4.31 (s, 2H, C≡CCH$_2$), 4.17 (m, 1H, 3'-H), 4.09 (m, 1H, 4'-H), 3.98-4.10 (m, 2H, CH$_2$CH=CH$_2$), 3.80 (dd, J=3.4, 12.0 Hz, 1H, one of 5'-H), 3.72 (dd, J=3.6, 12.0 Hz, 1H, one of 5'-H), 2.46-2.53 (ddd, J=2.9, 5.3, 13.6 Hz, 1H, one of 2'-H), 2.04-2.12 (m, 1H, one of 2'-H); $^{13}$C NMR (100 MHz, CD$_3$OD) δ 166.0, 158.4 (q, J=38 Hz, COCF$_3$), 156.3, 145.8, 135.6, 117.1 (q, J=284 Hz, COCF$_3$), 117.0, 91.9, 90.7, 88.0, 87.0, 79.8, 75.5, 71.2, 62.8, 39.6, 31.0; HRMS (FAB+) calcd for C$_{17}$H$_{20}$O$_5$N$_4$F$_3$ (M+H$^+$): 417.1386. Found: 417.1377.

3'-O-Allyl-5-(3-aminoprop-1-ynyl)-2'-deoxycytidine-5'-triphosphate (25): The procedure is the same as that of preparing 9 to yield 25 as colorless syrup: $^1$H NMR (300 MHz, D$_2$O) δ 8.43 (s, 1H, 6-H), 6.21 (t, J=6.7 Hz, 1H, 1'-H), 5.85-6.00 (m, 1H, CH$_2$CH=CH$_2$), 5.28-5.38 (dm, J=17.3 Hz, 1H, one of CH$_2$CH=CH$_2$), 5.19-5.27 (dm, J=10.4 Hz, 1H, one of CH$_2$CH=CH$_2$), 4.22-4.41 (m, 3H, 3'-H and C≡CCH$_2$), 4.05-4.18 (m, 3H, 4'-H and CH$_2$CH=CH$_2$), 3.94-4.01 (m, 2H, 5'-H), 2.47-2.59 (m, 1H, one of 2'-H), 2.20-2.32 (m, 1H, one of 2'-H); $^{31}$P NMR (121.4 MHz, D$_2$O) δ −7.1 (d, J=19.8 Hz, 1P, γ-P), −11.1 (d, J=19.1 Hz, 1P, α-P), −21.9 (t, J=19.5 Hz, 1P, β-P).

3'O-allyl-dCTP-PC-Bodipy-650 (26): The coupling reaction of 25 with PC-Bodipy-650-NHS ester (Ref. 34b) afforded 26, following a similar procedure as the preparation of 10. 3'-O-allyl-dCTP-PC-Bodipy-650 26 was characterized by the primer extension reaction and MALDI-TOF MS.

4) Synthesis of 3'-O-allyl-dUTP-PC-R6G as Shown in FIG. 10

5'-O-(tert-butyldimethylsilyl)-5-iodo-2'-deoxyuridine (28): The procedure is the same as that of 5 and the crude product was purified by flash column chromatography over silica gel using CH$_3$OH—CH$_2$Cl$_2$ (1:20) as the eluent to afford 28 as white solid (1.18 g; 89% yield): $^1$H NMR (400 MHz, CD$_3$OD) δ 8.17 (s, 1H, 6-H), 6.21 (dd, J=5.9, 7.9 Hz, 1H, 1'-H), 4.36 (m, 1H, 3'-H), 4.02 (m, 1H, 4'-H), 3.93 (dd, J=2.4, 11.5 Hz, 1H, one of 5'-H), 3.85 (dd, J=2.9, 11.5 Hz, 1H, one of 5'-H), 2.30-2.37 (ddd, J=2.3, 5.8, 13.4 Hz, 1H, one of 2'-H), 2.08-2.15 (ddd, J=5.9, 7.9, 13.4 Hz, 1H, one of 2'-H), 0.96 (s, 9H, C(CH$_3$)$_3$), 0.19 (s, 3H, one of SiCH$_3$), 0.17 (s, 3H, one of SiCH$_3$). $^{13}$C NMR (100 MHz, CD$_3$OD) δ 162.4, 151.5, 145.8, 89.3, 87.2, 72.8, 68.7, 64.6, 42.3, 26.8, 19.5, −4.8, −4.9. HRMS (FAB+) Calcd for C$_{15}$H$_{26}$O$_5$N$_2$SiI (M+H$^+$): 469.0656. Found: 469.0672.

3'-O-allyl-5'-O-(tert-butyldimethylsilyl)-5-iodo-2'-deoxyuridine (29): The procedure is the same as that of 22 and the crude product was purified by flash column chromatography over silica gel using ethyl acetate-hexane (1:2.5) as the eluent to afford 29 as white solid (1.03 g; 80% yield). $^1$H NMR (400 MHz, CD$_3$OD) δ 8.15 (s, 1H, 6-H), 6.15 (dd, J=5.6, 8.3 Hz, 1H, 1'-H), 5.87-5.97 (m, 1H, CH$_2$CH=CH$_2$), 5.27-5.33 (dm, J=17.3 Hz, 1H, one of CH$_2$CH=CH$_2$), 5.16-5.21 (dm, J=10.4 Hz, 1H, one of CH$_2$CH=CH$_2$), 4.13-4.18 (m, 2H, 3'-H and 4'-H), 3.99-4.10 (m, 2H, CH$_2$CH=CH$_2$), 3.92 (dd, J=2.7, 11.5 Hz, 1H, one of 5'-H), 3.84 (dd, J=2.7, 11.5 Hz, 1H, one of 5'-H), 2.43-2.49 (ddd, J=1.7, 5.6, 13.6 Hz, 1H, one of 2'-H), 2.02-2.10 (ddd, J=5.6, 8.4, 13.6 Hz, 1H, one of 2'-H), 0.96 (s, 9H, C(CH$_3$)$_3$), 0.18 (s, 3H, one of SiCH$_3$), 0.17 (s, 3H, one of SiCH$_3$). $^{13}$C NMR (100 MHz, CD$_3$OD) δ 162.3, 151.4, 145.5, 135.5, 117.2, 87.0, 86.8, 80.3, 70.9, 69.0, 64.8, 39.4, 26.8, 19.4, −4.7, −4.8. HRMS (FAB+) Calcd for C$_{18}$H$_{30}$O$_5$N$_2$SiI (M+H$^+$): 509.0969. Found: 509.0970.

3'-O-allyl-5'-O-(tert-butyldimethylsilyl)-5-[3-[(trifluoroacetyl)amino]-prop-1-ynyl]-2'-deoxyuridine (30): The procedure is the same as that of 7 and the crude product was purified by flash column chromatography over silica gel using CH$_3$OH—CH$_2$Cl$_2$ (0~1:40) as the eluent to afford 30 as yellow crystals (786 mg; 73% yield). $^1$H NMR (400 MHz, CD$_3$OD) δ 8.11 (s, 1H, 6-H), 6.18 (dd, J=5.8, 7.9 Hz, 1H, 1'-H), 5.87-5.97 (m, 1H, CH$_2$CH=CH$_2$), 5.27-5.33 (dm, J=17.2 Hz, 1H, one of CH$_2$CH=CH$_2$), 5.16-5.21 (dm, J=10.4 Hz, 1H, one of CH$_2$CH=CH$_2$), 4.27-4.32 (dd, J=17.7 Hz, 1H, one of C≡CCH$_2$), 4.21-4.27 (dd, J=17.7 Hz, 1H, one of C≡CCH$_2$), 4.14-4.18 (m, 2H, 3'-H and 4'-H), 3.98-4.10 (m, 2H, CH$_2$CH=CH$_2$), 3.93 (dd, J=2.4, 11.5 Hz, 1H, one of 5'-H), 3.84 (dd, J=2.2, 11.5 Hz, 1H, one of 5'-H), 2.44-2.50 (ddd, J=1.8, 5.7, 13.5 Hz, 1H, one of 2'-H), 2.04-2.12 (ddd, J=5.6, 8.0, 13.5 Hz, 1H, one of 2'-H), 0.94 (s, 9H, C(CH$_3$)$_3$), 0.16 (s, 3H, one of SiCH$_3$), 0.15 (s, 3H, one of SiCH$_3$). $^{13}$C NMR (100 MHz, CD$_3$OD) δ 164.1, 158.0 (q, J=37 Hz, COCF$_3$), 150.6, 144.3, 135.5, 117.3, 117.1 (q, J=284 Hz, COCF$_3$), 99.5, 88.9, 87.2, 86.9, 80.3, 76.0, 71.0, 64.7, 39.6, 30.7, 26.6, 19.3, −5.0, −5.2. HRMS (FAB+) m/z: anal. Calcd for C$_{23}$H$_{33}$O$_6$N$_3$F$_3$Si (M+H$^+$): 532.2091. Found: 532.2074.

3'-O-allyl-5-[3-[(trifluoroacetyl)amino]-prop-1-ynyl]-2'-deoxyuridine (31): The procedure is the same as that of 23 and the crude product was purified by flash column chromatography over silica gel using ethyl acetate-hexane (3:1) as the eluent to afford 31 as yellow solid (302 mg; 49% yield). $^1$H NMR (400 MHz, CD$_3$OD) δ 8.29 (s, 1H, 6-H), 6.19 (dd, J=6.1, 7.4 Hz, 1H, 1'-H), 5.87-5.99 (m, 1H, CH$_2$CH=CH$_2$), 5.27-5.33 (dm, J=17.2 Hz, 1H, one of CH$_2$CH=CH$_2$), 5.15-5.20 (dm, J=10.4 Hz, 1H, one of CH$_2$CH=CH$_2$), 4.27 (s, 2H, C≡CCH$_2$), 4.20 (m, 1H, 3'-H), 3.99-4.09 (m, 3H, 4'-H and CH$_2$CH=CH$_2$), 3.80 (dd, J=3.3, 12.0 Hz, 1H, one of 5'-H), 3.72 (dd, J=3.4, 12.0 Hz, 1H, one of 5'-H), 2.39-2.46 (ddd, J=2.6, 5.9, 13.7 Hz, 1H, one of 2'-H), 2.14-2.22 (ddd, J=6.3, 7.5, 13.7 Hz, 1H, one of 2'-H). $^{13}$C NMR (100 MHz, CD$_3$OD) δ 164.2, 158.0 (q, J=38 Hz, COCF$_3$), 150.8, 145.3, 135.6, 117.2 (q, J=285 Hz, COCF$_3$), 117.1, 99.5, 88.3, 87.1, 87.0, 79.9, 75.9, 71.2, 62.9, 39.0, 30.8. HRMS (FAB+) Calcd for C$_{17}$H$_{19}$O$_6$N$_3$F$_3$ (M+H$^+$): 418.1226. Found: 418.1213.

3'-O-allyl-5-(3-aminoprop-1-ynyl)-2'-deoxyuridine-5'-triphosphate (32): The procedure is the same as that of preparing 9 to yield 32 as colorless syrup: $^1$H NMR (300 MHz, D$_2$O) δ 8.31 (s, 1H), 6.17 (t, 1H), 5.81-5.90 (m, 1H), 5.18 (d, 1H), 5.14 (d, 1H), 4.34 (m, 2H), 4.03-4.15 (m, 2H), 4.00 (d, 2H), 3.93 (s, 2H), 2.44-2.47 (m, 1H), 2.22-2.24 (m, 1H). $^{31}$P NMR (121.4 MHz, D$_2$O) δ −5.90 (d, J=19.0 Hz, 1P, γ-P), −11.43 (d, J=20.0 Hz, 1P, α-P), −22.25 (t, J=19.8 Hz, 1P, β-P).

3'-O-allyl-dUTP-PC-R6G (33): The coupling reaction of 32 with PC-R6G-NHS ester (Ref. 34b) afforded 33, following a similar procedure as the preparation of 10. 3'-O-allyl-dCTP-PC-Bodipy-650 33 was characterized by the primer extension reaction and MALDI-TOF MS.

II. 3'-O-allyl Modified Photocleavable Fluorescent Nucleotides as Reversible Terminators for Primer Extension Reactions 1) Primer Extension by Using 3'-O-Allyl-dGTP-PC-Bodipy-FL-510 (10) and Photocleavage of the Extension Product 34. The polymerase extension reaction mixture consisted of 60 pmol of primer (5'-GTTGATGTACACATTGTCAA-3') (SEQ ID NO:4), 80 pmol of 100-mer template (5'-TACCCG-GAGGCCAAGTACGGCGGGTACGTCCT-TGACAATGTGTACATCAACATCACCTAC-CACCATGTCAGTCTCGGTTGGATCCT CTATTGTGTCCGGG-3') (SEQ ID NO:5), 120 pmol of 3'-O-allyl-dGTP-PC-Bodipy-FL-510, 1× Thermopol reaction buffer (20 mM Tris-HCl/10 mM (NH$_4$)$_2$SO$_4$/10 mM KCl/2 mM-MgSO$_4$/0.1% Triton X-100, pH 8.8, New England Biolabs), and 6 units of 9° N Polymerase (exo-) A485L/Y409V in a total volume of 20 μl. The reaction consisted of 20 cycles at 94° C. for 20 sec, 46° C. for 40 sec, and 60° C. for 90 sec. After the reaction, a small portion of the DNA extension product was desalted by using ZipTip and analyzed by MALDI-TOF MS, which shows a dominant peak at m/z 7,052 corresponding to the DNA product 34. The rest of the product mixture was freeze-dried, resuspended in 200 μl of deionized water, and irradiated at 355 nm for 10 sec to cleave the fluorophore from the DNA to yield product 35 and then analyzed by MALDI-TOF MS.

Deallylation of photocleaved DNA extension product 35. DNA product 35 (20 pmol) was added to a mixture of degassed 1× Thermopol reaction buffer (20 mM Tris-HCl/10 mM (NH$_4$)$_2$SO$_4$/10 mM KCl/2 mM MgSO$_4$/0.1% Triton X-100, pH 8.8, 1 μl), Na$_2$PdCl$_4$ in degassed H$_2$O (7 μl, 23 nmol) and P(PhSO$_3$Na)$_3$ in degassed H$_2$O (10 μl, 176 nmol) to perform deallylation. The reaction mixture was then placed in a heating block and incubated at 70° C. for 30 seconds to yield quantitatively deallylated DNA product 36 and analyzed by MALDI-TOF MS.

Primer Extension Reaction Performed with the deallylated DNA Product. The deallylated DNA product 36 was used as a primer in a single-base extension reaction. The 20 μl reaction mixture consisted of 60 pmol of the deallylated product 36, 80 pmol of the 100-mer template (5'-TACCCGGAGGC-CAAGTACGGCGGGTACGTCCTTGACAAT-GTGTACATCAACATCACCTACCACCAT-GTCAGTCTCGGTTGGATCCT CTATTGTGTCCGGG-3') (SEQ ID NO:6), 120 pmol of 3'-O-allyl-dGTP-PC-Bodipy-FL-510 (10), 6 units of 9° N Polymerase (exo-) A485L/Y409V in a total volume of 20 μl. The reaction consisted of 20 cycles at 94° C. for 20 sec, 46° C. for 40 sec, and 60° C. for 90 sec. The DNA extension product 37 was desalted by using the ZipTip protocol, and a small portion was analyzed by using MALDI-TOF MS. The remaining product was then irradiated with near-UV light (355 nm) for 10 sec to cleave the fluorophore from the extended DNA product. The resulting photocleavage product 38 was analyzed by using MALDI-TOF MS. Finally, deallylation of the photocleavage product 38 was performed using a Pd-catalyzed deallylation·reaction resulting in a deallylated DNA product 39, which was then analyzed by MALDI-TOF MS.

2) Primer Extension with 3'-O-Allyl-dATP-PC-ROX (19), followed by Photocleavage and Deallylation of the Extension Product. The polymerase extension reaction mixture consisted of 60 pmol of primer (5'-TAGATGACCCTGCCTTGTCG-3') (SEQ ID NO:7), 80 pmol of 100-mer template (5'-GAAGGAGACACGCGGCCAGAGAGGGTC-CTGTCCGTGTTTGTGCGTGGAGTTCGA-CAAGGCAGGGTCATCTAATGGTGATGA GTCCTATC-CTTTTCTCTTCGTTCTCCGT-3') (SEQ ID NO:8), 120 pmol of 3'-O-allyl-dUTP-PC-R6G, 120 pmol of 3'-O-allyl-dATP-PC-ROX, 120 pmol of 3'-O-allyl-dGTP-PC-Bodipy-FL-510, 120 pmol of 3'-O-allyl-dCTP-PC-Bodipy-650, 1× Thermopol reaction buffer (20 mM Tris-HCl/10 mM $(NH_4)_2SO_4$/10 mM KCl/2 mM $MgSO_4$/0.1% Triton X-100, pH 8.8, New England Biolabs), and 6 units of 9° N Polymerase (exo-) A485L/Y409V in a total volume of 20 µl. The reaction consisted of 20 cycles at 94° C. for 20 sec, 55° C. for 40 sec, and 68° C. for 90 sec, which yielded DNA extension product 40. DNA extension product mixture was freeze-dried, resuspended in 200 µl of deionized water, and irradiated at 355 nm for 10 sec to cleave the fluorophore from the DNA to yield DNA product 41 and then analyzed by MALDI-TOF MS. Finally, deallylation of the photocleavage product was performed using a Pd-catalyzed deallylation reaction resulting in a deallylated DNA product 42, which was then analyzed by MALDI-TOF MS.

3) Primer Extension with 3'-O-Allyl-dCTP-PC-Bodipy-650 (26), followed by Photocleavage and Deallylation of the Extension Product. The polymerase extension reaction mixture consisted of 60 pmol of primer (5'-ACACAATAGAG-GATCCAACCG AGA-3') (SEQ ID NO:9), 80 pmol of 100-mer template (5'-TACCCGGAGGCCAAGTACGGCGGGT ACGTCCTTGACAATGTGTACATCAACAT-CACCTACCACCATGTCAGTCTCGGTTG GATCCTC-TATTGTGTCCGGG-3') (SEQ ID NO:10), 120 pmol of 3'-O-allyl-dUTP-PC-R6G, 120 pmol of 3'-O-allyl-dATP-PC-ROX, 120 pmol of 3'-O-allyl-dGTP-PC-Bodipy-FL-510, 120 pmol of 3'-O-allyl-dCTP-PC-Bodipy-650, 1× Thermopol reaction buffer (20 mM Tris-HCl/10 mM $(NH_4)_2SO_4$/10 mM KCl/2 mM $MgSO_4$/0.1% Triton X-100, pH 8.8, New England Biolabs), and 6 units of 9° N Polymerase (exo-) A485L/Y409V in a total volume of 20 µl. The reaction consisted of 20 cycles at 94° C. for 20 sec, 64° C. for 40 sec, and 72° C. for 90 sec, which yielded DNA extension product 43. DNA extension product mixture was freeze-dried, resuspended in 200 µl of deionized water, and irradiated at 355 nm for 10 sec to cleave the fluorophore from the DNA to yield DNA product 44 and then analyzed by MALDI-TOF MS. Finally, deallylation of the photocleavage product was performed using a Pd-catalyzed deallylation reaction resulting in a deallylated DNA product 45, which was then analyzed by MALDI-TOF MS.

4) Primer Extension with 3'-O-Allyl-dUTP-PC-R6G (33), followed by Photocleavage and Deallylation of the Extension Product. The polymerase extension reaction mixture consisted of 60 pmol of primer (5'-GATAGGACTCATCACCA-3') (SEQ ID NO:11), 80 pmol of 100-mer template (5'-GAAGGAGACACGCGGCCAGAGAGGGTCTGTCCGT-GTTTGT GCG TGGAGTTCGACAAGGCAGGGT-CATCTAATGGTGATGAGTCCTATCCTTT TCTCT-TCGTTCTCCGT-3') (SEQ ID NO:12), 120 pmol of 3'-O-allyl-dUTP-PC-R6G, 120 pmol of 3'-O-allyl-dATP-PC-ROX, 120 pmol of 3'-O-allyl-dGTP-PC-Bodipy-FL-510, 120 pmol of 3'-O-allyl-dCTP-PC-Bodipy-650, 1× Thermopol reaction buffer (20 mM Tris-HCl/10 mM $(NH_4)_2SO_4$/10 mM KCl/2 mM $MgSO_4$/0.1% Triton X-100, pH 8.8, New England Biolabs), and 6 units of 9° N Polymerase (exo-) A485L/Y409V in a total volume of 20 µl. The reaction consisted of 20 cycles at 94° C. for 20 sec, 46° C. for 40 sec, and 60° C. for 90 sec, which yielded DNA extension product 46. DNA extension product mixture was freeze-dried, resuspended in 200 µl of deionized water, and irradiated at 355 nm for 10 sec to cleave the fluorophore from the DNA to yield DNA product 47 and then analyzed by MALDI-TOF MS. Finally, deallylation of the photocleavage product was performed using a Pd-catalyzed deallylation reaction resulting in a deallylated DNA product 48, which was then analyzed by MALDI-TOF MS.

EXAMPLE 3

Four-Color DNA Sequencing by Synthesis on a Chip Using Photocleavable Fluorescent Nucleotides Synopsis In this example, 4-color DNA sequencing by synthesis (SBS) on a chip using four photocleavable fluorescent nucleotide analogues (dGTP-PC-Bodipy-FL-510, dUTP-PC-R6G, dATP-PC-ROX, and dCTP-PC-Bodipy-650) is demonstrated. Each nucleotide analogue consists of a different fluorophore attached to the 5-position of the pyrimidines (C and U) and the 7-position of the purines (G and A) through a photocleavable 2-nitrobenzyl linker. After verifying that these nucleotides could be successfully incorporated into a growing DNA strand in a solution-phase polymerase reaction and the fluorophore could be cleaved using laser irradiation ($\lambda\sim355$ nm) in 10 seconds, an SBS reaction was then performed on a chip which contains a self-priming DNA template covalently immobilized using 1,3-dipolar azide-alkyne cycloaddition. The DNA template was produced by a polymerase chain reaction using an azido-labeled primer and the self-priming moiety was attached to the immobilized DNA template by enzymatic ligation. Each cycle of SBS consists of the incorporation of the photocleavable fluorescent nucleotide into the DNA, detection of the fluorescent signal and photocleavage of the fluorophore. The entire process was repeated to identify 12 continuous bases in the DNA template. These results demonstrate that photocleavable fluorescent nucleotide analogues can be incorporated accurately into a growing DNA strand during a polymerase reaction in solution phase as well as on a chip. Moreover, all 4 fluorophores can be detected and then efficiently cleaved using near-UV irradiation, thereby allowing continuous identification of the DNA template sequence. Optimization of the steps involved increases the readlength.

Results

DNA sequencing is a fundamental tool for biological science. The completion of the Human Genome Project has set the stage for screening genetic mutations to identify disease genes on a genome-wide scale (42). Accurate high-throughput DNA sequencing methods are needed to explore the complete human genome sequence for applications in clinical medicine and health care. Recent studies have indicated that an important route for identifying functional elements in the human genome involves sequencing the genomes of many species representing a wide sampling of the evolutionary tree (43). To overcome the limitations of the current electrophoresis-based sequencing technology (44-47), a variety of new DNA-sequencing methods have been investigated. Such approaches include sequencing by hybridization (48), mass spectrometry based sequencing (49-51), sequence-specific detection of single-stranded DNA using engineered nanopores (52). More recently, DNA sequencing by synthesis (SBS) approaches such as pyrosequencing (53), sequencing of single DNA molecules (54) and polymerase colonies (55) have been widely explored.

The concept of DNA sequencing by synthesis was revealed in 1988 (56). This approach involves detection of the identity of each nucleotide immediately after its incorporation into a growing strand of DNA in a polymerase reaction. Thus far, no complete success has been reported in using such a system to sequence DNA unambiguously. An SBS approach was proposed using photocleavable fluorescent nucleotide analogues on a surface in 2000 (57). In this approach, modified nucleotides are used as reversible terminators, in which a different fluorophore with a distinct fluorescent emission is linked to each of the 4 bases through a photocleavable linker and the 3'-OH group is capped by a small chemical moiety. DNA polymerase incorporates only a single nucleotide analogue complementary to the base on a DNA template covalently linked to a surface. After incorporation, the unique fluorescence emission is detected to identify the incorporated nucleotide and the fluorophore is subsequently removed photochemically. The 3'-OH group is then chemically regenerated, which allows the next cycle of the polymerase reaction to proceed. Since the large surface on a DNA chip can have a high density of different DNA templates spotted, each cycle can identify many bases in parallel, allowing the simultaneous sequencing of a large number of DNA molecules. The advantage of using photons as reagents for initiating photoreactions to cleave the fluorophore is that no additional chemical reagents are required to be introduced into the system and clean products can be generated with no need for subsequent purification. It has previously been established the feasibility of performing SBS on a chip using a synthetic DNA template and photocleavable pyrimidine nucleotides (C and U) (58). As further development of this approach, here the design and synthesis of 4 photocleavable nucleotide analogues (A, C, G, U) is reported, each of which contains a unique fluorophore with a distinct fluorescence emission. Initially, it is established that these nucleotides are good substrates for DNA polymerase in a solution-phase DNA extension reaction and that the fluorophore can be removed with high speed and efficiency by laser irradiation (□~355 nm). Subsequently, SBS was performed using these 4 photocleavable nucleotide analogues to identify the sequence of a DNA template immobilized on a chip. The DNA template was produced by PCR using an azido-labeled primer, and was immobilized on the surface of the chip with 1,3-dipolar azide-alkyne cycloaddition chemistry. A self-priming moiety was then covalently attached to the DNA template by enzymatic ligation to allow the polymerase reaction to proceed on the DNA immobilized on the surface.

Materials and Methods

All chemicals were purchased from Sigma-Aldrich unless otherwise indicated. 1H NMR spectra were recorded on a Bruker 400 spectrometer. High-resolution MS (HRMS) data were obtained by using a JEOL JMS HX 110A mass spectrometer. Mass measurement of DNA was made on a Voyager DE matrix-assisted laser desorption ionization-time-of-flight (MALDI-TOF) mass spectrometer (Applied Biosystems). Photolysis was performed using a Spectra Physics GCR-150-30 Nd-YAG laser that generates light pulses at 355 nm (ca. 50 mJ/pulse, pulse length ca. 7 ns) at a frequency of 30 Hz with a light intensity at ca. 1.5 W/cm2. The scanned fluorescence emission images were obtained by using a ScanArray Express scanner (Perkin-Elmer Life Sciences) equipped with four lasers with excitation wavelengths of 488, 543, 594, and 633 nm and emission filters centered at 522, 570, 614, and 670 nm.

Synthesis of Photocleavable Fluorescent Nucleotides.

Figure 16:
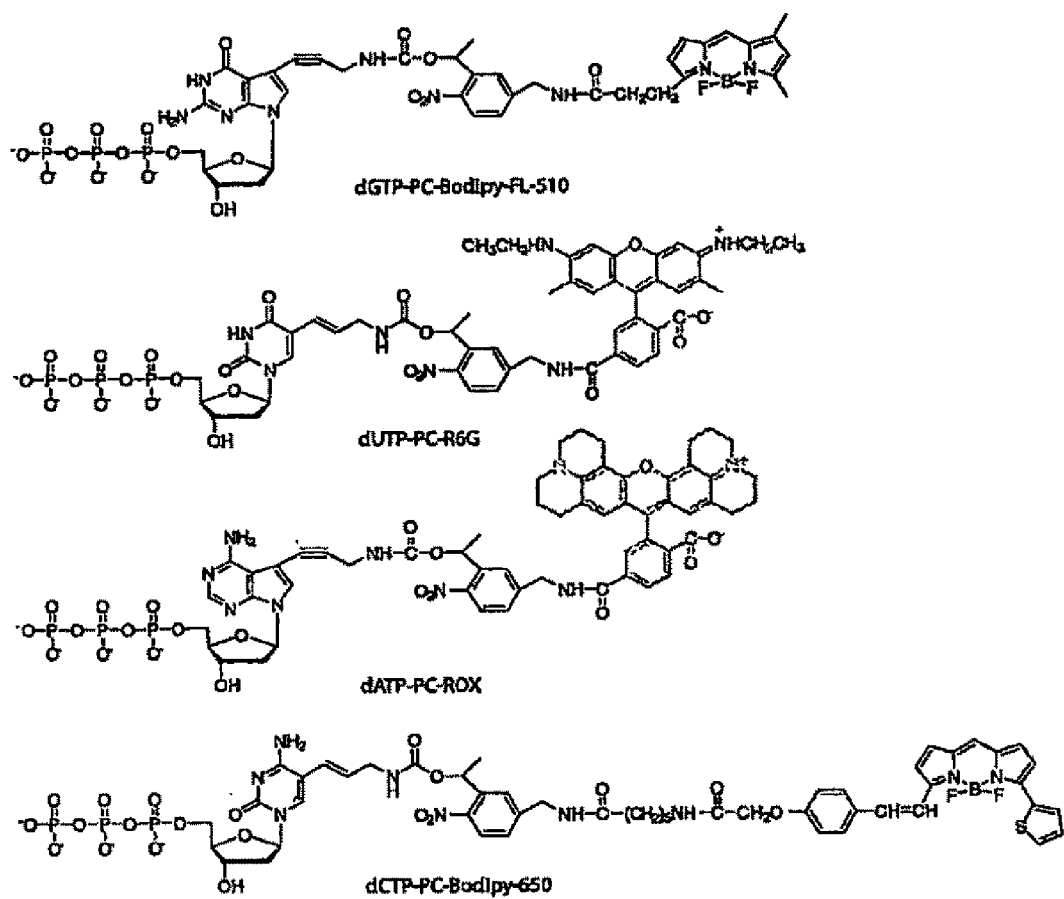
FIG. 16: Structures of dGTP-PC-Bodipy-FL-510 ($\lambda_{abs\ (max)}$=502 nm; $\lambda_{em\ (max)}$=510 nm), dUTP-PC-R6G ($\lambda_{abs\ (max)}$=525 nm; $\lambda_{em\ (max)}$=550 nm), dATP-PC-ROX ($\lambda_{abs\ (max)}$=575 nm; $\lambda_{em\ (max)}$=602 nm), and dCTP-PC-Bodipy-650 ($\lambda_{abs\ (max)}$=630 nm; $\lambda_{em\ (max)}$=650 nm).
Figure 17:
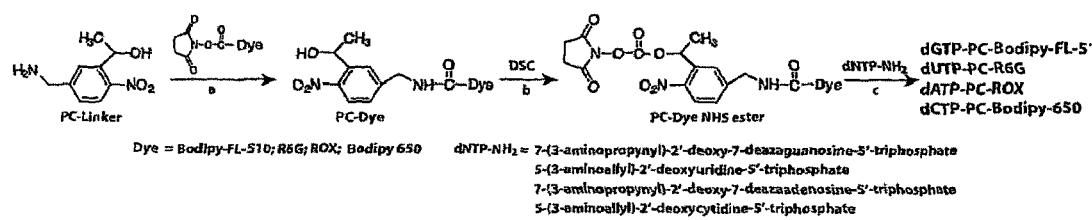
FIG. 17: Synthesis of photocleavable fluorescent nucleotides. (a) acetonitrile or DMF/1 M NaHCO$_3$ solution; (b) N,N'-disuccinimidyl carbonate (DSC), triethylamine; (c) 0.1 M Na$_2$CO$_3$/NaHCO$_3$ aqueous buffer (pH 8.5-8.7).

Photocleavable fluorescent nucleotides dGTP-PC-Bodipy-FL-510, dUTP-PC-R6G, dATP-PC-ROX and dCTP-PC-Bodipy-650 (FIG. 16) were synthesized according to FIG. 17 using a similar method as reported previously (57). A photocleavable linker (PC-Linker) 1-[5-(aminomethyl)-2-nitrophenyl]ethanol was reacted with the NHS ester of the corresponding fluorescent dye to produce an intermediate PC-Dye, which was converted to a PC-Dye NHS ester by reacting with N,N'-disuccinimidyl carbonate. The coupling reaction between the different PC-Dye NHS esters and the amino nucleotides (dATP-NH2 and dGTP-NH2 from Perkin-Elmer; dUTP-NH2 from Sigma; dCTP-NH2 from TriLink BioTechnologies) produced the 4 photocleavable fluorescent nucleotides.

DNA Polymerase Reaction Using 4 Photocleavable Fluorescent Nucleotide Analogues in Solution.

Figure 18:
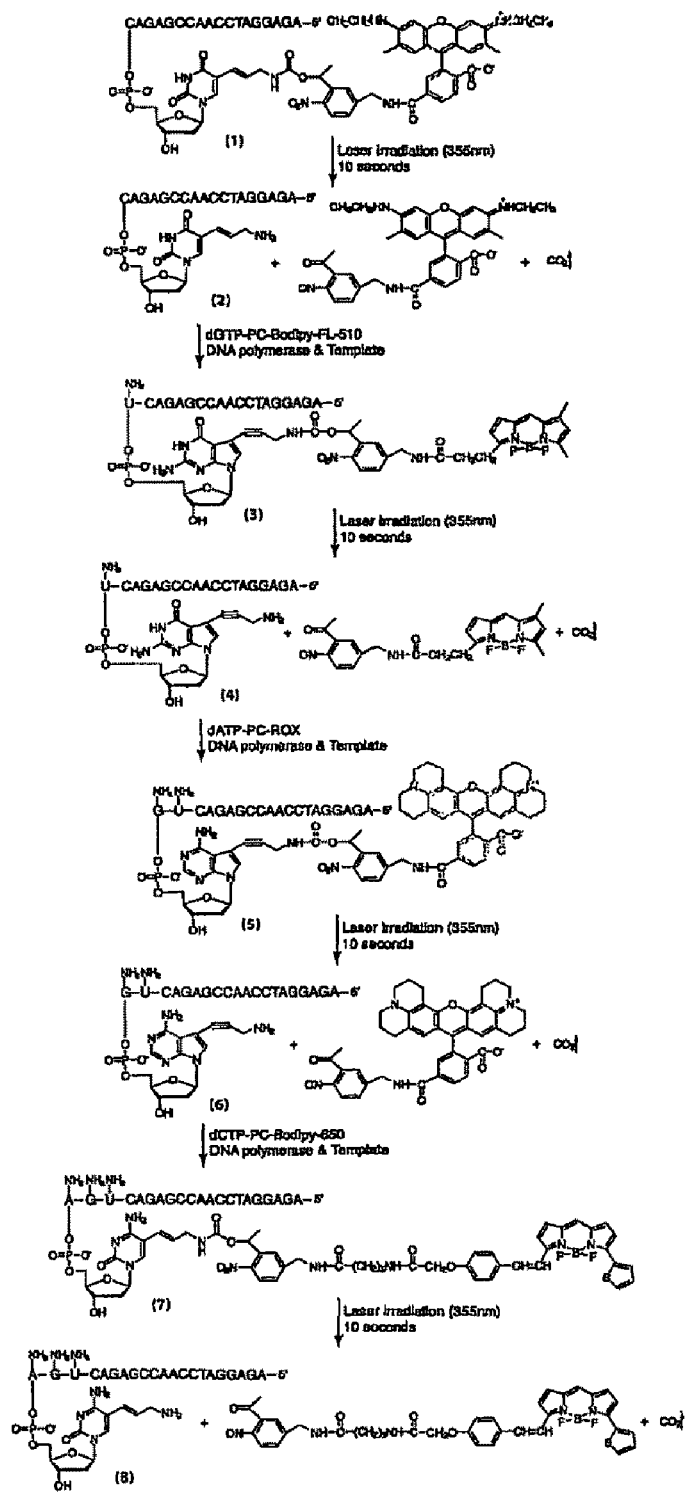
FIG. 18: DNA extension reaction performed in solution phase to characterize the 4 different photocleavable fluorescent nucleotide analogues (dUTP-PC-R6G, dGTP-PC-Bodipy-FL-510, dATP-PC-ROX, dCTP-PC-Bodipy-650). After each extension reaction, the DNA extension product is purified by HPLC for MALDI-TOF MS measurement, to verify that it is the correct extension product. Photolysis is performed to produce a DNA product that is used as a primer for the next DNA extension reaction.

Four nucleotide analogues were characterized, dGTP-PC-Bodipy-FL-510, dUTP-PC-R6G, dATP-PC-ROX and dCTP-PC-Bodipy-650 by performing four continuous DNA-extension reactions sequentially using a primer (5'-AGAGGATCCAACCGAGAC-3') (SEQ ID NO:13) and a synthetic DNA template (5'-GTGTACATCAACATCAC-CTACCACCATGTCAGTCTCGGTTGGATC-CTCTATTGTGTCCGG-3') (SEQ ID NO:14) corresponding to a portion of exon 7 of the human p53 gene (FIG. 18). The four nucleotides in the template immediately adjacent to the annealing site of the primer were 3'-ACTG-5'. First, a polymerase extension reaction using dUTP-PC-R6G along with the primer and the template was performed producing a single base extension product. The reaction mixture for this, and all subsequent extension reactions, consisted of 80 pmol of template, 50 pmol of primer, 80 pmol of the particular photocleavable fluorescent nucleotide, 1× Thermo Sequenase reaction buffer, and 4 U of Thermo Sequenase DNA polymerase (Amersham Biosciences) in a total volume of 20 µL. The reaction consisted of 25 cycles at 94° C. for 20 sec, 48° C. for 40 sec, and 60° C. for 75 sec. Subsequently, the extension product was purified by using reverse-phase HPLC. An Xterra MS C18 (4.6×50-mm) column (Waters) was used for the HPLC purification. Elution was performed over 120 minutes at a flow rate of 0.5 mL/min with the temperature set at 50° C. by using a linear gradient (12-34.5%) of methanol in a buffer consisting of 8.6 mM triethylamine and 100 mM hexafluoroisopropyl alcohol (pH 8.1). The fraction containing the desired DNA product was collected and freeze-dried for analysis using MALDI-TOF mass spectrometry. For photocleavage, the purified DNA extension product bearing the fluorescent nucleotide analogue was resuspended in 200 µL of deionized water. The mixture was irradiated for 10 seconds in a quartz cell with path lengths of 1.0 cm employing a Nd-YAG laser at 355 nm and then analyzed by MALDI-TOF MS. After photocleavage, the DNA product with the fluorophore removed was used as a primer for a second extension reaction using dGTP-PC-Bodipy-FL-510. The second extended product was then purified by HPLC and photolyzed. The third extension using dATP-PC-ROX and the fourth extension using dCTP-PC-Bodipy-650 were carried out in a similar manner using the previously extended and photocleaved product as the primer.

PCR Amplification to Produce Azido-Labeled DNA Template.

An azido-labeled PCR product was obtained using a 100-bp template (5'-AGCGACTGCTATCATGTCATATC-GACGTGCTCACTAGCTCTACATATGCGTGCGT GAT-CAGATGACGTATCGATGCTGACTATAGTCTCCCATG-CGAGTG-3') (SEQ ID NO:15), a 24-bp azido-labeled forward primer (5'-N3-AGCGACTGCTATCATGTCATATCG-3') (SEQ ID NO:16), and a 24-bp unlabeled reverse primer (5'-CACTCGCATGGGAGACTATAGTCA-3') (SEQ ID NO:17). In a total reaction volume of 50 µL, 1 pmol of template and 30 pmol of forward and reverse primers were mixed with 1 U of AccuPrime Pfx DNA polymerase and 5 µL of 10× AccuPrime Pfx reaction mix (Invitrogen) containing 1 mM of $MgSO_4$ and 0.3 mM of dNTP. The PCR reaction consisted of an initial denaturation step at 95° C. for 1 min, followed by 38 cycles at 94° C. for 15 sec, 63° C. for 30 sec, 68° C. for 30 sec. The product was purified using a 96 QIAquick multiwell PCR purification kit (Qiagen) and the quality was checked using 2% agarose gel electrophoresis in 1× TAE buffer. The concentration of the purified PCR product was measured using a Perkin-Elmer Lambda 40 UV-Vis spectrophotometer.

Construction of a Self-Priming DNA Template on a Chip by Enzymatic Ligation.

The amino-modified glass slide (Sigma) was functionalized to contain a terminal alkynyl group as described previously (57). The azido-labeled DNA product generated by PCR was dissolved in $DMSO/H_2O$ (1/3, v/v) to obtain a 20 µM solution. 5 µL of the DNA solution was mixed with CuI (10 nmol, 100 eq.) and N,N-diisopropyl-ethylamine (DIPEA) (10 nmol, 100 eq.) and then spotted onto the alkynyl-modified glass surface in the form of 6 µL drops. The glass slide was incubated in a humid chamber at room temperature for 24 hr, washed with deionized water ($dH_2O$) and SPSC buffer (50 mM sodium phosphate, 1 M NaCl, pH 6.5) for 1 hr (57), and finally rinsed with $dH_2O$. To denature the double stranded PCR-amplified DNA to remove the non-azido-labeled strand, the glass slide was immersed into 0.1 M NaOH solution for 10 min and then washed with 0.1 M NaOH and $dH_2O$, producing a single stranded DNA template that is immobilized on the chip. For the enzymatic ligation of a self-priming moiety to the immobilized DNA template on the chip, a 5'-phosphorylated 40-bp loop primer (5'-PO3-GCTGAATTCCGCGT-TCGCGGAATTCAGCCACTCGCATGGG-3') (SEQ ID NO:18) was synthesized. This primer contained a thermally stable loop sequence 3'-G(CTTG)C-5', a 12-bp stem, and a 12-bp overhanging end that would be annealed to the immobilized single stranded template at its 3'-end. A 10 µL solution consisting of 100 pmol of the primer, 10 U of Taq DNA ligase, 0.1 mM NAD, and 1× reaction buffer (New England Biolabs) was spotted onto a location of the chip containing the immobilized DNA and incubated at 45° C. for 4 hr. The glass slide was washed with $dH_2O$, SPSC buffer, and again with $dH_2O$. The formation of a stable hairpin was ascertained by covering the entire surface with 1× reaction buffer (26 mM Tris HCl/ 6.5 mM $MgCl_2$, pH 9.3), incubating it in a humid chamber at 94° C. for 5 min to dissociate any partial hairpin structure, and then slowly cooling down to room temperature for reannealing.

SBS Reaction on a Chip with Four Photocleavable Fluorescent Nucleotide Analogues.

One microliter of a solution consisting of dATP-PC-ROX (60 pmol), 2 U of Thermo Sequenase DNA polymerase, and 1× reaction buffer was spotted on the surface of the chip, where the self-primed DNA moiety was immobilized. The nucleotide analogue was allowed to incorporate into the primer at 72° C. for 5 min. After washing with a mixture of SPSC buffer, 0.1% SDS, and 0.1% Tween 20 for 10 min, the surface was rinsed with $dH_2O$ and ethanol successively, and then scanned with a ScanArray Express scanner to detect the fluorescence signal. To perform photocleavage, the glass chip was placed inside a chamber (50×50×50 mm) filled with acetonitrile/water (1/1, v/v) solution and irradiated for 1 min with the Nd-YAG laser at 355 nm. The light intensity applied on the glass surface was ca. 1.5 $W/cm^2$. After washing the surface with $dH_2O$ and ethanol, the surface was scanned again to compare the intensity of fluorescence after photocleavage with the original fluorescence intensity. This process was followed by the incorporation of dGTP-PC-Bodipy-FL-510, with the subsequent washing, fluorescence detection, and photocleavage processes performed as described above. The same cycle was repeated 10 more times using each of the four photocleavable fluorescent nucleotide analogues complementary to the base on the template. For a negative control experiment, 1 µL solution containing dATP-PC-ROX (60 pmol), and 1× reaction buffer was added on to the DNA immobilized on the chip in the absence of DNA polymerase and then incubated at 72° C. for 5 min, followed by the same washing and detection steps as above.

Results and Discussion

To demonstrate the feasibility of carrying out DNA sequencing by synthesis on a chip, four photocleavable fluorescent nucleotide analogues (dGTP-PC-Bodipy-FL-510, dUTP-PC-R6G, dATP-PC-ROX, and dCTP-PC-Bodipy-650) (FIG. 16) were synthesized according to FIG. 17 using a similar procedure as reported previously (57). Modified DNA polymerases have been shown to be highly tolerant to nucleotide modifications with bulky groups at the 5-position of pyrimidines (C and U) and the 7-position of purines (A and G) (59, 60). Thus, each unique fluorophore was attached to the 5 position of C/U and the 7 position of A/G through a photocleavable 2-nitrobenzyl linker.

Figure 19:
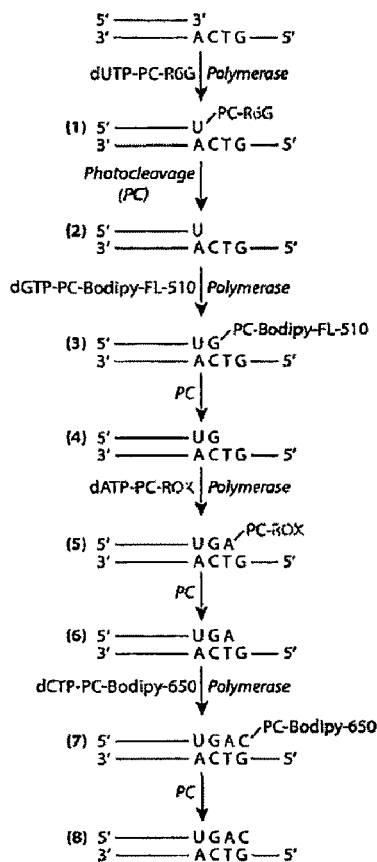
FIG. 19: The polymerase extension scheme (left) and MALDI-TOF MS spectra of the four consecutive extension products and their photocleavage products (right). Primer extended with dUTP-PC-R6G (1), and its photocleavage product 2; Product 2 extended with dGTP-PC-Bodipy-FL-510 (3), and its photocleavage product 4; Product 4 extended with dATP-PC-ROX (5), and its photocleavage product 6; Product 6 extended with dCTP-PC-Bodipy-650 (7), and its photocleavage product 8. After 10 seconds of irradiation with a laser at 355 nm, photocleavage is complete with all the fluorophores cleaved from the extended DNA products.
Figure 19:
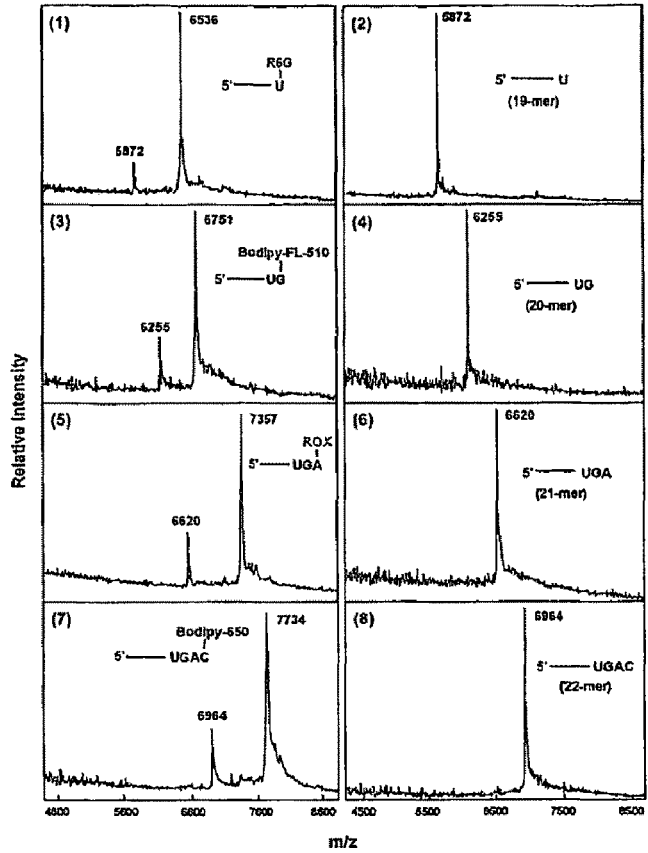

In order to verify that these fluorescent nucleotides are incorporated accurately in a base-specific manner in a polymerase reaction, four continuous steps of DNA extension and photocleavage by near UV irradiation were carried out in solution as shown in FIG. 18. This allows the isolation of the DNA product at each step for detailed molecular structure characterization as shown in FIG. 19. The first extension product 5'-U(PC-R6G)-3' 1 was purified by HPLC and analyzed using MALDI-TOF MS [FIG. 19(1)]. This product was then irradiated at 355 nm using an Nd-YAG laser for 10 seconds and the photocleavage product 2 was also analyzed using MALDI-TOF MS [FIG. 19(2)]. Near UV light absorption by the aromatic 2-nitrobenzyl linker causes reduction of the 2-nitro group to a nitroso group and an oxygen insertion into the carbon-hydrogen bond followed by cleavage and decarboxylation (61). As can be seen from FIG. 19(1), the MALDI-TOF MS spectrum consists of a distinct peak at m/z 6536 corresponding to the DNA extension product 5'-U(PC-R6G)-3' (1), which confirms that the nucleotide analogue can be incorporated base specifically by DNA polymerase into a growing DNA strand. The small peak at m/z 5872 corresponding to the photocleavage product is due to the partial cleavage caused by the nitrogen laser pulse (337 nm) used in MALDI ionization. For photocleavage, a Nd-YAG laser was used to irradiate the DNA product carrying the fluorescent nucleotide for 10 seconds at 355 nm to cleave the fluorophore from the DNA extension product. FIG. 19(2) shows the photocleavage result of the above DNA product. The peak at m/z 6536 has completely disappeared while the peak corresponding to the photocleavage product 5'-U (2) appears as the sole dominant peak at m/z 5872, which establishes that laser irradiation completely cleaves the fluorophore with high speed and efficiency without damaging the DNA. The next extension reaction was carried out using this photocleaved DNA product as a primer along with dGTP-PC-Bodipy-FL-510 to yield an extension product 5'-UG(PC-Bodipy-FL-510)-3' (3). As described above, the extension product 3 was purified, analyzed by MALDI-TOF MS producing a dominant peak at m/z 6751 [FIG. 19(3)], and then photocleaved for further MS analysis yielding a single peak at m/z 6255 (product 4) [FIG. 19(4)]. The third extension using dATP-PC-ROX to yield 5'-UGA(PC-ROX)-3' (5), the fourth extension using dCTP-PC-Bodipy-650 to yield 5'-UGAC(PC-Bodipy-650)-3' (7) and their photocleavage to yield products 6 and 8 were similarly carried out and analyzed by MALDI-TOF MS as shown in FIGS. 19(5), 19(6), 19(7) and 19(8). These results demonstrate that the above-synthesized four photocleavable fluorescent nucleotide analogues can successfully incorporate into the growing DNA strand in a polymerase reaction, and the fluorophore can be efficiently cleaved by near UV irradiation, which makes it feasible to use them for SBS on a chip.

Figure 20:
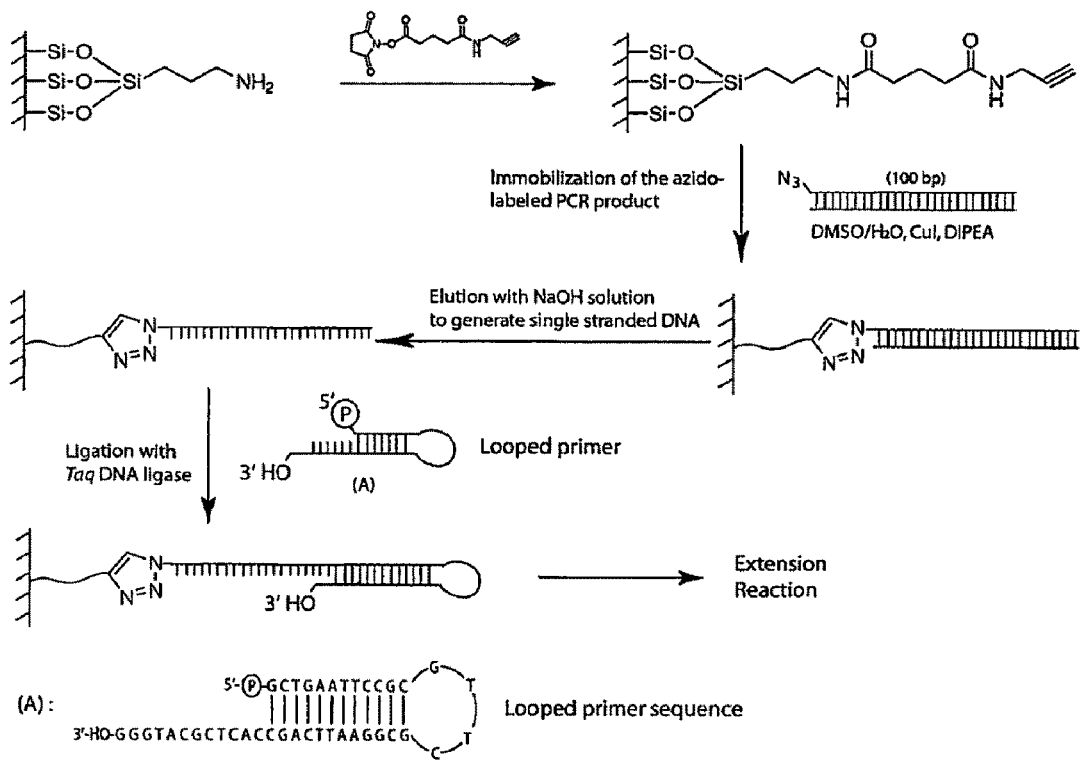
FIG. 20: Immobilization of an azido-labeled PCR product on an alkynyl-functionalized surface and a ligation reaction between the immobilized single-stranded DNA template and a loop primer to form a self-priming DNA moiety on the chip. The sequence of the loop primer is shown in (A).

The photocleavable fluorescent nucleotide analogues were then used in an SBS reaction to identify the sequence of the DNA template immobilized on a solid surface as shown in FIG. 20. A site-specific 1,3-dipolar cycloaddition coupling chemistry was used to covalently immobilize the azido-labeled double-stranded PCR products on the alkynyl-functionalized surface in the presence of a Cu(I) catalyst. Previously, it has shown have shown that DNA is successfully immobilized on the glass surface by this chemistry and evaluated the functionality of the surface-bound DNA and the stability of the array using a primer extension reaction (57). The surface-immobilized double stranded PCR product was denatured using a 0.1 M NaOH solution to remove the complementary strand without the azido group, thereby generating a single-stranded PCR template on the surface. Then, a 5'-phosphorylated self-priming moiety (loop primer) was ligated to the 3'-end of the above single stranded DNA template using Taq DNA ligase (21). The structure of the loop primer was designed to bear a thermally stable loop (22) and stem sequence with a melting temperature of 89° C. The 12-bp overhanging portion of the loop primer was made complementary to the 12-bp sequence of the template at its 3' end to allow the Taq DNA ligase to seal the nick between the 5'-phosphate group of the loop primer and the 3'-hydroxyl group of the single-stranded DNA template. This produces a unique DNA moiety that can self-prime for the synthesis of a complementary strand. The ligation was found to be in quantitative yield in a parallel solution-phase reaction using the same primer and single-stranded DNA template.

Figure 21:
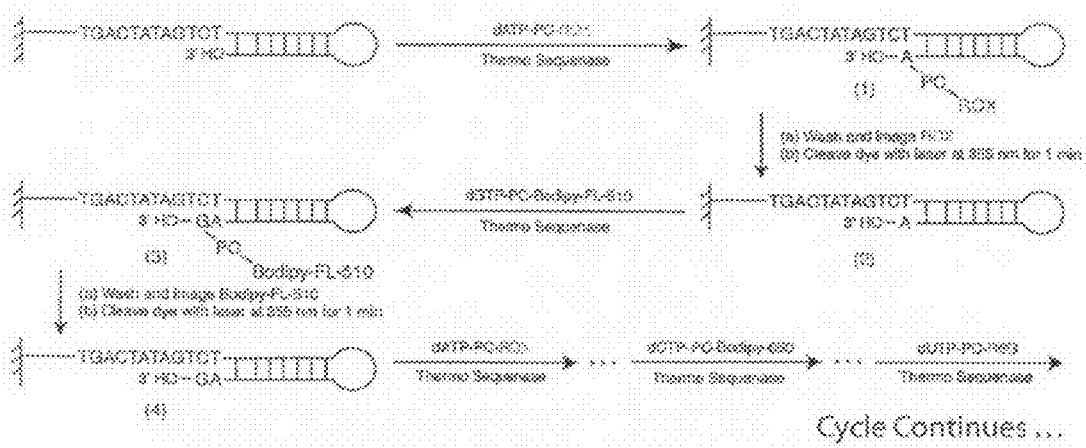
FIG. 21: Schematic representation of SBS on a chip using four PC fluorescent nucleotides (Upper panel) and the scanned fluorescence images for each step of SBS on a chip (Lower panel). (1) Incorporation of dATP-PC-ROX; (2) Photocleavage of PC-ROX; (3) Incorporation of dGTP-PC-Bodipy-FL-510; (4) Photocleavage of PC-Bodipy-FL-510; (5) Incorporation of dATP-PC-ROX; (6) Photocleavage of PC-ROX; (7) Incorporation of dCTP-PC-Bodipy-650; (8) Photocleavage of PC-Bodipy-650; (9) Incorporation of dUTP-PC-R6G; (10) Photocleavage of PC-R6G; (11) Incorporation of dATP-PC-ROX; (12) Photocleavage of PC-ROX; (13) Incorporation of dUTP-PC-R6G; (14) Photocleavage of PC-R6G; (15) Incorporation of dATP-PC-ROX; (16) Photocleavage of PC-ROX; (17) Incorporation of dGTP-PC-Bodipy-FL-510; (18) Photocleavage of PC-Bodipy-FL-510; (19) Incorporation of dUTP-PC-R6G; (20) Photocleavage of PC-R6G; (21) Incorporation of dCTP-PC-Bodipy-650; (22) Photocleavage of PC-Bodipy-650; (23) Incorporation of dATP-PC-ROX; (24) Photocleavage of PC-ROX.
Figure 21:
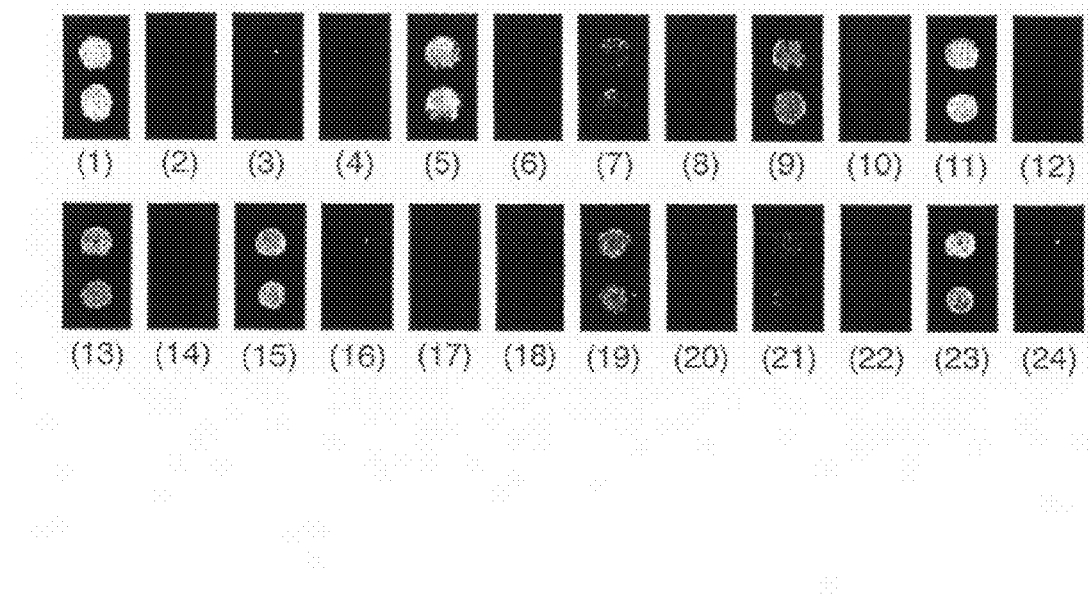
Figure 22:
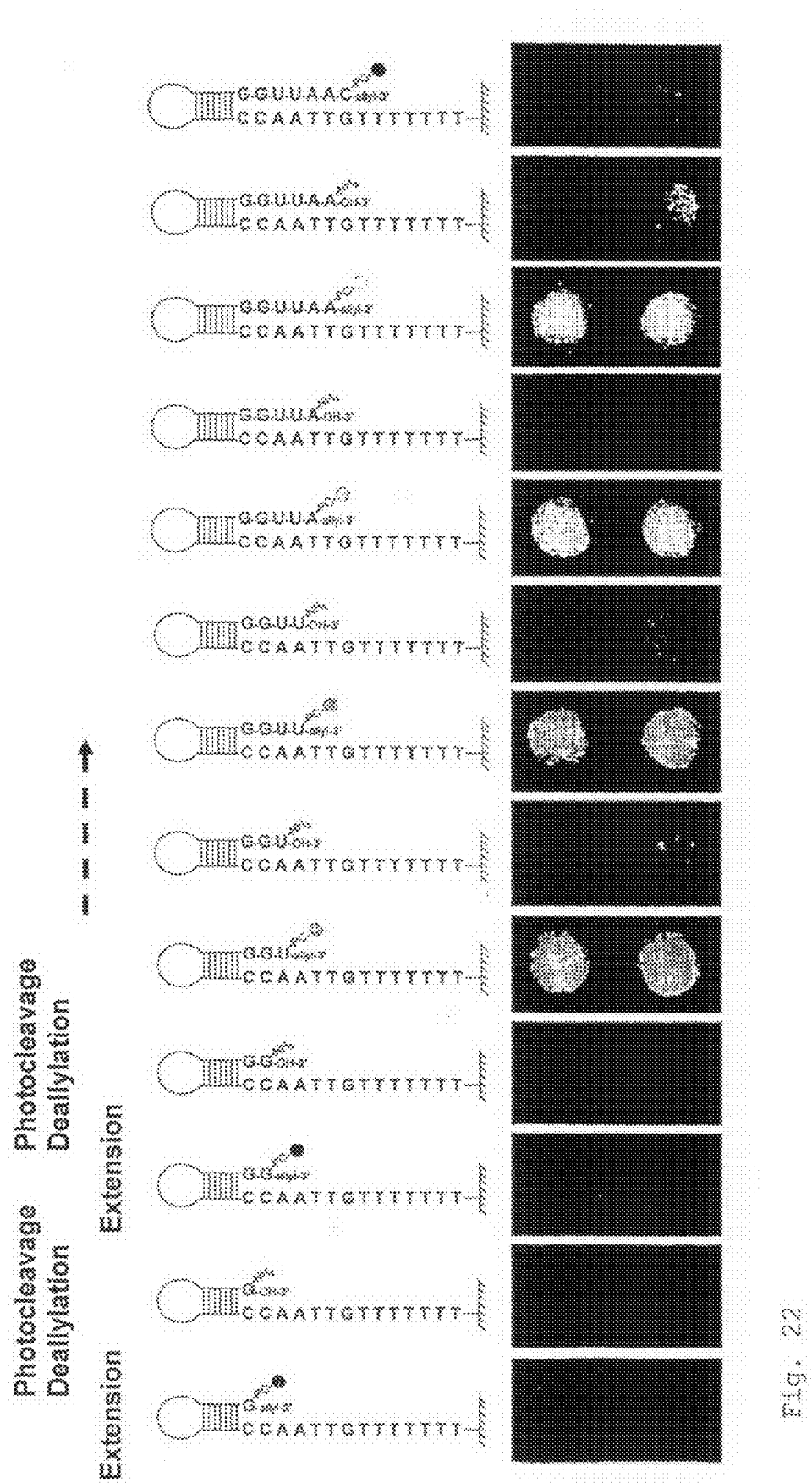
FIG. 22: 4-Color DNA sequencing data using 3'-O-allyl-dGTP-PC-Bodipy-FL-510, 3'-O-allyl-dATP-PC-ROX, 3'-O-allyl-dUTP-PC-R6G and 3'-O-allyl-dCTP-PC-Bodipy-650 as reversible terminators and a 4-color Laser Scanner. Scanned fluorescence images for each step of SBS on a DNA chip to sequence a DNA template with homopolymeric regions.

The principal advantage offered by the use of a self-priming moiety as compared to using separate primers and templates is that the covalent linkage of the primer to the template in the self-priming moiety prevents any possible dissociation of the primer from the template under vigorous washing conditions. Furthermore, the possibility of mispriming is considerably reduced and a universal loop primer can be used for all the templates allowing enhanced accuracy and ease of operation. SBS was performed on the chip-immobilized DNA template using the 4 photocleavable fluorescent nucleotide analogues and the results are shown in FIG. 21. The structure of the self-priming DNA moiety is shown schematically in the upper panel, with the first 12 nucleotide sequence immediately after the priming site. The sequencing reaction on the chip was initiated by extending the self-priming DNA using dATP-PC-ROX (complementary to the T on the template), and Thermo Sequenase DNA polymerase. After washing, the extension of the primer by a single fluorescent nucleotide was confirmed by observing an orange signal (the emission signal from ROX) in a microarray scanner [FIG. 21(1)]. After detection of the fluorescent signal, the surface was irradiated at 355 nm for 1 min using an Nd-YAG laser to cleave the fluorophore. The surface was then washed, and a negligible residual fluorescent signal was detected to confirm complete photocleavage of the fluorophore [FIG. 21(2)]. This was followed by incorporation of the next fluorescent nucleotide complementary to the subsequent base on the template. The entire process of incorporation, detection and photocleavage was performed multiple times using the four photocleavable fluorescent nucleotide analogues to identify 12 successive bases in the DNA template. The integrated fluorescence intensity on the spot, obtained from the scanner software, indicated that the incorporation efficiency was over 90% and more than 97% of the original fluorescence signal was removed by photocleavage. A negative control experiment consisting of incubating the self-priming DNA moiety with dATP-PC-ROX in the absence of DNA polymerase and washing the surface showed that negligible fluorescence remained as compared to that of FIG. 21(1).

In summary, synthesis and characterization of four photocleavable fluorescent nucleotide analogues are disclosed here, and their use to produce 4-color DNA sequencing data on a chip. These nucleotides have been shown to be excellent substrates for the DNA polymerase and the fluorophore could be cleaved efficiently using near UV irradiation. This is important with respect to enhancing the speed of each cycle in SBS for high throughput DNA analysis. It has also been demonstrated that a PCR-amplified DNA template can be ligated with a self-priming moiety and its sequence can be accurately identified in a DNA polymerase reaction on a chip, indicating that a PCR product from any organism can be potentially used as a template for the SBS system in the future. The modification of the 3'-OH of the photocleavable fluorescent nucleotide with a small chemical group to allow reversible termination is reported in (58). The library of photocleavable fluorescent nucleotides reported here should also facilitate the development of single molecule DNA sequencing approaches. Thus, by further improving the readlength and incorporation efficiency, this approach potentially can be developed into a high-throughput DNA-analysis system for biological research and medical applications.

REFERENCES

1. Lander, E. S., Linton, L. M., Birren, B., Nusbaum, C., Zody, M. C., Baldwin, J., Devon, K., Dewar, K., Doyle, M., FitzHugh, W. et al. (2001) *Nature* 409, 860-921.
2. Venter, J. C., Adams, M. D., Myers, E. W., Li, P. W., Mural, R. J., Sutton, G. G., Smith, H. O., Yandell, M., Evans, C. A., Holt, R. A. et al. (2001) *Science* 291, 1304-1351.
3. Roses, A. D. (2000) *Nature* 405, 857-865.
4. Collins, F. S., Green, E. D., Guttmacher, A. E. & Guyer, M. S. (2003) *Nature* 422, 835-847.
5. Friedman, L. S., Ostermeyer, E. A., Szabo, C. I., Dowd, P., Lynch, E. D., Rowell, S. E., & King, M.-C. (1994) *Nature Genetics* 8, 399-404.
6. Stickney, H. L., Schmutz, J., Woods, I. G., Holtzer, C. C., Dickson, M. C., Kelly, P. D., Myers, R. M. & Talbot, W. S. (2002) *Genome Res.* 12, 1929-1934.
7. Smith, L. M., Sanders, J. Z., Kaiser, R. J., Hughes, P., Dodd, C., Connell, C. R., Heiner, C., Kent, S. B. H. & Hood, L. E. (1986) *Nature* 321, 674-679.
8. Ju, J., Ruan, C., Fuller, C. W., Glazer, A. N. & Mathies, R. A. (1995) *Proc. Natl. Acad. Sci. USA* 92, 4347-4351.

9. Ju, J., Glazer, A. N. & Mathies, R. A. (1996) *Nucleic Acids Res.* 24, 1144-1148.
10. Kan, C. W., Fredlake, C. P, Doherty, E. A. S. & Barron, A. E. (2004) *Electrophoresis,* 25, 3564-3588.
11. Kheterpal, I., Scherer, J., Clark, S. M., Radhakrishnan, A., Ju, J., Ginther, C. L., Sensabaugh, G. F. & Mathies, R. A. (1996) *Electrophoresis* 17, 1852-1859.
12. Ju, J., Li, Z., Edwards, J. & Itagaki, Y. (2003) U.S. Pat. No. 6,664,079.
13. Li, Z., Bai, X., Ruparel, H., Kim, S., Turro, N. J. & Ju, J. (2003) *Proc. Natl. Acad. Sci. USA* 100, 414-419.
14. Seo, T. S., Bai, X., Ruparel, H., Li, Z., Turro, N. J. & Ju, J. (2004) *Proc. Natl. Acad. Sci. USA* 101, 5488-5493.
15. Seo, T. S., Bai, X., Kim D. H., Meng, Q., Shi, S., Ruparel, H., Li, Z., Turro, N. J. & Ju, J. (2005) "Four-Color DNA Sequencing by Synthesis on a Chip Using Photocleavable Nucleotides", submitted to *Proc. Natl. Acad. Sci. USA.*
16. Pelletier, H., Sawaya, M. R., Kumar, A., Wilson, S. H. & Kraut, J. (1994) *Science* 264, 1891-1903.
17. Axelrod, V. D., Vartikyan, R. M., Aivazashvili, V. A. & Beabealashvili, R. S. (1978) *Nucleic Acids Res.* 5, 3549-3563.
18. Metzker, M. L., Raghavachari, R., Richards, S., Jacutin, S. E., Civitello, A., Burgess, K. & Gibbs, R. A. (1994) *Nucleic Acids Res.* 22, 4259-4267.
19. Beabealashvili R. S., Scamrov, A. V., Kutateladze, T. V., Mazo, A. M., Krayevsky, A. A. & Kukhanova M. K. (1986) *Biochim. Biophys. Acta* 868, 136-144.
20. Kutateladze, T. V., Kritzyn, A. M., Florentjev, V. L., Kavsan, V. M., Chidgeavadze, Z. G. & Beabealashvili, R. S. (1986) *FEBS* 207, 205-212.
21. Chidgeavadze, Z. G. & Beabealashvili, R. S. (1984) *Nucleic Acids Res.* 12, 1671-1686.
22. Canard, B., Cardona, B. & Sarfati, R. S. (1995) *Proc. Natl. Acad. Sci. USA* 21, 10859-10863.
23. Guibe, F. (1998) *Tetrahedron* 54, 2967-3042.
24. Sabitha, G., Sbabu, R., Rajkumar, M., Srividya, R. & Yadav. J. S. (2001) *Org. Lett.* 3, 1149-1151.
25. Edwards, J. R., Itagaki, Y. & Ju, J. (2001) *Nucleic Acids Res.* 29, e104.
26. Karakawa, M., Kamitakahara, H., Takano, T. & Nakatsubo. F. (2002) *Biomacromolecules* 3, 538-546.
27. Honda, M., Morita, H. & Nagakura, I. (1997) *J. Org. Chem.* 62, 8932-8936.
28. Lacroix, T., Bricout, H., Tilloy, S. & Monflier, E. (1999) *Eur. J. Org. Chem.* 11, 3127-3129.
29. Lemaire, S., Savignac, M., Blart, E. & Bernard, J. M. (1997) *Tetrahedron Lett* 38, 2955-2958.
30. Genet, J. P., Blart, E. & Savignac, M. (1994) *Tetrahedron* 50(2), 497-503.
31. Milton, J., Wu, X., Smith, M., Brennan, J., Barnes, C., Liu, X. & Ruediger, S. (2004) PCT Intl. Patent. Appl. WO 0418497.
32. DeVasher, R. B., Moore, L. R. & Shaughnessy, K. H. (2004) *J. Org. Chem.* 69, 7919-7927.
33. Ju, J.; Li, Z.; Edwards, J.; Itagaki, Y. Massive parallel method for decoding DNA and RNA. 2003, U.S. Pat. No. 6,664,079.
34. (a) Ruparel, H.; Bi, L.; Li, Z.; Bai, X.; Kim, D. H.; Turro, N. J.; Ju, J. Design and synthesis of a 3'-O-allyl photocleavable fluorescent nucleotide as a reversible terminator for DNA sequencing by synthesis. *Proc. Natl. Acad. Sci. USA* 2005, 102, 5932-5937. (b) Seo, T. S.; Bai, X.; Kim, D. H.; Meng, Q.; Shi, S.; Ruparel, H.; Li, Z.; Turro, N. J.; Ju, J. Four-color DNA sequencing by synthesis on a chip using photocleavable fluorescent nucleotides. *Proc. Natl. Acad. Sci. USA* 2005, 102, 5926-5931.
35. See the Material and Methods section for experimental procedures and characterization data of the compounds synthesized.
36. Seela, F.; Driller, H. 7-deaza-2'-deoxy-O6-methylguanosine: selective N2-formylation via a formamidine, phosphoramidite synthesis and properties of oligonucleotides. *Nucl. Nucl.* 1989, 8, 1-21.
37. Ramzaeva, N.; Seela, F. 7-substituted 7-deaza-2'-deoxyguanosines: regioselective halogenation of pyrrolo[2,3-d] pyrimidine nucleoside. *Helv. Chim. Acta.* 1995, 78, 1083-1090.
38. Ryu, E. K.; Ross, R. J.; Matsushita, T.; MacCoss, M.; Hong, C. I.; West, C. R. Phospholipid-nucleoside conjugates. 3. syntheses and preliminary biological evaluation of 1-β-D-arabinofuranosylcytosine 5'-monophophate-L-1,2-dipalmitin and selected 1-β-D-arabinofuranosylcytosine 5'-diphsphate-L-1,2-diacylglycerosls. *J. Med. Chem.* 1982, 25, 1322-1329.
39. (a) Robins, M. J.; Vinayak, R. S.; Wood, S. G. Solvent, not palladium oxidation state, is the primary determinant for successful coupling of terminal alkynes with iodo-nucleosides. *Tetrahedron Lett.* 1990, 31, 3731-3734. (b) Hobbs, F. W. Palladium-catalyzed synthesis of alkynylamino nucleosides. A universal linker to nucleic acids. *J. Org. Chem.* 1989, 54, 3420-3422.
40. (a) Ramasamy, K.; Imarura, N.; Robins, R. K.; Revankar, G. R. a facile and improved tubercidin and certain related pyrrolo[2,3-d]pyrimidine nucleosides by the sterospecific sodium salt glycosylation procedure [1]. *J. Heterocyclic Chem.* 1988, 25, 1893-1898. (b) Ramasamy, K.; Imarura, N.; Robins, R. K.; Revankar, G. R. a facile synthesis of ubercidin and related 7-deazapurine nucleosides via the sterospecific sodium salt cgycosylation procedure. *Tetrahedron Lett.* 1987, 28, 5107-5110.
41. (a) Lee, S. E.; Sidorov, A.; Gourlain, T.; Mignet, N.; Thorpe, S. J.; Brazier, J. A.; Dickman, M. J.; Hornby, D. P.; Grasby, J. A.; Williams, D. M. enhancing the catalytic repertoire of nucleic acids: a systematic study of linker length and rigidity. *Nucleic Acids Res.* 2001, 29, 1565-1573. (b) Giller, G.; Tasara, T.; Angerer, B.; Mühlegger, K; Amacker, M.; Winter, H. Incorporation of reporter molecule-labeled nucleotides by DNA polymerase. I. Chemical synthesis of various reporter group-labeled 2'-deoxyribonucleoside-5'-triphosphate. *Nucleic Acids Res.* 2003, 31, 2630-2635.
42. Collins, F. S., Green, E. D., Guttmacher, A. E. & Guyer, M. S. (2003) *Nature* 422, 835-847.
43. Thomas, J. W., Touchman, J. W., Blakesley, R. W., Bouffard, G. G., Beckstrom-Sternberg, S. M., Margulies, E. H., Blanchette, M., Siepel, A. C., Thomas, P. J. & McDowell, J. C. et al. (2003) *Nature* 424, 788-793.
44. Smith, L. M., Sanders, J. Z., Kaiser, R. J., Hughes, P., Dodd, C., Connell, C. R., Heiner, C., Kent, S. B. H. & Hood, L. E. (1987) *Nature* 321, 674-679.
45. Ju, J., Ruan, C., Fuller, C. W., Glazer, A. N. & Mathies, R. A. (1995) *Proc. Natl. Acad. Sci. USA* 92, 4347-4351.
46. Doherty, E. A. S., Kan, C. W. and Barron, A. E. (2003) *Electrophoresis,* 24, 4170-4180.
47. Drmanac, S., Kita, D., Labat, I., Hauser, B., Schmidt, C., Burczak, J. D. & Drmanac, R. (1998) *Nat. Biotechnol.* 16, 54-58.
48. Fu, D. J., Tang, K., Braun, A., Reuter, D., Darnhofer-Demar, B., Little, D. P., O'Donnell, M. J., Cantor, C. R. & Koster, H. (1998) *Nat. Biotechnol.* 16, 381-384.
49. Roskey, M. T., Juhasz, P., Smirnov, I. P., Takach, E. J., Martin, S. A. & Haff, L. A. (1996) *Proc. Natl. Acad. Sci. USA* 93, 4724-4729.

50. Edwards, J. R., Itagaki, Y. & Ju, J. (2001) *Nucleic Acids Res.* 29, e104 (p 1-6).
51. Kasianowicz, J. J., Brandin, E., Branton, D. & Deamer, D. W. (1996) *Proc. Natl. Acad. Sci. USA* 93, 13770-13773.
52. Ronaghi, M., Uhlen, M. & Nyren, P. (1998) *Science* 281, 363-365.
53. Braslavsky, I., Hebert, B., Kartalov, E. & Quake, S. R. (2003) *Proc. Natl. Acad. Sci. USA* 100, 3960-3964.
54. Mitra, R. D., Shendure, J., Olejnik, J., Olejnik, E. K. & Church, G. M. (2003) *Anal. Biochem.* 320, 55-65.
55. Hyman, E. D. (1988) *Anal. Biochem.* 174, 423-436.
56. Ju, J., Li, Z., Edwards, J. & Itagaki, Y. (2003) U.S. Pat. No. 6,664,079.
57. Seo, T. S., Bai, X., Ruparel, H., Li, Z., Turro, N. J. & Ju, J. (2004) *Proc. Natl. Acad. Sci. USA,* 101, 5488-5493.
58. Ruparel, H., Bi, L., Li, Z., Bai, X., Kim, D. H., Turro, N. J. & Ju, J. Design and Synthesis of a 3'-O-Allyl Modified Photocleavable Fluorescent Nucleotide as Reversible Terminator for DNA Sequencing by Synthesis (2005) submitted to *Proc. Natl. Acad. Sci. USA.*
59. Rosenblum, B. B., Lee, L. G., Spurgeon, S. L., Khan, S. H., Menchen, S. M., Heiner, C. R. & Chen, S. M. (1997) *Nucleic Acids Res.* 25, 4500-4504.
60. Zhu, Z., Chao, J., Yu, H. & Waggoner, A. S. (1994) *Nucleic Acids Res.* 22, 3418-3422
61. Rajasekharan Pillai, V. N. (1980) *Synthesis* 1, 1-26.
62. Barany, F. (1991) *Proc. Natl. Acad. Sci. USA* 88, 189-193.
63. Antao, V. P., Lai, S. Y. & Tinoco, I. Jr. (1991) *Nucleic Acids Res.* 19, 5901-5905.

What is claimed is:

1. A method for making 3'O-allyl-dGTP-PC-Bodipy-FL-510 comprising performing the steps set forth in FIG. 7.

2. A method for making 3'-O-allyl-dATP-PC-ROX comprising performing the steps set forth in FIG. 8.

3. A method for making 3'-(D-allyl-dCTP-PC-Bodipy-650 comprising performing the steps set forth in FIG. 9.

4. A method for making 3'-O-allyl-dUTP-PC-R6G comprising performing the steps set forth in FIG. 10.

* * * * *

SEQUENCE LISTING

```
<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: primer directed to Human p53

<400> SEQUENCE: 1
agaggatcca accgagact                                                    19

<210> SEQ ID NO 2
<211> LENGTH: 18
<212> TYPE: DNA
<213> ORGANISM: Homo sapiens

<400> SEQUENCE: 2
agaggatcca accgagac                                                     18

<210> SEQ ID NO 3
<211> LENGTH: 19
<212> TYPE: DNA
<213> ORGANISM: Artificial Sequence
<220> FEATURE:
<223> OTHER INFORMATION: chemically synthesized

<400> SEQUENCE: 3
agaggatcca accgagact                                                    19

<210> SEQ ID NO 4
<211> LENGTH: 20
<212> TYPE: DNA
<213> ORGANISM: Artificial Sequence
<220> FEATURE:
<223> OTHER INFORMATION: primer directed to Human p53

<400> SEQUENCE: 4
gttgatgtac acattgtcaa                                                   20

<210> SEQ ID NO 5
<211> LENGTH: 100
<212> TYPE: DNA
<213> ORGANISM: Homo sapiens

<400> SEQUENCE: 5
tacccggagg ccaagtacgg cgggtacgtc cttgacaatg tgtacatcaa catcacctac       60
caccatgtca gtctcggttg gatcctctat tgtgtccggg                            100
```

<210> SEQ ID NO 6
<211> LENGTH: 100
<212> TYPE: DNA
<213> ORGANISM: Homo sapiens

<400> SEQUENCE: 6
tacccggagg ccaagtacgg cgggtacgtc cttgacaatg tgtacatcaa catcacctac    60
caccatgtca gtctcggttg gatcctctat tgtgtccggg                          100

<210> SEQ ID NO 7
<211> LENGTH: 20
<212> TYPE: DNA
<213> ORGANISM: Artificial Sequence
<220> FEATURE:
<223> OTHER INFORMATION: primer directed to Human p53

<400> SEQUENCE: 7
tagatgaccc tgccttgtcg                                                20

<210> SEQ ID NO 8
<211> LENGTH: 109
<212> TYPE: DNA
<213> ORGANISM: Homo sapiens

<400> SEQUENCE: 8
gaaggagaca cgcggccaga gagggtcctg tccgtgtttg tgcgtggagt tcgacaaggc    60
agggtcatct aatggtgatg agtcctatcc ttttctcttc gttctccgt                109

<210> SEQ ID NO 9
<211> LENGTH: 24
<212> TYPE: DNA
<213> ORGANISM: Artificial Sequence
<220> FEATURE:
<223> OTHER INFORMATION: primer directed to Human p53

<400> SEQUENCE: 9
acacaataga ggatccaacc gaga                                           24

<210> SEQ ID NO 10
<211> LENGTH: 100
<212> TYPE: DNA
<213> ORGANISM: Homo sapiens

<400> SEQUENCE: 10
tacccggagg ccaagtacgg cgggtacgtc cttgacaatg tgtacatcaa catcacctac    60
caccatgtca gtctcggttg gatcctctat tgtgtccggg                          100

<210> SEQ ID NO 11
<211> LENGTH: 17
<212> TYPE: DNA
<213> ORGANISM: Artificial Sequence
<220> FEATURE:
<223> OTHER INFORMATION: primer directed to Human p53

<400> SEQUENCE: 11
gataggactc atcacca                                                   17

<210> SEQ ID NO 12
<211> LENGTH: 109
<212> TYPE: DNA
<213> ORGANISM: Homo sapiens

<400> SEQUENCE: 12

```
gaaggagaca cgcggccaga gagggtcctg tccgtgtttg tgcgtggagt tcgacaaggc    60
agggtcatct aatggtgatg agtcctatcc ttttctcttc gttctccgt              109
```

<210> SEQ ID NO 13
<211> LENGTH: 18
<212> TYPE: DNA
<213> ORGANISM: Artificial Sequence
<220> FEATURE:
<223> OTHER INFORMATION: primer directed to Human p53

<400> SEQUENCE: 13

```
agaggatcca accgagac                                                  18
```

<210> SEQ ID NO 14
<211> LENGTH: 60
<212> TYPE: DNA
<213> ORGANISM: Homo sapiens

<400> SEQUENCE: 14

```
gtgtacatca acatcaccta ccaccatgtc agtctcggtt ggatcctcta ttgtgtccgg    60
```

<210> SEQ ID NO 15
<211> LENGTH: 100
<212> TYPE: DNA
<213> ORGANISM: Homo sapiens

<400> SEQUENCE: 15

```
agcgactgct atcatgtcat atcgacgtgc tcactagctc tacatatgcg tgcgtgatca    60
gatgacgtat cgatgctgac tatagtctcc catgcgagtg                         100
```

<210> SEQ ID NO 16
<211> LENGTH: 24
<212> TYPE: DNA
<213> ORGANISM: Artificial Sequence
<220> FEATURE:
<223> OTHER INFORMATION: forward primer directed to Human p53

<400> SEQUENCE: 16

```
agcgactgct atcatgtcat atcg                                           24
```

<210> SEQ ID NO 17
<211> LENGTH: 24
<212> TYPE: DNA
<213> ORGANISM: Artificial Sequence
<220> FEATURE:
<223> OTHER INFORMATION: reverse primer directed to Human p53

<400> SEQUENCE: 17

```
cactcgcatg ggagactata gtca                                           24
```

<210> SEQ ID NO 18
<211> LENGTH: 40
<212> TYPE: DNA
<213> ORGANISM: Artificial Sequence
<220> FEATURE:
<223> OTHER INFORMATION: primer directed to Human p53

<400> SEQUENCE: 18

```
gctgaattcc gcgttcgcgg aattcagcca ctcgcatggg                          40
```